United States Patent
Pei

(10) Patent No.: US 11,510,991 B2
(45) Date of Patent: Nov. 29, 2022

(54) POLYPEPTIDE CONJUGATES FOR INTRACELLULAR DELIVERY OF STAPLED PEPTIDES

(71) Applicant: Ohio State Innovation Foundation, Columbus, OH (US)

(72) Inventor: Dehua Pei, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/759,600

(22) PCT Filed: Oct. 28, 2018

(86) PCT No.: PCT/US2018/057894
§ 371 (c)(1),
(2) Date: Apr. 27, 2020

(87) PCT Pub. No.: WO2019/084528
PCT Pub. Date: May 2, 2019

(65) Prior Publication Data
US 2020/0276323 A1    Sep. 3, 2020

Related U.S. Application Data

(60) Provisional application No. 62/578,213, filed on Oct. 27, 2017.

(51) Int. Cl.
| | |
|---|---|
| *C07K 14/47* | (2006.01) |
| *A61K 47/64* | (2017.01) |
| *A61K 47/58* | (2017.01) |
| *A61P 35/00* | (2006.01) |
| *C07K 14/00* | (2006.01) |

(52) U.S. Cl.
CPC ............. *A61K 47/64* (2017.08); *A61K 47/58* (2017.08); *A61P 35/00* (2018.01); *C07K 14/001* (2013.01); *C07K 14/4703* (2013.01)

(58) Field of Classification Search
CPC ........ A61K 47/64; A61K 47/58; A61K 38/00; A61P 35/00; C07K 14/001; C07K 14/4703; C07K 7/52
See application file for complete search history.

(56) References Cited

U.S. PATENT DOCUMENTS

| | | | |
|---|---|---|---|
| 6,960,648 B2 | 11/2005 | Bonny | |
| 2002/0035243 A1 | 3/2002 | Imfeld et al. | |
| 2002/0120100 A1 | 8/2002 | Bonny | |
| 2003/0032594 A1 | 2/2003 | Bonny | |
| 2016/0151512 A1 | 6/2016 | Kim et al. | |
| 2017/0190743 A1 | 7/2017 | Pei | |
| 2017/0355730 A1 | 12/2017 | Pei | |
| 2019/0282654 A1 | 9/2019 | Pei | |
| 2019/0309020 A1 | 10/2019 | Pei | |
| 2020/0353092 A1 | 11/2020 | Foster et al. | |

FOREIGN PATENT DOCUMENTS

| | | |
|---|---|---|
| WO | 2013123266 A | 8/2013 |
| WO | 2013/150338 A1 | 10/2013 |
| WO | 2015153761 A | 10/2015 |
| WO | 2015179691 A | 11/2015 |
| WO | 2017/147283 A1 | 8/2017 |
| WO | 2018089648 | 5/2018 |
| WO | 2018098231 | 5/2018 |

OTHER PUBLICATIONS

Bowie et al. (Science, 1990, 247:1306-1310) (Year: 1990).*
Burgess etal (J. Cell Biol. 111:2129-2138, 1990) (Year: 1990).*
Lazaret al (Mol. Cell. Biol., 8:1247-1252, 1988) (Year: 1988).*
He et al, Molecules, 2019, 24, 1855 (Year: 2019).*
Lu et al, International Journal of Molecular Sciences, 2016, 17, 561, 1-22 (Year: 2016).*
Chen et al. Adv. Drug Deliv. Rev. 65:1357-1369 (Year: 2013).*
Assem, N., et al., (2015) "Acetone-linked peptides: a convergent approach for peptide macrocyclization and labeling". Angew. Chem. Int. Ed. 54, 8665-8668.
Bird, Gregory H., et al. "Biophysical determinants for cellular uptake of hydrocarbon-stapled peptide helices." Nature Chem. Biol.12.10 (2016): 845-852.
Chu, Qian, et al. "Towards understanding cell penetration by stapled peptides." MedChemComm 6.1 (2015): 111-119.
clinicaltrials.gov identifier: NCT02264613, First Posted: Oct. 15, 2014.
Eisenberg, David, Robert M. Weiss, and Thomas C. Terwilliger. "The hydrophobic moment detects periodicity in protein hydrophobicity." protein antigenic determinants from amino acid sequences. Proc. Nat'l. Acad. Sci. 81.1 (1984): 140-144.
Engel, Marisa, et al. "Regiospecific synthesis of 3, 5-bis (bromomethyl) benzoic acid, a cysteine crosslinking agent." Tetrahedron 49.39 (1993): 8761-8770.
Engelman, D. M., T. A. Steitz, and A. Goldman. "Identifying nonpolar transbilayer helices in amino acid sequences of membrane proteins." Ann. Rev. Biophysics Biophysical Chem. 15.1 (1986): 321-353.
Fang, Shengyun, et al. "Mdm2 is a RING finger-dependent ubiquitin protein ligase for itself and p53." J. Biol. Chem. 275.12 (2000): 8945-8951.

(Continued)

*Primary Examiner* — Sudhakar Katakam

(74) *Attorney, Agent, or Firm* — Meunier Carlin & Curfman LLC

(57) ABSTRACT

The present disclosure provides novel polypeptide conjugates. The polypeptide conjugates disclosed herein comprise a stapled peptide comprising a peptide and at least one staple which holds the peptide in an α-helical conformation, and a cyclic cell-penetrating peptide (cCPP) conjugated, directly or indirectly, to the stapled peptide. The present disclosure demonstrates that cCPPs can be used to confer consistent cell-permeability to stapled peptides.

12 Claims, 51 Drawing Sheets

Specification includes a Sequence Listing.

(56) References Cited

OTHER PUBLICATIONS

Hopp, Thomas P., and Kenneth R. Woods. "Prediction of protein antigenic determinants from amino acid sequences." Proc. Nat'l. Acad. Sci. 78.6 (1981): 3824-3828.
Hu, B., Gilkes, D. M., and Chen, J. (2007) Efficient p53 activation and apoptosis by simultaneous disruption of binding to MDM2 and MDMX. Cancer Res. 67, 8810-8817.
Janin, J. O. E. L. "Surface and inside vols. in globular proteins." Nature 277.5696 (1979): 491-492.
Jo, Hyunil, et al. "Development of α-helical calpain probes by mimicking a natural protein—protein interaction." J. Am. Chem. Soc. 134.42 (2012): 17704-17713.
Joy, Stephen T., and Paramjit S. Arora. "An optimal hydrogen-bond surrogate for α-helices." Chem. Commun. 52.33 (2016): 5738-5741.
Kyte, Jack, and Russell F. Doolittle. "A simple method for displaying the hydropathic character of a protein." J. Mol. Biol. 157.1 (1982): 105-132.
Lau, Yu Heng, et al. "Peptide stapling techniques based on different macrocyclisation chemistries." Chem. Soc. Rev. 44.1 2014.
Madden, Michael M., et al. "Synthesis of cell-permeable stapled peptide dual inhibitors of the p53-Mdm2/Mdmx interactions via photoinduced cycloaddition." Bioorganic & Med. Chem. Lett. 21.5 (2011): 1472-1475.
Phan, Jason, et al. "Structure-based design of high affinity peptides inhibiting the interaction of p53 with MDM2 and MDMX." J. Biol. Chem. 285.3 (2010): 2174-2183.
Qian, Ziqing, et al. "Discovery and mechanism of highly efficient cyclic cell-penetrating peptides." Biochemistry 55.18 (2016): 2601-2612.
Qian, Ziqing, et al. "Early endosomal escape of a cyclic cell-penetrating peptide allows effective cytosolic cargo delivery." Biochemistry 53.24 (2014): 4034-4046.
Qian, Ziqing, et al. "Efficient delivery of cyclic peptides into mammalian cells with short sequence motifs." ACS Chem. Biol. 8.2 (2013): 423-431.
Qian, Ziqing, Patrick G. Dougherty, and Dehua Pei. "Monitoring the cytosolic entry of cell-penetrating peptides using a pH-sensitive fluorophore." Chem. Commun. 51.11 (2015): 2162-2165.
Shair, Matthew D. "A closer view of an oncoprotein-tumor suppressor interaction." Chem. & Biol. 4.11 (1997): 791-794.
Shrake, Andrew, and John A. Rupley. "Environment and exposure to solvent of protein atoms. Lysozyme and insulin." J. Mol. Biol. 79.2 (1973): 351-371.
Tien, Matthew Z., et al. "Maximum allowed solvent accessibilities of residues in proteins." PloS one 8.11 (2013): e80635.
Vassilev, Lyubomir T., et al. "In vivo activation of the p53 pathway by small-molecule antagonists of MDM2." Science 303.5659 (2004): 844-848.
Verdine, Gregory L., and Gerard J. Hilinski. "Stapled peptides for intracellular drug targets." Methods in enzymology. vol. 503. Academic Press, 2012. 3-33.
Wade, Mark, Yao-Cheng Li, and Geoffrey M. Wahl. "MDM2, MDMX and p53 in oncogenesis and cancer therapy." Nature Reviews Cancer 13.2 (2013): 83-96.
Walensky, Loren D., and Gregory H. Bird. "Hydrocarbon-stapled peptides: principles, practice, and progress: miniperspective." J. Med. Chem. 57.15 (2014): 6275-6288.
Walensky, Loren D., et al. "Activation of apoptosis in vivo by a hydrocarbon-stapled BH3 helix." Science 305.5689 (2004): 1466-1470.
Zhao, H. et al. "Crosslinked Aspartic Acids as Helix-Nucleating Templates", Angew. Chem. Int. Ed. 2016, 55, 12088-12093.
International Preliminary Report on Patentability issued for Application No. PCT/US2018/057894 dated May 7, 2020.
International Search Report and Written Opinion issued by the International Searching Authority (ISA/US) in PCT Application No. PCT/US2018/057894 dated Jan. 15, 2019. 10 pages.
Tian, Yuan, et al. "Achieving enhanced cell penetration of short conformationally constrained peptides through amphiphilicity tuning." Chemical science 8.11 (2017): 7576-7581.
Kim, Young-Woo, Tom N. Grossmann, and Gregory L. Verdine. "Synthesis of all-hydrocarbon stapled α-helical peptides by ring-closing olefin metathesis." Nature protocols 6.6 (2011): 761-772.
Extended European Search Report, issued by the European Patent Office in European Application No. 18870802.8 dated Jun. 22, 2021. 8 pages.
Tan, Yaw Sing, David P. Lane, and Chandra S. Verma. "Stapled peptide design: principles and roles of computation." Drug Discovery Today 21.10 (2016): 1642-1653.
Cromm, Philipp M., Jochen Spiegel, and Tom N. Grossmann. "Hydrocarbon stapled peptides as modulators of biological function." ACS chemical biology 10.6 (2015): 1362-1375.
Japanese Application Serial No. 2020-543254, Notification of Reasons for Refusal filed Sep. 13, 2022.

\* cited by examiner

Aminoxy-CPP9

Molecular Weight: 1443.69

Structure 10

Structure 11

Molecular Weight: 3791.29

Structure 12

Molecular Weight: 2523.77

Structure 13

Structure 14

Molecular Weight: 1705.03

Structure 16

Molecular Weight: 2418.75

Purification of crude stapled peptide by semi-preparative HPLC (214 nm):

Peptide 16 (two species due to two isomers of the NF dye)

Structure 17

Molecular Weight: 3815.37

Structure 18

Structure 19

Molecular Weight: 3685.26

Structure 21

Molecular Weight: 3755.26

Structure 22 (sPDI)

Structure 23 (CPP9-sPD1)

Structure 24 (R9-sPDI)

Structure 25 (Tat-sPDI)

SEQUENCE LISTING

<160> NUMBER OF SEQ ID NOS: 47

<210> SEQ ID NO 1
<211> LENGTH: 12
<212> TYPE: PRT
<213> ORGANISM: Artificial Sequence

```
<220> FEATURE:
<223> OTHER INFORMATION: Synthetic Construct

<400> SEQUENCE: 1

Leu Thr Phe Glu His Tyr Trp Ala Gln Leu Thr Ser
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Cys Arg Arg Arg Arg Phe Trp Gln
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Selenocysteine
<220> FEATURE:
<221> NAME/KEY: MOD_RES
<222> LOCATION: (1)..(1)

<400> SEQUENCE: 3

Xaa Arg Arg Arg Arg Phe Trp Gln
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Cys Arg Arg Arg Arg Phe Trp Gln
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Phe Trp Arg Arg Arg
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Arg Arg Arg Trp Phe
1               5
```

```
<210> SEQ ID NO 7
<211> LENGTH: 6
<212> TYPE: PRT
<213> ORGANISM: Artificial Sequence
<220> FEATURE:
<223> OTHER INFORMATION: Synthetic Construct

<400> SEQUENCE: 7

Phe Phe Arg Arg Arg Gln
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Phe Arg Phe Arg Arg Gln
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct

<400> SEQUENCE: 9

Phe Arg Arg Phe Arg Gln
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

Phe Arg Arg Arg Phe Gln
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct

<400> SEQUENCE: 11

Phe Phe Phe Arg Ala Gln
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

Phe Phe Phe Arg Arg Gln
1               5
```

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Phe Phe Arg Arg Arg Arg Gln
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Phe Arg Arg Phe Arg Arg Gln
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct

<400> SEQUENCE: 15

Phe Arg Arg Arg Phe Arg Gln
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Construct

<400> SEQUENCE: 16

Arg Phe Phe Arg Arg Arg Gln
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct

<400> SEQUENCE: 17

Arg Phe Arg Arg Phe Arg Gln
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

Phe Arg Phe Arg Arg Arg Gln
1               5

```
<210> SEQ ID NO 19
<211> LENGTH: 7
<212> TYPE: PRT
<213> ORGANISM: Artificial Sequence
<220> FEATURE:
<223> OTHER INFORMATION: Synthetic Construct

<400> SEQUENCE: 19

Phe Phe Phe Arg Arg Arg Gln
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic Construct

<400> SEQUENCE: 20

Phe Phe Arg Arg Arg Phe Gln
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Phe Arg Phe Phe Arg Arg Gln
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic Construct

<400> SEQUENCE: 22

Arg Arg Phe Phe Phe Arg Gln
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

Phe Phe Arg Phe Arg Arg Gln
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct

<400> SEQUENCE: 24

Phe Phe Arg Arg Phe Arg Gln
1               5

<210> SEQ ID NO 25
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Phe Arg Arg Phe Phe Arg Gln
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic Construct

<400> SEQUENCE: 26

Phe Arg Arg Phe Arg Phe Gln
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic Construct

<400> SEQUENCE: 27

Phe Arg Phe Arg Phe Arg Gln
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Construct

<400> SEQUENCE: 28

Arg Phe Phe Arg Phe Arg Gln
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic Construct

<400> SEQUENCE: 29

Phe Phe Phe Arg Arg Arg Arg Gln
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Construct

<400> SEQUENCE: 30

Arg Phe Phe Arg Arg Arg Arg Gln
1               5

<210> SEQ ID NO 31
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 31

Arg Arg Phe Phe Arg Arg Arg Gln
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Construct

<400> SEQUENCE: 32

Arg Phe Phe Phe Arg Arg Arg Gln
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic Construct

<400> SEQUENCE: 33

Arg Arg Phe Phe Phe Arg Arg Gln
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

<400> SEQUENCE: 34

Phe Phe Arg Arg Phe Arg Arg Gln
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic Construct

<400> SEQUENCE: 35

Phe Phe Arg Arg Arg Arg Phe Gln
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Phe Arg Arg Phe Phe Arg Arg Gln
1               5

<210> SEQ ID NO 37
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 37

Phe Phe Phe Arg Arg Arg Arg Gln
1               5

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct

<400> SEQUENCE: 38

Phe Phe Phe Arg Arg Arg Arg Arg Arg Gln
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Xaa can be any naturally occurring amino acid

<400> SEQUENCE: 39

Xaa Xaa Arg Arg Arg Arg Gln
1               5

<210> SEQ ID NO 40
<211> LENGTH: 12
<212> TYPE: PRT
<213> ORGANISM: Artificial Sequence
<220> FEATURE:
<223> OTHER INFORMATION: Synthetic Construct

<400> SEQUENCE: 40

Leu Thr Phe Cys His Tyr Trp Cys Gln Leu Thr Ser
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetic Construct

<400> SEQUENCE: 41

Leu Thr Phe His Cys His Tyr Trp His Cys Gln Leu Thr Ser
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic Construct

<400> SEQUENCE: 42

Glu Thr Phe Cys His Tyr Trp Cys Gln Leu Thr Ser
1               5                   10
```

```
<210> SEQ ID NO 43
<211> LENGTH: 13
<212> TYPE: PRT
<213> ORGANISM: Artificial Sequence
<220> FEATURE:
<223> OTHER INFORMATION: Synthetic Construct

<400> SEQUENCE: 43

Glu Glu Thr Phe Cys His Tyr Trp Cys Gln Leu Thr Ser
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Synthetic Construct

<400> SEQUENCE: 44

Arg Lys Phe Cys Arg Leu Phe Cys
1               5

<210> SEQ ID NO 45
<211> LENGTH: 15
<212> TYPE: PRT
<213> ORGANISM: Artificial Sequence
<220> FEATURE:
<223> OTHER INFORMATION: Synthetic Construct

<400> SEQUENCE: 45

Glu Asn Pro Glu Cys Ile Leu Asp Cys His Val Gln Arg Val Met
1               5                   10                  15

<210> SEQ ID NO 46
<211> LENGTH: 14
<212> TYPE: PRT
<213> ORGANISM: Artificial Sequence
<220> FEATURE:
<223> OTHER INFORMATION: Synthetic Construct

<400> SEQUENCE: 46

Asn Pro Glu Cys Ile Leu Asp Cys His Val Gln Arg Val Met
1               5                   10

<210> SEQ ID NO 47
<211> LENGTH: 16
<212> TYPE: PRT
<213> ORGANISM: Artificial Sequence
<220> FEATURE:
<223> OTHER INFORMATION: Synthetic Construct

<400> SEQUENCE: 47

Thr Tyr Arg Gly Ala Ala Gln Cys Ala Ala Gln Cys Val Arg Glu Val
1               5                   10                  15
```

POLYPEPTIDE CONJUGATES FOR INTRACELLULAR DELIVERY OF STAPLED PEPTIDES

CROSS-REFERENCE TO RELATED APPLICATION

This application is a national stage application filed under 35 U.S.C. § 371 of PCT/US2018/057894 filed Oct. 28, 2018, which claims the benefit of priority to U.S. Provisional Application No. 62/578,213, filed Oct. 27, 2017, the entire contents of which are herein incorporated by reference in its entirety for all purposes.

STATEMENT CONCERNING GOVERNMENT FUNDING

This invention was made with government support under grant nos. R01-GM110208 and R35-GM122459, each awarded by the National Institute of General Medical Sciences (NIGMS), NIH. The government has certain rights in the invention.

BACKGROUND

Stapled peptides have emerged as an exciting class of therapeutic agents for targeting intracellular protein-protein interactions (PPIs), which have been challenging targets for conventional small molecules and biologics. Verdine G. L., et al., *Methods Enzymol.* 503, 3-33 (2012); Walensky, L. D., et al., *J Med. Chem.* 57, 6275-6288 (2014). They recapitulate the structure and specificity of bioactive α-helices, resist proteolytic degradation in vivo, and, when appropriately designed, gain access to the cytosol and nucleus of mammalian cells. The first cellular application of hydrocarbon-stapled α-helices, which were modeled after the BCL-2 homology 3 (BH3) domain of the pro-apoptotic protein BID, revealed their capacity for cellular uptake by an energy-dependent macro-pinocytic mechanism, resulting in activation of the apoptotic signaling cascade. Chu, Q., et al., *Med. Chem. Commun.* 6, 111-119 (2015) (clinicaltrials.gov identifier: NCT02264613).

Despite the remarkable promise of stapled peptides as a novel class of therapeutics for targeting previously intractable proteins, designing stapled peptides with consistent cell-permeability remains a major challenge. Many factors including α-helicity, positive charge, peptide sequence, and staple composition and placement appear to affect cell uptake propensity. Recently, comprehensive analyses of several hundred stapled peptides in the Verdine and Walensky labs suggest that an optimal hydrophobic, positive charge, and helical content and proper staple placement are the key drivers of cellular uptake, whereas excess hydrophobicity and positive charge can trigger membrane lysis at elevated peptide dosing. See Chu, Q., et al., *Med. Chem. Commun.* 6, 111-119 (2015); *Nature Chemical Biology.* 12, 845-852 (2016). It is clear from these studies that many stapled peptides are either impermeable or poorly permeable to the cell membrane, which limits the application of stapled peptides as therapeutic agents.

Thus, there is a need in the art for improved stapled peptides having enhanced cellular permeability.

SUMMARY

The instant disclosure provides polypeptide conjugates for intracellular delivery of stapled peptides. The instant disclosure demonstrates that cyclic cell-penetrating peptides (cCPPs) can be used to confer consistent cell-permeability to stapled peptides. In addition, two methods to staple and conjugate alpha-helical peptides to cCPPs are provided.

In embodiments, the present disclosure provides for polypeptide conjugates comprising: a stapled peptide comprising a peptide and at least one staple which holds the peptide in an α-helical conformation, and at least one cyclic cell-penetrating peptide (cCPP) conjugated, directly or indirectly, to the stapled peptide. In embodiments, the cCPP of the present disclosure is conjugated directly or indirectly, to the staple. In further embodiments, the cCPP is conjugated, directly or indirectly, to the peptide. In still further embodiments, the cCPP is conjugated, directly or indirectly, to the N-terminus of the peptide. In other embodiments, the cCPP is conjugated, directly or indirectly, to the C-terminus of the peptide. In further embodiments, the cCPP is conjugated, directly or indirectly, to a side chain of an amino acid of the peptide. In the polypeptide conjugates of the instant invention, the staple may be selected from the group consisting of an amide, alkylene, N-alkylene, alkenylene, alkynylene, aryl, cycloalkyl, cycloalkenyl, cycloalkynyl, heterocyclyl, and heteroaryl, each of which are optionally substituted.

The polypeptide conjugates of the instant invention may further comprise a linker, which is covalently bound to an amino acid on the cCPP and either an amino acid on the peptide or the staple. In some embodiments, the linker is covalently bound to the stapled peptide through a disulfide bond. In further embodiments, the linker may be selected from the group consisting of at least one amino acid, alkylene, alkenylene, alkynylene, aryl, cycloalkyl, cycloalkenyl, cycloalkynyl, heterocyclyl, heteroaryl, ether, and combinations thereof, each of which are optionally substituted. In embodiments, the linker is capable of releasing the stapled peptide from the cCPP after the polypeptide conjugate enters the cytosol of a cell.

The polypeptide conjugates of the instant invention may have a structure according to Formula IA, IB, or IC:

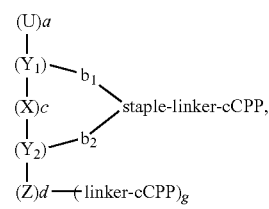

IA

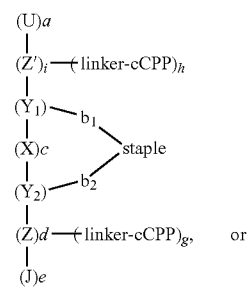

IB

-continued

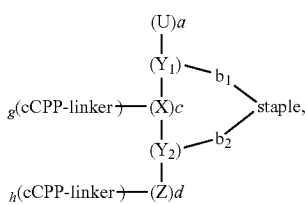

wherein:
  each of X and Z, at each instance, are independently selected from an amino acid;
  U, at each instance and when present, is independently selected from an amino acid;
  J, at each instance and when present, is independently selected from an amino acid;
  Z', at each instance and when present, is independent selected from an amino acid;
  a is a number in the range of from 0 to 500;
  c is at least 3;
  d is a number in the range of from 1 to 500;
  e is a number in the range of from 0 to 500;
  each of g and h are independently and at each instance 0 or 1, provided in at least one instance g is 1;
  i is a number in the range of from 0 to 100;
  $Y_1$ is an amino acid which has a side chain which forms a first bonding group ($b_1$) to the staple, and $Y_2$ is an amino acid which has a side chain which forms a second bonding group ($b_2$) to the staple.

In some embodiments, c is a number in the range of from 3 to 30. In some embodiments, c is 3, 6, or 10. In further embodiments, each of $b_1$ and $b_2$ are independently selected from a bond, aryl, thioether, disulfide, amide, ester, and ether.

In embodiments, J is absent, and Z may be either the N-terminus or the C-terminus of the peptide. In embodiments, J is present, e is 1, and J may be either the N-terminus or the C-terminus of the peptide. In further embodiments, J is present, e is 2 or more, and the terminal J is either the N-terminus or the C-terminus of the peptide. In other embodiments, U is absent, and Z' is either the N-terminus or the C-terminus of the peptide. In embodiments, U is present, a is 1, and U is either the N-terminus or the C-terminus of the peptide. In embodiments, U is present, a is 2 or more, and the terminal U is either the N-terminus or the C-terminus of the peptide.

In embodiments, the polypeptide conjugate of Formula IB may have the following structure:

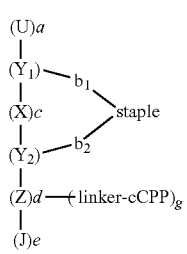

In embodiments, the polypeptide conjugate of Formula IC may have the following structure:

IC

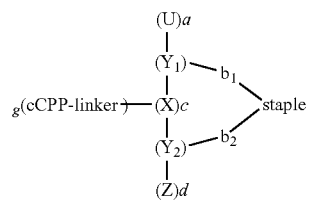

In embodiments, the cCPP may have a sequence comprising Formula II:

$$(AA_u)_m - AA_1 - AA_2 - AA_3 - AA_4 - (AA_z)_n \qquad \text{II}$$

wherein:
  each of $AA_1$, $AA_2$, $AA_3$, and $AA_4$, are independently selected from a D or L amino acid,
  each of $AA_u$ and $AA_z$, at each instance and when present, are independently selected from a D or L amino acid, and
  m and n are independently selected from a number from 0 to 6; and
wherein:
  at least two amino acids selected from the group consisting of $AA_u$, at each instance and when present, $AA_1$, $AA_2$, $AA_3$, $AA_4$, and $AA_z$, at each instance and when present, are independently arginine, and
  at least two of amino acids selected from the group consisting $AA_u$, at each instance and when present, $AA_1$, $AA_2$, $AA_3$, $AA_4$, and $AA_z$, at each instance and when present, are independently a hydrophobic amino acid.

In some embodiments, the cCPP has a sequence comprising any of Formula IIIA-D:

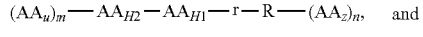

wherein:
  each of $AA_{H1}$ and $AA_{H2}$ are independently a D or L hydrophobic amino acid;
  at each instance and when present, each of $AA_u$ and $AA_z$ are independently a D or L amino acid; and
  m and n are independently selected from a number from 0 to 6.

The present disclosure also provides for a cell comprising the polypeptide conjugates disclosed herein.

The present disclosure additionally provides for a method for cellular delivery of a stapled peptide, the method comprising contacting a cell with the polypeptide conjugates disclosed herein.

Further, the present disclosure provides for a method for treating a patient in need thereof, comprising administering the polypeptide conjugates disclosed herein to the patient. The patient may have a disease or condition selected from a cancer, an inflammatory disease or condition, and an autoimmune disease or condition.

Additionally, the present disclosure provides for a method for making the polypeptide conjugates disclosed herein, the method comprising conjugating a stapled peptide and a cCPP. In other embodiments, the present disclosure provides for a method for making a polypeptide conjugates disclosed herein, the method comprising conjugating a peptide to at least one cCPP, and stapling the peptide.

The present disclosure also provides for a pharmaceutical composition comprising the polypeptide conjugates disclosed herein.

BRIEF DESCRIPTION OF THE DRAWINGS

FIG. 3A shows an on-resin stapling strategy, during which the helical peptide, the BBA staple/linker, and the cCPP are sequentially synthesized on resin. FIG. 3B shows a solution-phase stapling strategy, during which the BBA-derivatized cCPP and the helical peptide are synthesized separately and then stapled/conjugated in the solution phase.

DETAILED DESCRIPTION

Figure 1:
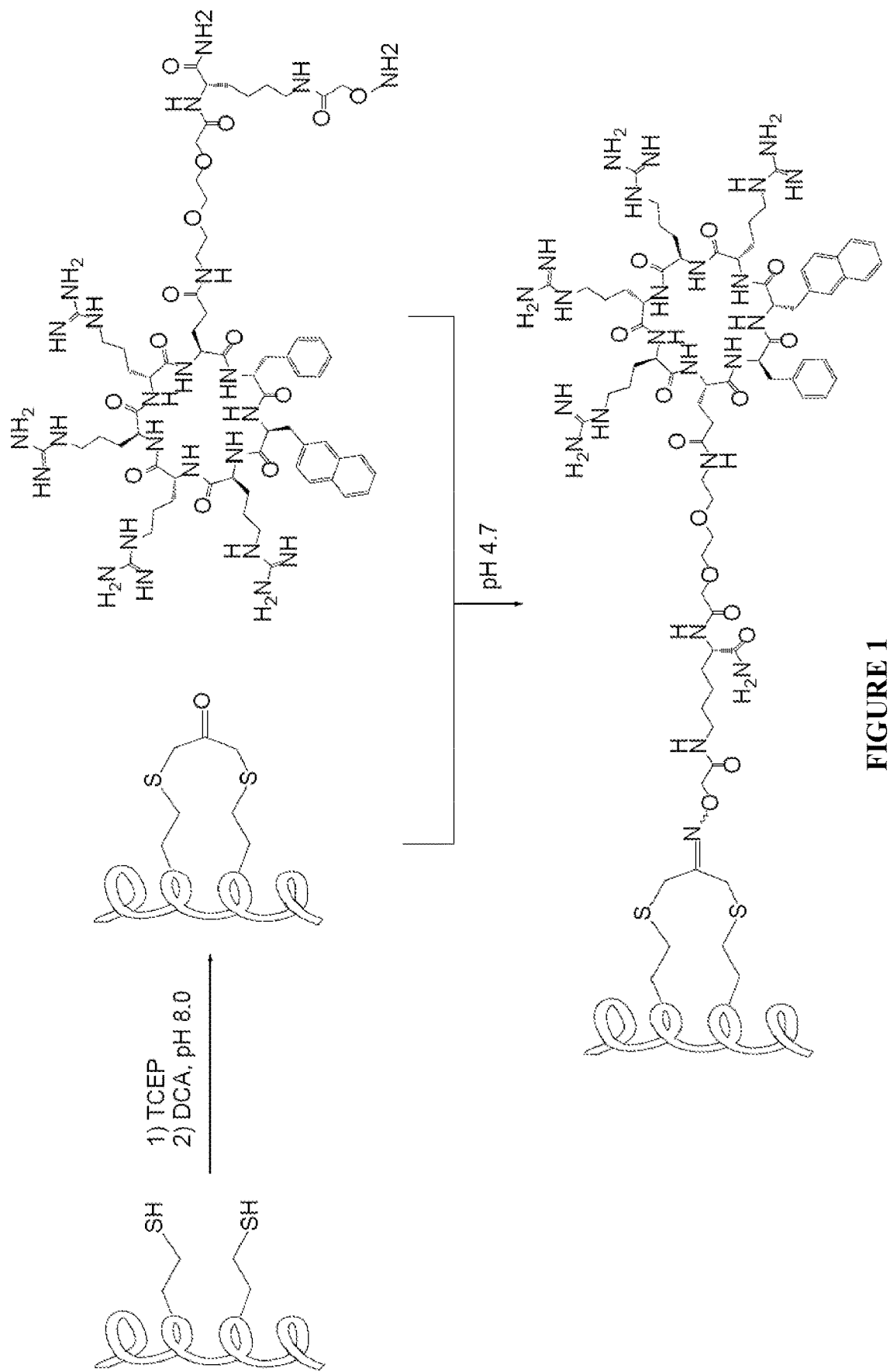
FIG. 1 is a schematic showing a strategy for synthesizing cCPP-stapled peptide conjugates with DCA as the staple.

When describing the present invention, all terms not defined herein have their common art-recognized meanings. Any term or expression not expressly defined herein shall have its commonly accepted definition understood by those skilled in the art. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

Definitions

"Amino acid" as used herein refers to the moiety that is present in the stapled peptide conjugates of the present disclosure. As used herein "hydrophobic amino acid" refers to an amino acid that has a hydrophobic group (e.g., an alkyl chain) on the side chain. Similarly, an "aromatic amino acid" refers to an amino acid having an aromatic group (e.g., a phenyl) on the side chain.

"Alkylene" or "alkylene chain" refers to a fully saturated, straight or branched divalent hydrocarbon chain radical, having from one to forty carbon atoms. Non-limiting examples of $C_2$-$C_{40}$ alkylene include ethylene, propylene, n-butylene, ethenylene, propenylene, n-butenylene, propynylene, n-butynylene, and the like. In some embodiments, the alkylene chain is attached, directly or indirectly, to the cCPP through a single bond and, directly or indirectly, to the staple or the peptide through a single bond. In some embodiments, the alkylene chain is independently attached, directly or indirectly, to side chain of a first amino acid of the peptide and a second amino acid of a peptide. Unless stated otherwise specifically in the specification, an alkylene chain can be optionally substituted as described herein.

"Alkenylene" or "alkenylene chain" refers to a straight or branched divalent hydrocarbon chain radical, having from two to forty carbon atoms, and having one or more carbon-carbon double bonds. Non-limiting examples of $C_2$-$C_{40}$ alkenylene include ethene, propene, butene, and the like. In some embodiments, the alkenylene chain is attached, directly or indirectly, to the cCPP through a single bond and, directly or indirectly, to the staple or the peptide through a single bond. In some embodiments, the alkenylene chain is independently attached, directly or indirectly, to side chain of a first amino acid of the peptide and a second amino acid of a peptide. Unless stated otherwise specifically in the specification, an alkenylene chain can be optionally substituted.

"Alkynylene" or "alkynylene chain" refers to a straight or branched divalent hydrocarbon chain radical, having from two to forty carbon atoms, and having one or more carbon-carbon triple bonds. Non-limiting examples of $C_2$-$C_{40}$ alkynylene include ethynylene, propargylene and the like. In some embodiments, the alkynylene chain is attached, directly or indirectly, to the cCPP through a single bond and, directly or indirectly, to the staple or the peptide through a single bond. In some embodiments, the alkynylene chain is independently attached, directly or indirectly, to side chain of a first amino acid of the peptide and, directly or indirectly, to a second amino acid of a peptide. Unless stated otherwise specifically in the specification, an alkynylene chain can be optionally substituted.

"Aryl" refers to a hydrocarbon ring system divalent radical comprising hydrogen, 6 to 40 carbon atoms and at least one aromatic ring. For purposes of this invention, the aryl divalent radical can be a monocyclic, bicyclic, tricyclic or tetracyclic ring system, which can include fused or bridged ring systems. Aryl divalent radicals include, but are not limited to, aryl divalent radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl divalent radical is attached, directly or indirectly, to the cCPP through a single bond and, directly or indirectly, to the staple or the peptide through a single bond. In some embodiments, the aryl is independently attached, directly or indirectly, to side chain of a first amino acid of the peptide and, directly or indirectly, to either the staple or a second amino acid of a peptide. Unless stated otherwise specifically in the specification, an aryl group can be optionally substituted.

"Cycloalkyl" refers to a stable non-aromatic monocyclic or polycyclic fully saturated hydrocarbon divalent radical having from 3 to 40 carbon atoms and at least one ring, wherein the ring consists solely of carbon and hydrogen atoms, which can include fused or bridged ring systems. Monocyclic cycloalkyl divalent radicals include, for example, cyclopropyl, cyclobutyl, cyclopentyl, cyclohexyl, cycloheptyl, and cyclooctyl. Polycyclic cycloalkyl divalent radicals include, for example, adamantyl, norbornyl, decalinyl, 7,7-dimethyl-bicyclo[2.2.1]heptanyl, and the like. In some embodiments, the cycloalkyl divalent radical is attached, directly or indirectly, to the cCPP through a single bond and, directly or indirectly, to the staple or the peptide through a single bond. In some embodiments, the cycloalkyl is independently attached, directly or indirectly, to side chain of a first amino acid of the peptide and, directly or indirectly, to either the staple or a second amino acid of a peptide. Unless otherwise stated specifically in the specification, a cycloalkyl group can be optionally substituted.

"Cycloalkenyl" refers to a stable non-aromatic monocyclic or polycyclic hydrocarbon divalent radical having from 3 to 40 carbon atoms, at least one ring having, and one or more carbon-carbon double bonds, wherein the ring consists solely of carbon and hydrogen atoms, which can include fused or bridged ring systems. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. In some embodiments, the cycloalkenyl divalent radical is attached, directly or indirectly, to the cCPP through a single bond and, directly or indirectly, to the staple or the peptide through a single bond. In some embodiments, the cycloalkenyl is independently attached, directly or indirectly, to side chain of a first amino acid of the peptide and, directly or indirectly, to either the staple or a second amino acid of a peptide. Unless otherwise stated specifically in the specification, a cycloalkenyl group can be optionally substituted.

"Cycloalkynyl" refers to a stable non-aromatic monocyclic or polycyclic hydrocarbon divalent radical having from 3 to 40 carbon atoms, at least one ring having, and one or more carbon-carbon triple bonds, wherein the ring consists solely of carbon and hydrogen atoms, which can include fused or bridged ring systems. Monocyclic cycloalkynyl radicals include, for example, cycloheptynyl, cyclooctynyl, and the like. In some embodiments, the cycloalkynyl divalent radical is attached, directly or indirectly, to the cCPP through a single bond and, directly or indirectly, to the staple or the peptide through a single bond. In some embodiments, the cycloalkynyl is independently attached, directly or indirectly, to side chain of a first amino acid of the peptide and, directly or indirectly, to either the staple or a second amino acid of a peptide. Unless otherwise stated specifically in the specification, a cycloalkynyl group can be optionally substituted.

"Heterocyclyl," "heterocyclic ring" or "heterocycle" refers to a stable 3- to 20-membered aromatic or non-aromatic ring divalent radical which consists of two to twelve carbon atoms and from one to six heteroatoms selected from the group consisting of nitrogen, oxygen and sulfur. Heterocyclycl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In some embodiments, the heterocyclyl divalent radical is attached, directly or indirectly, to the cCPP through a single bond and, directly or indirectly, to the staple or the peptide through a single bond. In some embodiments, the heterocyclyl is independently attached, directly or indirectly, to side chain of a first amino acid of the peptide and, directly or indirectly, to either the staple or a second amino acid of a peptide. Unless stated otherwise specifically in the specification, a heterocyclyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). In some embodiments, the heteroaryl divalent radical is attached, directly or indirectly, to the cCPP through a single bond and, directly or indirectly, to the staple or the peptide through a single bond. In some embodiments, the heteroaryl is independently attached, directly or indirectly, to side chain of a first amino acid of the peptide and, directly or indirectly, to either the staple or a second amino acid of a peptide. Unless stated otherwise specifically in the specification, a heteroaryl group can be optionally substituted.

The term "ether" used herein refers to a divalent radical moiety having a formula—$[(R_1)_m—O—(R_2)_n]_z$— wherein each of m, n, and z are independently selected from 1 to 40, and each of $R_1$ and $R_2$ are independently an alkylene, alkenylene, alkynylene, aryl, heteroaryl, cycloalkyl, cycloalkenyl, cycloalkynyl, or heterocyclyl group. In some embodiments, each of $R_1$ and $R_2$ are independently straight or branched alkylene groups. In particular embodiments, the ether has the formula—$[(CH_2)_m—O—(CH_2)_n]_z$— wherein each of m, n, and z are independently selected from 1 to 40. Examples include polyethylene glycol. The ether is attached, directly or indirectly, to the cCPP through a single bond and, directly or indirectly, to the staple or the peptide through a single bond. Unless stated otherwise specifically in the specification, the ether can be optionally substituted.

The term "N-alkylene" used herein refers to an alkylene divalent radical as defined above containing at least one nitrogen atom and where a point of attachment of the alkylene radical to the rest of the molecule is through the alkylene radical. In some embodiments, the point of attachment may optionally be the nitrogen atom. Unless stated otherwise specifically in the specification, a N-alkylene group can be optionally substituted.

As used herein, a "peptide" or "polypeptide" comprises a polymer of amino acid residues linked together by peptide (amide) bonds. The term(s), as used herein, refer to proteins, polypeptides, and peptide of any size, structure, or function. Typically, a peptide or polypeptide will be at least three amino acids long. A peptide or polypeptide may refer to an individual protein or a collection of proteins. The peptides of the instant invention may contain natural amino acids and/or non-natural amino acids (i.e., compounds that do not occur in nature but that can be incorporated into a polypeptide chain). Amino acid analogs as are known in the art may alternatively be employed. One or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof.

"Stapling" or "peptide stapling" is a strategy for constraining peptides typically in an alpha-helical conformation. Stapling is carried out by covalently linking the side-chains of two amino acids on a peptide, thereby forming a peptide macrocycle. Stapling generally involves introducing into a peptide at least two moieties capable of undergoing reaction to generate at least one cross-linker between the at least two moieties. The moieties may be two amino acids with appropriate side chains that are introduced into peptide sequence or the moieties may refer to chemical modifications of side chains. Stapling provides a constraint on a secondary structure, such as an alpha-helical structure. The length and geometry of the cross-linker can be optimized to improve the yield of the desired secondary structure content. The constraint provided can, for example, prevent the secondary structure from unfolding and/or can reinforce the shape of the secondary structure. A secondary structure that is prevented from unfolding is, for example, more stable.

A "stapled peptide" is a peptide comprising a staple (as described in detail herein). More specifically, a stapled peptide is a peptide in which one or more amino acids on the peptide are cross-linked to hold the peptide in a particular secondary structure, such as an alpha-helical conformation. The peptide of a stapled peptide comprises a selected number of natural or non-natural amino acids, and further comprises at least two moieties which undergo a reaction to generate at least one cross-linker between the at least two moieties, which modulates, for example, peptide stability.

A "stitched" peptide, is a stapled peptide comprising more than one (e.g., two, three, four, five, six, etc.) staple.

The term "substituted" used herein means any of the above groups (i.e., alkylene, alkenylene, alkynylene, aryl, carbocyclyl, cycloalkyl, cycloalkenyl, cycloalkynyl, heterocyclyl, heteroaryl, and/or ether) wherein at least one hydrogen atom is replaced by at least one non-hydrogen atom such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents. Further, those skilled in the art will recognize that "substituted" also encompasses instances in which one or more hydrogen atoms on any of the groups described herein are replaced by a functional group, and the functional group undergoes a reaction to form a covalent bond with the cCPP, the staple or the peptide. The reaction product is also considered a substituent. For example, in embodiments where the linker is conjugated to the staple, the staple may be appropriately substituted with a group that is capable of forming a bond to the linker. In some embodiments, said sample may be substituted with a carbonyl group (e.g., ketone or aldehyde), which forms an oxime upon coupling with the linker having a nucleophilic hydroxylamine (e.g., FIG. 1). In another example, any of the above groups can be substituted at a first position with a carboxylic acid (i.e., —C(=O)OH) which forms an amide bond with an appropriate amino acid CPP (e.g., lysine). Alternatively, or in addition, any of the above groups can be substituted with either an electrophilic group (e.g., —C(=O)H, —CO$_2$R$_g$, -halide, etc. where R$_g$ is a leaving group) which forms a bond with the N-terminus of the peptide or a nucleophilic group (—NH$_2$, —NHR$_g$, —OH, etc.) which forms a bond with the C-terminus of the peptide. In other embodiments, the group is substituted with a thiol group which forms a disulfide bond with a cysteine (or amino acid analog having a thiol group) in the peptide.

The term "radical" as used herein in reference to the above groups refer to an electron that participates in forming a bond to the moiety to which it is attached. For example, when the polypeptide conjugates disclosed herein comprise an ether linker which conjugates the cCCP to the stapled peptide. Prior to conjugation, the ether linker is defined as a divalent radical. To form the polypeptide conjugate one electron of the divalent radical is shared in a single bond to the cCCP, and the other electron is shared in a single bond with the stapled peptide.

The term "indirectly" when used in conjunction with attached or conjugated refers to a connection between groups (e.g., a cCPP and a stapled peptide), which is achieved using a linker. For example, a linker can be used to indirectly attach a cCPP to a staple, according to some embodiments.

Polypeptide Conjugates

The present disclosure, in various embodiments, provides for polypeptide conjugates comprising: a stapled peptide comprising a peptide and at least one staple which holds the peptide in an α-helical conformation, and at least one cyclic cell-penetrating peptide (cCPP) conjugated, directly or indirectly, to the stapled peptide. The cCPP can be conjugated to the stapled peptide at any suitable location. In some embodiments, the cCPP may be conjugated directly or indirectly, to the staple. In other embodiments, the cCPP may be conjugated, directly or indirectly, to the peptide at any appropriate position, including to a side chain of an amino acid in the peptide or to the N- or C-terminus of the peptide. Thus, in some embodiments, the cCPP may be conjugated, directly or indirectly, to the N-terminus of the peptide. In other embodiments, the cCPP may be conjugated, directly or indirectly, to the C-terminus of the peptide. In still other embodiments, the cCPP may be conjugated, directly or indirectly, to a side chain of an amino acid of the peptide.

The polypeptide conjugates of the instant invention may have a structure according to Formula IA, IB, or IC:

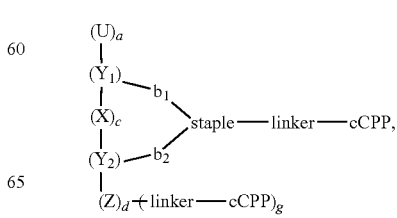

-continued

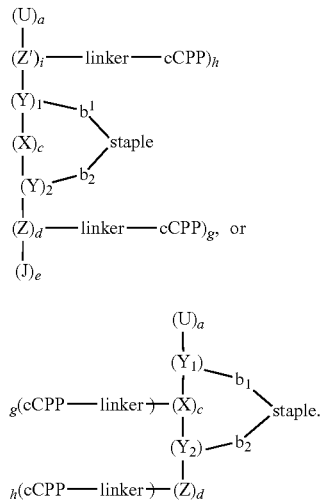

In some embodiments, each of X and Z, at each instance, are independently selected from an amino acid. In some embodiments, U, at each instance and when present, is independently selected from an amino acid. In some embodiments, J, at each instance and when present, is independently selected from an amino acid. In some embodiments, Z', at each instance and when present, is independent selected from an amino acid.

In some embodiments, d is a number in the range of from 1 to 500. In some embodiments, e is a number in the range of from 0 to 500. In some embodiments, i is a number in the range of from 0 to 100.

In some embodiments, each of g and h are independently and at each instance 0 or 1, provided in at least instance g is 1. Thus, in some embodiments, the peptide conjugates may comprise 1 cCPP-linker moiety (e.g., when d=1, g=1, and h=0 in Formula IB) or more than cCPP-linker moiety (e.g., when d=2, g=2, and h=0 in Formula IB; or when d=10, g=2, and h=0 in Formula IB).

In some embodiments, a is a number in the range of from 0 to 500. In some embodiments, c is at least 3. In some embodiments, c may be any number, 3 or greater, such that the staple (as described herein) is the same face of the alpha helix. In some embodiments, c is 3, 6, or 10. In further embodiments, each of $b_1$ and $b_2$ are independently selected from a bond, aryl, thioether, disulfide, amide, ester, and ether.

In some embodiments, $Y_1$ is an amino acid which has a side chain which forms a first bonding group ($b_1$) to the staple, and $Y_2$ is an amino acid which has a side chain which forms a second bonding group ($b_2$) to the staple.

The present disclosure envisions that the structures of Formula IA, IB, or IC can be interpreted as having an N to C or C to N orientation. That is, the top of the structure can be either the N-termini or the C-termini. Similarly, the bottom of the structure can be either the C-termini or the N-termini. In embodiments, J is absent, and Z may be either the N-terminus or the C-terminus of the peptide. In embodiments, J is present, e is 1, and J may be either the N-terminus or the C-terminus of the peptide. In further embodiments, J is present, e is 2 or more, and the terminal J is either the N-terminus or the C-terminus of the peptide. In other embodiments, U is absent, and Z' is either the N-terminus or the C-terminus of the peptide. In embodiments, U is present, a is 1, and U is either the N-terminus or the C-terminus of the peptide. In embodiments, U is present, a is 2 or more, and the terminal U is either the N-terminus or the C-terminus of the peptide.

In embodiments, the polypeptide conjugate of Formula IB may have the following structure:

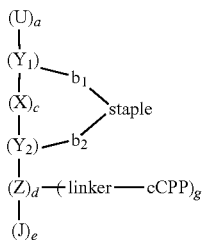

In embodiments, the polypeptide conjugate of Formula IC may have the following structure:

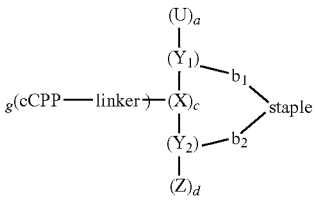

Peptide

The peptide for use in the polypeptide conjugates disclosed herein may be any peptide which contain at least one region having alpha-helical structure. The alpha-helix is a common secondary structure motif and plays an important functional role in many proteins. In embodiments, the peptide may be mostly in alpha-helical conformation, or the peptide may be part of a larger protein that includes one or more alpha-helical regions. As discussed above, the staple is appropriate located to substantially maintain the alpha-helical conformation.

The peptide may be naturally occurring, or it may be specifically designed to interact with a target (e.g., to inhibit protein-protein interactions). In some embodiments, the peptide may be derived from a naturally occurring peptide, which appropriate modifications to facilitate conjugation with the staple, linker, and/or cCPP, or combinations thereof. Thus, the amino acids in the peptide (each of X, Z, U, J, $Y_1$, $Y_2$, and Z', at each instance and when present) are independently selected from any natural or non-natural amino acid, and may independently refer to amino acids that naturally occur in the peptide or introduced into a peptide. The term "non-natural amino acid" refers to an organic compound that is analog of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Non-natural amino acids can also be the D-isomer of the natural amino acids. Examples of suitable amino acids include, but are not limited to, alanine, alloisoleucine, arginine, asparagine, aspartic acid, cysteine, glutamine, glutamic acid, glycine, histidine, isoleucine, leucine, lysine, methionine, naphthylalanine, phenylalanine, proline, pyroglutamic acid, serine, threonine, tryptophan, tyrosine, valine, 2,3-diaminopropionic acid a derivative, or combinations thereof. These, and others, are listed in the Table 1 along with their abbreviations used herein.

TABLE 1

Amino Acid Abbreviations

| Amino Acid | Abbreviations* L-amino acid | Abbreviations* D-amino acid |
|---|---|---|
| Alanine | Ala (A) | ala (a) |
| Allosoleucine | AIle | aile |
| Arginine | Arg (R) | arg (r) |
| Asparagine | Asn (N) | asn (n) |
| aspartic acid | Asp (D) | asp (d) |
| Cysteine | Cys (C) | cys (c) |
| Cyclohexylalanine | Cha | cha |
| 2,3-diaminopropionic acid | Dap | dap |
| 4-fluorophenylalanine | Fpa ($\Sigma$) | fpa |
| glutamic acid | Glu (E) | glu (e) |
| glutamine | Gln (Q) | gln (q) |
| glycine | Gly (G) | gly (g) |
| histidine | His (H) | his (h) |
| Homoproline (aka pipecolic acid) | Pip ($\Theta$) | pip ($\theta$) |
| isoleucine | Ile (I) | ile (i) |
| leucine | Leu (L) | leu (l) |
| lysine | Lys (K) | lys (k) |
| methionine | Met (M) | met (m) |
| naphthylalanine | Nal ($\Phi$) | nal ($\phi$) |
| norleucine | Nle ($\Omega$) | nle ($\omega$) |
| phenylalanine | Phe (F) | phe (f) |
| phenylglycine | Phg ($\Psi$) | Phg ($\psi$) |
| 4-(phosphonodifluorometh-yl)phenylalanine | F$_2$Pmp ($\Lambda$) | f$_2$pmp ($\lambda$) |
| proline | Pro (P) | pro (p) |
| sarcosine | Sar ($\Xi$) | sar ($\xi$) |
| Selenocysteine | Sec (U) | sec (u) |
| Serine | Ser (S) | ser (s) |
| Threonine | Thr (T) | thr (y) |
| Tyrosine | Tyr (Y) | tyr (y) |
| Tryptophan | Trp (W) | trp (w) |
| Valine | Val (V) | val (v) |
| 2,3-diaminopropionic acid | Dap | dap |

*single letter abbreviations: when shown in capital letters herein it indicates the L-amino acid form, when shown in lower case herein it indicates the D-amino acid.

In some embodiments, $Y_1$ is an amino acid which has a side chain that forms a first bonding group ($b_1$) to the staple, and $Y_2$ is an amino acid which has a side chain that forms a second bonding group ($b_2$) to the staple. Thus, precursors of each of $Y_1$ and $Y_2$ may independently be any amino acid having a side chain which is suitable, or can be modified to be suitable, to covalently bind the staple. Non-limiting examples of such amino acids include cysteine, glutamine, asparagine, and lysine, and analogs thereof (e.g., having additional hydrocarbons in the side chain, such as homocysteine).

Further examples of amino acid analogs which can be introduced to the peptides disclosed herein include those having an alkene side chain, an alkyne side chain or a nitrile side chain, as these side chains may be used to form the staple (e.g., during olefin or ring closing metathesis between two alkene-containing side chains) or to conjugate the staple. In still other embodiments, the precursor of $Y_1$ may be an amino acid having a side chain which is suitable for covalently bonding (e.g., forming an amide bond) to a side chain of the precursor of $Y_2$. In such embodiments, the "reaction product" between side chains of these amino acid analogs is the staple. For example, in certain embodiments, the precursor to $Y_1$ is lysine and the precursor to $Y_2$ is aspartate, and the amino group on the side chain of the $Y_1$ precursor reacts with the carboxyl group on the side chain of the $Y_2$ precursor to form an amide, which is the staple. As another example, the precursor to $Y_1$ may be an amino acid analog having a alkyne on the side chain and the precursor to $Y_2$ may be an amino acid having an azide on the side chain, and these groups react to form a triazole.

In particular, embodiments, the peptide can comprise one or more amino acids having a side chain comprising a thiol group (i.e., prior to conjugation to the linker, cCPP, and/or staple). The thiol group may be used to conjugate the cCPP, linker, and/or staple, by forming thioether, thioester, or disulfide. Non-limiting examples of amino acid analogs having a thiol group include cysteine, homocysteine, and any of the following amino acid analogs:

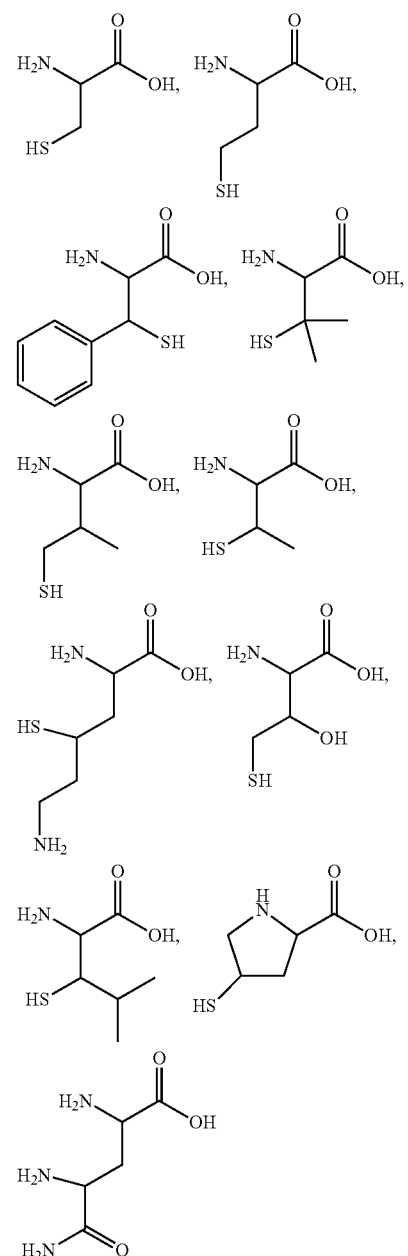

As previously stated, the above groups are precursors which allow for conjugation of a staple, linker, and/or a cCCP. Specifically, in order to conjugate the staple, linker, and/or a cCCP to the peptide, the hydrogen of the thiol in the above group is replaced by a bond to the staple, linker, or the cCPP.

One example of a peptide for use in the instant invention is a ligand of the MDM2 protein, such as the alpha-helical peptide Ac-LTFEHYWAQLTS (SEQ ID NO: 1) ("PDI"). This ligand is capable of binding to the MDM2 protein and therefore disrupting the interaction of MDM2 with p53. Peptides that disrupt the MDM2/p53 interaction might be useful for many applications, including, but not limited to, control of soft tissue sarcomas (which overexpresses MDM2 in the presence of wild type p53). These cancers may be held in check with small molecules that could intercept MDM2, thereby preventing suppression of p53. Peptides of the instant invention may be synthesized according to methods known to those of skill in the art. For example, the peptides may be synthesized using standard solid-phase peptide synthesis (SPPS).

Staple

The staple described herein stabilizes the bioactive, alpha-helical structure of the peptide, conferring, for example, protease resistance, cellular penetrance, and biological activity. The staple may be any synthetic brace capable of holding the peptide in an alpha-helical conformation. In embodiments, the staple reinforces the native alpha-helical conformation of the peptide, thereby maintaining binding affinity towards its protein targets.

Methods for peptide stapling are known to those of skill in the art. In some embodiments, peptide stapling may require generation of a polypeptide comprising two natural or non-natural amino acids (i.e., precursors of $Y_1$ and $Y_2$) bearing side chains with functional groups that are suitable for stapling. In certain embodiments, the sides of the precursors of $Y_1$ and $Y_2$ can react to form the staple. In other embodiments, the side precursors of $Y_1$ and $Y_2$ have side chains suitable for conjugating a staple (i.e., side chains with appropriate functional groups to bind the staple by forming of bonding groups, $b_1$ or $b_2$). In still other embodiments, the staple is formed by replacing an intramolecular hydrogen bond with a covalent bond, for example by replacing the hydrogen atom and carbonyl group on the opposing amino acids that participate in the intramolecular hydrogen bonding interaction with a group that crosslinks said opposing amino acids. Examples of such modifications are described in Joy, S. T. et al., *Chem. Commun (Camb.)* 52 (33), 5738-5741), and Zhao, H. et al. *Angew. Chem. Int. Ed.* 2016, 55, 12088-12093, each of which are herein incorporated by reference in its entirety.

The amino acids which form or are bound to the staple are typically spaced apart in the peptide chain such that their side chains are on substantially the same face of the folded peptide. Thus, for an alpha-helical peptide, the amino acid side chains are typically located on substantially the same face of the alpha helix. The distance between opposing amino acids on the same face of the peptide per turn of the helix is about 5.4 Å. Accordingly, in various embodiments, the staple is any appropriate moiety which holds these opposing amino acids at a distance of about 5.4 Å, thereby maintaining the alpha helical conformation. Thus, in embodiments, the staple may have a size in the range of from about 5 Å to about 6 Å, of from about 10 Å to about 12 Å, of from about 15 Å to about 17 Å, of from about 21 Å to about 23 Å, of from about 26 Å to about 28 Å, and of from about 31 Å to about 34 Å, inclusive of all values and subranges therebetween. In other embodiments, the staple may have a size of about 5 Å, about 5.5 Å, about 6 Å, about 10.5, about 11 Å, about 11.5 Å, about 12 Å, about 16.5 Å, about 17 Å, about 17.5 Å, about 22 Å, about 22.5 Å, about 23 Å, about 23.5 Å, about 25.5 Å, about 26 Å, about 26.5 Å, about 27 Å, about 27.5 Å, about 28 Å, about 28.5 Å, about 30.5 Å, about 31 Å, about 31.5 Å, about 32 Å, about 32.5 Å, about 33 Å, about 33.5 Å, about 34 Å, or about 34.5 Å.

For single turn stapling in an alpha helix, the amino acids to which the staple is conjugated are generally located at the i, i+4 positions. For double turn stapling in an alpha helix, the amino acids are generally located at the i, i+7 positions. For triple turn stapling in an alpha helix, the amino acids are generally located at the i, i+11 positions. In other embodiments, the polypeptide conjugates disclosed herein can comprise two or more staples (also referred to as stitched peptides). For example, the staple can be located at the i, i+4 positions and at the i+7, i+11.

In various embodiments, the number of amino acids between $Y_1$ and $Y_2$—i.e., "c" in Formula IA-IC—is an appropriate number of amino acids such that the staple is located on substantially the same face of the alpha helix. In embodiments, c is at least 3. In other embodiments, c is a number from 3 to 30. In still other embodiments, c is 3, 6, or 10.

In some embodiments, the staple is selected from the group consisting of alkylene, N-alkylene, alkenylene, alkynylene, aryl, cycloalkyl, cycloalkenyl, cycloalkynyl, heterocyclyl, and heteroaryl, each of which are optionally substituted. Non-limiting examples of staples include a lactam staple, a hydrocarbon staple, a CuAAC staple, a bis-thioether staple, a perfluorobenzene staple, and a thioether staple.

A number of alternative stapling methods are known to those in the art, each using a different form of macrocyclization chemistry and giving rise to stapled peptides with different bioactive properties. For example, the stapling may be one-component stapling. One-component stapling involves a direct bond-forming reaction between the side-chains of two amino acids. In some embodiments, the one-component stapling technique may comprise formation of an amide bond between to side chains of amino acids in the peptide. In some embodiments, the one-component stapling technique may comprise, for example, a ring-closing metathesis, a lactamization, a cycloaddition (such as the Cu(I)-catalyzed azide-alkyne cycloaddition (CuAAC, "click reaction")), a reversible reaction (such as formation of a disulfide bridge or an oxime linkage), or thioether formation. The stapling technique may alternatively be two-component stapling. Two-component stapling involves a bifunctional linker compound which forms a staple by reacting with two complementary native or non-native amino acids in the peptide of interest. Two-component stapling may employ, for example, a photoswitchable linker or a functionalized "double click" linker. When the staple is conjugated via click reaction, each of $b_1$ and $b_2$ are a triazole, which may be optionally substituted. That is, in some embodiments, the precursors to $Y_1$ and $Y_2$ may independently be an amino acid analog having an alkyne group on the side chain or an amino acid having an azide group on the side chain, and these groups react with a precursor to the staple having complementary alkyne and/or azide groups to form a triazole. The click reaction may also be used to produce a staple by two-component stapling, in which case the staple is the triazole and $b_1$ and $b_2$ are absent. Thus, $b_1$ and $b_2$ may independently be the bonding group formed when any of the above techniques are used to conjugate to staple to the peptide. In some embodiments, each of $b_1$ and $b_2$ are independently absent or selected from aryl (e.g., triazole), thioether, disulfide, amide, ester, and ether.

Additional examples of staples and stapling methods appropriate for use in the stapled peptides of the instant invention are described in Walensky, L. D., et al., *J. Med. Chem.*, 57, 6275-6288 (2014), Lau, Y. H., et al., *Chem. Soc. Rev.*, 00, 1-12 (2014), Joy, S. T. et al., *Chem. Commun (Camb.)* 52 (33), 5738-5741), and Zhao, H. et al. *Angew. Chem. Int. Ed.* 2016, 55, 12088-12093, each of which are incorporated herein by reference in their entireties.

Cyclic Cell-Penetrating Peptide (cCPP)

Cyclic cell-penetrating peptides allows for delivery of otherwise impermeable stapled peptides to be efficiently delivered to the cytosol and nucleus of cells. The cCPP of the polypeptide conjugates disclosed herein may be or include any amino sequence which facilitates cellular uptake of the polypeptide conjugates disclosed herein. Suitable cCPPs for use in the polypeptide conjugates and methods described herein can include naturally occurring sequences, modified sequences, and synthetic sequences. In embodiments, the total number of amino acids in the cCPP may be in the range of from 4 to about 20 amino acids, e.g., about 5, about 6, about 7, about 8, about 9, about 10, about 11, about 12, about 13, about 14, about 15, about 16, about 17, about 18, and about 19 amino acids, inclusive of all ranges and subranges therebetween. In some embodiments, the cCPPs disclosed herein comprise about 4 to about to about 13 amino acids. In particular embodiments, the CPPs disclosed herein comprise about 6 to about 10 amino acids, or about 6 to about 8 amino acids.

Each amino acid in the cCPP may independently be a natural or non-natural amino acid.

In some embodiments, the cCPPs may include any combination of at least two arginines and at least two hydrophobic amino acids. In some embodiments, the cCPPs may include any combination of two to three arginines and at least two hydrophobic amino acids.

In some embodiments, the cCPP used in polypeptide conjugates described herein has a structure comprising Formula 3:

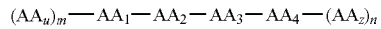
3 wherein:
each of $AA_1$, $AA_2$, $AA_3$, and $AA_4$, are independently selected from a D or L amino acid,
each of $AA_u$ and $AA_z$, at each instance and when present, are independently selected from a D or L amino acid, and
m and n are independently selected from a number from 0 to 6; and
wherein:
at least two of $AA_u$, when present, $AA_1$, $AA_2$, $AA_3$, $AA_4$, and $AA_z$, when present, are independently arginine, and
at least two of $AA_u$, when present, $AA_1$, $AA_2$, $AA_3$, $AA_4$, and $AA_z$, when present, are independently a hydrophobic amino acid.

In some embodiments, each hydrophobic amino acid is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, cyclohexylalanine, norleucine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, 3-(1,1'-biphenyl-4-yl)-alanine, tert-leucine, or nicotinoyl lysine, each of which is optionally substituted with one or more substituents. The structures of a few of these non-natural aromatic hydrophobic amino acids (prior to incorporation into the peptides disclosed herein) are provided below. In particular embodiments, each hydrophobic amino acid is independently a hydrophobic aromatic amino acid. In some embodiments, the aromatic hydrophobic amino acid is naphthylalanine, phenylglycine, homophenylalanine, phenylalanine, tryptophan, or tyrosine, each of which is optionally substituted with one or more substituents. In particular embodiments, the hydrophobic amino acid is piperidine-2-carboxylic acid, naphthylalanine, tryptophan, or phenylalanine, each of which is optionally substituted with one or more substituents.

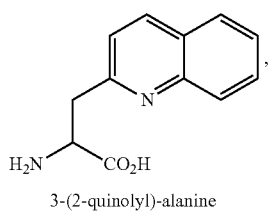
3-(2-quinolyl)-alanine

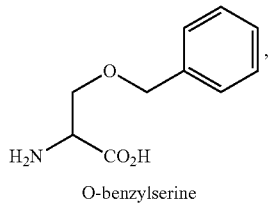
O-benzylserine

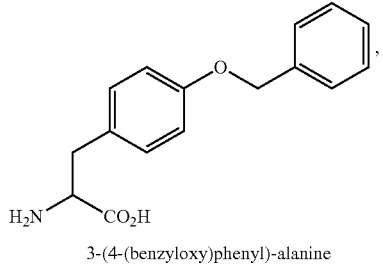
3-(4-(benzyloxy)phenyl)-alanine

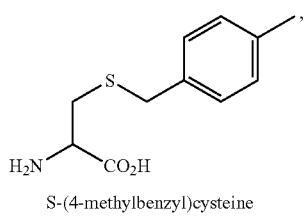
S-(4-methylbenzyl)cysteine

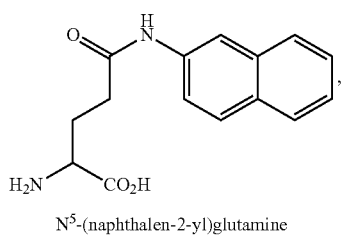
$N^5$-(naphthalen-2-yl)glutamine

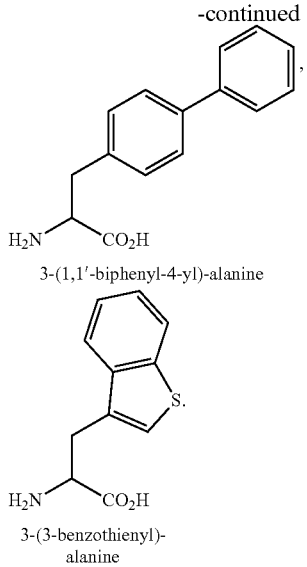

3-(1,1'-biphenyl-4-yl)-alanine 3-(3-benzothienyl)-alanine

The optional substituent can be any atom or group which does not significantly reduce the cytosolic delivery efficiency of the cCPP, e.g., a substituent that does not reduce relative cytosolic delivery efficiency to less than that of c(FΦRRRRQ). In some embodiments, the optional substituent can be a hydrophobic substituent or a hydrophilic substituent. In certain embodiments, the optional substituent is a hydrophobic substituent. In some embodiments, the substituent increases the solvent-accessible surface area (as defined herein) of the hydrophobic amino acid. In some embodiments, the substituent can be a halogen, alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio. In some embodiments, the substituent is one or more halogen atoms.

Amino acids having higher hydrophobicity values can be selected to improve cytosolic delivery efficiency of a cCPP relative to amino acids having a lower hydrophobicity value. In some embodiments, each hydrophobic amino acid independently has a hydrophobicity value which is greater than that of glycine. In other embodiments, each hydrophobic amino acid independently is a hydrophobic amino acid having a hydrophobicity value which is greater than that of alanine. In still other embodiments, each hydrophobic amino acid independently has a hydrophobicity value which is greater or equal to phenylalanine. Hydrophobicity may be measured using hydrophobicity scales known in the art. Table 2 below lists hydrophobicity values for various amino acids as reported by Eisenberg and Weiss (Proc. Natl. Acad. Sci. U.S.A. 1984; 81(1):140-144), Engleman, et al. (Ann. Rev. of Biophys. Biophys. Chem. 1986; 1986(15):321-53), Kyte and Doolittle (J. Mol. Biol. 1982; 157(1):105-132), Hoop and Woods (Proc. Natl. Acad. Sci. U. S. A 1981; 78(6):3824-3828), and Janin (Nature. 1979; 277(5696):491-492), the entirety of each of which is herein incorporated by reference in its entirety. In particular embodiments, hydrophobicity is measured using the hydrophobicity scale reported in Engleman, et al.

TABLE 2

| Amino Acid | Group | Eisenberg and Weiss | Engleman et al. | Kyrie and Doolittle | Hoop and Woods | Janin |
| --- | --- | --- | --- | --- | --- | --- |
| Ile | Nonpolar | 0.73 | 3.1 | 4.5 | −1.8 | 0.7 |
| Phe | Nonpolar | 0.61 | 3.7 | 2.8 | −2.5 | 0.5 |
| Val | Nonpolar | 0.54 | 2.6 | 4.2 | −1.5 | 0.6 |
| Leu | Nonpolar | 0.53 | 2.8 | 3.8 | −1.8 | 0.5 |
| Trp | Nonpolar | 0.37 | 1.9 | −0.9 | −3.4 | 0.3 |
| Met | Nonpolar | 0.26 | 3.4 | 1.9 | −1.3 | 0.4 |
| Ala | Nonpolar | 0.25 | 1.6 | 1.8 | −0.5 | 0.3 |
| Gly | Nonpolar | 0.16 | 1.0 | −0.4 | 0.0 | 0.3 |
| Cys | Anti-Polar | 0.04 | 2.0 | 2.5 | −1.0 | 0.9 |
| Tyr | Anti-Polar | 0.02 | −0.7 | −1.3 | −2.3 | −0.4 |
| Pro | Nonpolar | −0.07 | −0.2 | −1.6 | 0.0 | −0.3 |
| Thr | Anti-Polar | −0.18 | 1.2 | −0.7 | −0.4 | −0.2 |
| Ser | Anti-Polar | −0.26 | 0.6 | −0.8 | 0.3 | −0.1 |
| His | Charged | −0.40 | −3.0 | −3.2 | −0.5 | −0.1 |
| Glu | Charged | −0.62 | −8.2 | −3.5 | 3.0 | −0.7 |
| Asn | Anti-Polar | −0.64 | −4.8 | −3.5 | 0.2 | −0.5 |
| Gln | Anti-Polar | −0.69 | −4.1 | −3.5 | 0.2 | −0.7 |
| Asp | Charged | −0.72 | −9.2 | −3.5 | 3.0 | −0.6 |
| Lys | Charged | −1.10 | −8.8 | −3.9 | 3.0 | −1.8 |
| Arg | Charged | −1.80 | −12.3 | −4.5 | 3.0 | −1.4 |

The chirality of the amino acids can be selected to improve cytosolic uptake efficiency. In some embodiments, at least two of the amino acids have the opposite chirality. In some embodiments, the at least two amino acids having the opposite chirality can be adjacent to each other. In some embodiments, at least three amino acids have alternating stereochemistry relative to each other. In some embodiments, the at least three amino acids having the alternating chirality relative to each other can be adjacent to each other. In some embodiments, at least two of the amino acids have the same chirality. In some embodiments, the at least two amino acids having the same chirality can be adjacent to each other. In some embodiments, at least two amino acids have the same chirality and at least two amino acids have the opposite chirality. In some embodiments, the at least two amino acids having the opposite chirality can be adjacent to the at least two amino acids having the same chirality. Accordingly, in some embodiments, adjacent amino acids in the cCPP can have any of the following sequences: D-L; L-D; D-L-L-D; L-D-D-L; L-D-L-L-D; D-L-D-D-L; D-L-L-D-L; or L-D-D-L-D.

In some embodiments, an arginine is adjacent to a hydrophobic amino acid. In some embodiments, the arginine has the same chirality as the hydrophobic amino acid. In some embodiments, at least two arginines are adjacent to each other. In still other embodiments, three arginines are adjacent to each other. In some embodiments, at least two hydrophobic amino acids are adjacent to each other. In other embodiments, at least three hydrophobic amino acids are adjacent to each other. In other embodiments, the cCPPs described herein comprise at least two consecutive hydrophobic amino acids and at least two consecutive arginines. In further embodiments, one hydrophobic amino acid is adjacent to one of the arginines. In still other embodiments, the cCPPs described herein comprise at least three consecutive hydrophobic amino acids and there consecutive arginines. In further embodiments, one hydrophobic amino acid is adjacent to one of the arginines. These various combinations of amino acids can have any arrangement of D and L amino acids, e.g., the sequences described above.

In some embodiments, any four adjacent amino acids in the cCPPs described herein (e.g., the cCPPs according to Formula 2) can have one of the following sequences: $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$, wherein each of $AA_{H1}$ and $AA_{H2}$ are independently a hydrophobic amino acid. Accordingly, in some embodiments, the cCPPs used in the polypeptide conjugates described herein have a structure according any of Formula 4A-D:

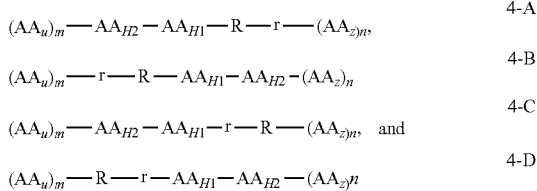

wherein:
each of $AA_{H1}$ and $AA_{H2}$ are independently a hydrophobic amino acid; at each instance and when present, each of $AA_u$ and $AA_z$ are independently any amino acid; and
m and n are independently selected from a number from 0 to 6.

In some embodiments, the total number of amino acids (including r, R, $AA_{H1}$, $AA_{H2}$), in the CPPs of Formula 4-A to 4-D are in the range of 6 to 10. In some embodiments, the total number of amino acids is 6. In some embodiments, the total number of amino acids is 7. In some embodiments, the total number of amino acids is 8. In some embodiments, the total number of amino acids is 9. In some embodiments, the total number of amino acids is 10.

In some embodiments, the sum of m and n is from 2 to 6. In some embodiments, the sum of m and n is 2. In some embodiments, the sum of m and n is 3. In some embodiments, the sum of m and n is 4. In some embodiments, the sum of m and n is 5. In some embodiments, the sum of m and n is 6. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, each hydrophobic amino acid is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, cyclohexylalanine, norleucine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, 3-(1,1'-biphenyl-4-yl)-alanine, tert-leucine, or nicotinoyl lysine, each of which is optionally substituted with one or more substituents. In particular embodiments, each hydrophobic amino acid is independently a hydrophobic aromatic amino acid. In some embodiments, the aromatic hydrophobic amino acid is naphthylalanine, phenylglycine, homophenylalanine, phenylalanine, tryptophan, or tyrosine, each of which is optionally substituted with one or more substituents. In particular embodiments, the hydrophobic amino acid is piperidine-2-carboxylic acid, naphthylalanine, tryptophan, or phenylalanine, each of which is optionally substituted with one or more substituents.

In some embodiments, each of $AA_{H1}$ and $AA_{H2}$ are independently a hydrophobic amino acid having a hydrophobicity value that is greater than that of glycine. In other embodiments, each of $AA_{H1}$ and $AA_{H2}$ are independently a hydrophobic amino acid having a hydrophobicity value that is greater than that of alanine. In still other embodiments, each of $AA_{H1}$ and $AA_{H2}$ are independently a hydrophobic amino acid having a hydrophobicity value which is greater than that of phenylalanine, e.g., as measured using the hydrophobicity scales described above, including Eisenberg and Weiss (Proc. Natl. Acad. Sci. U.S.A. 1984; 81(1):140-144), Engleman, et al. (Ann. Rev. of Biophys. Biophys. Chem. 1986; 1986(15):321-53), Kyte and Doolittle (J. Mol. Biol. 1982; 157(1):105-132), Hoop and Woods (Proc. Natl. Acad. Sci. U.S.A. 1981; 78(6):3824-3828), and Janin (Nature. 1979; 277(5696):491-492), (see Table 1 above). In particular embodiments, hydrophobicity is measured using the hydrophobicity scale reported in Engleman, et al.

The presence of a hydrophobic amino acid on the N- or C-terminal of a D-Arg or L-Arg, or a combination thereof, has also found to improve the cytosolic uptake of the cCPP (and the attached cargo). For example, in some embodiments, the cCPPs disclosed herein may include $AA_{H1}$-D-Arg or D-Arg-$AA_{H1}$. In other embodiments, the cCPPs disclosed herein may include $AA_{H1}$-L-Arg or L-Arg-$AA_{H1}$.

The size of the hydrophobic amino acid on the N- or C-terminal of the D-Arg or an L-Arg, or a combination thereof (i.e., $AA_{H1}$), may be selected to improve cytosolic delivery efficiency of the CPP. For example, a larger hydrophobic amino acid on the N- or C-terminal of a D-Arg or L-Arg, or a combination thereof, improves cytosolic delivery efficiency compared to an otherwise identical sequence having a smaller hydrophobic amino acid. The size of the hydrophobic amino acid can be measured in terms of molecular weight of the hydrophobic amino acid, the steric effects of the hydrophobic amino acid, the solvent-accessible surface area (SASA) of the side chain, or combinations thereof. In some embodiments, the size of the hydrophobic amino acid is measured in terms of the molecular weight of the hydrophobic amino acid, and the larger hydrophobic amino acid has a side chain with a molecular weight of at least about 90 g/mol, or at least about 130 g/mol, or at least about 141 g/mol. In other embodiments, the size of the amino acid is measured in terms of the SASA of the hydrophobic side chain, and the larger hydrophobic amino acid has a side chain with a SASA greater than alanine, or greater than glycine. In other embodiments, $AA_{H1}$ has a hydrophobic side chain with a SASA greater than or equal to about piperidine-2-carboxylic acid, greater than or equal to about tryptophan, greater than or equal to about phenylalanine, or equal to or greater than about naphthylalanine. In some embodiments, $AA_{H1}$ has a side chain side with a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, $AA_{H2}$ has a side chain side with a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, the side chains of $AA_{H1}$ and $AA_{H2}$ have a combined SASA of at least about 350 Å$^2$, at least about 360 Å$^2$, at least about 370 Å$^2$, at least about 380 Å$_2$, at least about 390 Å$^2$, at least about 400 Å$^2$, at least about 410 Å$^2$, at least about 420 Å$^2$, at least about 430 Å$^2$, at least about 440 Å$^2$, at least about 450 Å$^2$, at least about 460 Å$^2$, at least about 470 Å$^2$, at least about 480 Å$^2$, at least about 490 Å$^2$, greater than about 500 Å², at least about 510 Å², at least about 520 Å², at least about 530 Å², at least about 540 Å², at least about 550 Å², at least about 560 Å², at least about 570 Å², at least about 580 Å², at least about 590 Å², at least about 600 Å², at least about 610 Å², at least about 620 Å², at least about 630 Å², at least about 640 Å², greater than about 650 Å², at least about 660 Å², at least about 670 Å², at least about 680 Å², at least about 690 Å², or at least about 700 Å². In some embodiments, $AA_{H2}$ is a hydrophobic amino acid with a side chain having a SASA that is less than or equal to the SASA of the hydrophobic side chain of $AA_{H1}$. By way of example, and not by limitation, a cCPP having a Nal-Arg motif exhibits improved cytosolic delivery efficiency compared to an otherwise identical CPP having a Phe-Arg motif; a cCPP having a Phe-Nal-Arg motif exhibits improved cytosolic delivery efficiency compared to an otherwise identical cCPP having a Nal-Phe-Arg motif, and a phe-Nal-Arg motif exhibits improved cytosolic delivery efficiency compared to an otherwise identical cCPP having a nal-Phe-Arg motif.

As used herein, "hydrophobic surface area" or "SASA" refers to the surface area (reported as square Ångstroms; Å²) of an amino acid side chain that is accessible to a solvent. In particular embodiments, SASA is calculated using the 'rolling ball' algorithm developed by Shrake & Rupley (*J Mol Biol.* 79 (2): 351-71), which is herein incorporated by reference in its entirety for all purposes. This algorithm uses a "sphere" of solvent of a particular radius to probe the surface of the molecule. A typical value of the sphere is 1.4 Å, which approximates to the radius of a water molecule.

SASA values for certain side chains are shown below in Table 3. In certain embodiments, the SASA values described herein are based on the theoretical values listed in Table 3 below, as reported by Tien, et al. (PLOS ONE 8(11): e80635. https://doi.org/10.1371/journal.pone.0080635, which is herein incorporated by reference in its entirety for all purposes.

TABLE 3

SASA values for amino acid side chains.

| Residue | Theoretical | Empirical | Miller et al. (1987) | Rose et al. (1985) |
|---|---|---|---|---|
| Alanine | 129.0 | 121.0 | 113.0 | 118.1 |
| Arginine | 274.0 | 265.0 | 241.0 | 256.0 |
| Asparagine | 195.0 | 187.0 | 158.0 | 165.5 |
| Aspartate | 193.0 | 187.0 | 151.0 | 158.7 |
| Cysteine | 167.0 | 148.0 | 140.0 | 146.1 |
| Glutamate | 223.0 | 214.0 | 183.0 | 186.2 |
| Glutamine | 225.0 | 214.0 | 189.0 | 193.2 |
| Glycine | 104.0 | 97.0 | 85.0 | 88.1 |
| Histidine | 224.0 | 216.0 | 194.0 | 202.5 |
| Isoleucine | 197.0 | 195.0 | 182.0 | 181.0 |
| Leucine | 201.0 | 191.0 | 180.0 | 193.1 |
| Lysine | 236.0 | 230.0 | 211.0 | 225.8 |
| Methionine | 224.0 | 203.0 | 204.0 | 203.4 |
| Phenylalanine | 240.0 | 228.0 | 218.0 | 222.8 |
| Proline | 159.0 | 154.0 | 143.0 | 146.8 |
| Serine | 155.0 | 143.0 | 122.0 | 129.8 |
| Threonine | 172.0 | 163.0 | 146.0 | 152.5 |
| Tryptophan | 285.0 | 264.0 | 259.0 | 266.3 |
| Tyrosine | 263.0 | 255.0 | 229.0 | 236.8 |
| Valine | 174.0 | 165.0 | 160.0 | 164.5 |

In some embodiments, the cCPP does not include a hydrophobic amino acid on the N- and/or C-terminal of $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$. In alternative embodiments, the cCPP does not include a hydrophobic amino acid having a side chain which is larger (as described herein) than at least one of $AA_{H1}$ or $AA_{H2}$. In further embodiments, the cCPP does not include a hydrophobic amino acid with a side chain having a surface area greater than $AA_{H1}$. For example, in embodiments in which at least one of $AA_{H1}$ or $AA_{H2}$ is phenylalanine, the cCPP does not further include a naphthylalanine (although the cCPP include at least one hydrophobic amino acid which is smaller than $AA_{H1}$ and $AA_{H2}$, e.g., leucine). In still other embodiments, the cCPP does not include a naphthylalanine in addition to the hydrophobic amino acids in $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$.

The chirality of the amino acids (i.e., D or L amino acids) can be selected to improve cytosolic delivery efficiency of the cCPP (and the attached cargo as described below). In some embodiments, the hydrophobic amino acid on the N- or C-terminal of an arginine (e.g., $AA_{H1}$) has the same or opposite chirality as the adjacent arginine. In some embodiments, $AA_{H1}$ has the opposite chirality as the adjacent arginine. For example, when the arginine is D-arg (i.e. "r"), $AA_{H1}$ is a D-$AA_{H1}$, and when the arginine is L-Arg (i.e., "R"), $AA_{H1}$ is a L-$AA_{H1}$. Accordingly, in some embodiments, the cCPPs disclosed herein may include at least one of the following motifs: D-$AA_{H1}$-D-arg, D-arg-D-$AA_{H1}$, L-$AA_{H1}$-L-Arg, or L-Arg-L$AA_{H1}$. In particular embodiments, when arginine is D-arg, $AA_H$ can be D-nal, D-trp, or D-phe. In another non-limiting example, when arginine is L-Arg, $AA_H$ can be L-Nal, L-Trp, or L-Phe.

In some embodiments, the cCPPs described herein include three arginines. Accordingly, in some embodiments, the cCPPs described herein include one of the following sequences: $AA_{H2}$-$AA_{H1}$-R-r-R, $AA_{H2}$-$AA_{H1}$-R-r-r, $AA_{H2}$-$AA_{H1}$-r-R-R, $AA_{H2}$-$AA_{H1}$-r-R-r, R-R-r-$AA_{H1}$-$AA_{H2}$, r-R-r-$AA_{H1}$-$AA_{H2}$, r-r-R-$AA_{H1}$-$AA_{H2}$, or, R-r-R-$AA_{H1}$-$AA_{H2}$. In particular embodiments, the cCPPs have one of the following sequences $AA_{H2}$-$AA_{H1}$-R-r-R, $AA_{H2}$-$AA_{H1}$-r-R-r, r-R-r-$AA_{H1}$-$AA_{H2}$, or R-r-R-$AA_{H1}$-$AA_{H2}$. In some embodiments, the chirality of $AA_{H1}$ and $AA_{H2}$ can be selected to improve cytosolic uptake efficiency, e.g., as described above, where $AA_{H1}$ has the same chirality as the adjacent arginine, and $AA_{H1}$ and $AA_{H2}$ have the opposite chirality.

In some embodiments, the cCPPs described herein include three hydrophobic amino acids. Accordingly, in some embodiments, the cCPPs described herein include one of the following sequences: $AA_{H3}$-$AA_{H2}$-$AA_{H1}$-R-r, $AA_{H3}$-$AA_{H2}$-$AA_{H1}$-R-r, $AA_{H3}$-$AA_{H2}$-$AA_{H1}$-r-R, $AA_{H3}$-$AA_{H2}$-$AA_{H1}$-r-R, R-r-$AA_{H1}$-$AA_{H2}$-$AA_{H3}$, R-r-$AA_{H1}$-$AA_{H2}$-$AA_{H3}$, r-R-$AA_{H1}$-$AA_{H2}$-$AA_{H3}$, or, r-R-$AA_{H1}$-$AA_{H2}$-$AA_{H3}$, wherein $AA_{H3}$ is any hydrophobic amino acid described above, e.g., piperidine-2-carboxylic acid, naphthylalanine, tryptophan, or phenylalanine. In some embodiments, the chirality of $AA_{H1}$, $AA_{H2}$, and $AA_{H3}$ can be selected to improve cytosolic uptake efficiency, e.g., as described above, where $AA_{H1}$ has the same chirality as the adjacent arginine, and $AA_{H1}$ and $AA_{H2}$ have the opposite chirality. In other embodiments, the size of $AA_{H1}$, $AA_{H2}$, and $AA_{H3}$ can be selected to improve cytosolic uptake efficiency, e.g., as described above, where $AA_{H3}$ has a SAS of less than or equal to $AA_{H1}$ and/or $AA_{H2}$.

In some embodiments, $AA_{H1}$ and $AA_{H2}$ have the same or opposite chirality. In certain embodiments, $AA_{H1}$ and $AA_{H2}$ have the opposite chirality. Accordingly, in some embodiments, the cCPPs disclosed herein include at least one of the following sequences: D-$AA_{H2}$-L-$AA_{H1}$-R-r; L-$AA_{H2}$-D-$AA_{H1}$-r-R; R-r-D-$AA_{H1}$-L-$AA_{H2}$; or r-R-L-$AA_{H1}$-D-$AA_{H1}$, wherein each of D-$AA_{H1}$ and D-$AA_{H2}$ is a hydrophobic amino acid having a D configuration, and each of L-$AA_{H1}$ and L-AA$_{H2}$ is a hydrophobic amino acid having an L configuration. In some embodiments, each of D-AA$_{H1}$ and D-AA$_{H2}$ is independently selected from the group consisting of D-pip, D-nal, D-trp, and D-phe. In particular embodiments, D-AA$_{H1}$ or D-AA$_{H2}$ is D-nal. In other particular embodiments, D-AA$_{H1}$ is D-nal. In some embodiments, each of L-AA$_{H1}$ and L-AA$_{H2}$ is independently selected from the group consisting of L-Pip, L-Nal, L-Trp, and L-Phe. In particular embodiments, each of L-AA$_{H1}$ and L-AA$_{H2}$ is L-Nal.

As discussed above, the disclosure provides for various modifications to a cyclic peptide sequence, which may improve cytosolic delivery efficiency. In some embodiments, improved cytosolic uptake efficiency can be measured by comparing the cytosolic delivery efficiency of the cPP having the modified sequence to a proper control sequence. In some embodiments, the control sequence does not include a particular modification (e.g., matching chirality of R and AA$_{H1}$) but is otherwise identical to the modified sequence. In other embodiments, the control has the following sequence: cyclic(FΦRRRRQ)

As used herein cytosolic delivery efficiency refers to the ability of a cCPP to traverse a cell membrane and enter the cytosol. In embodiments, cytosolic delivery efficiency of the cCPP is not dependent on a receptor or a cell type. Cytosolic delivery efficiency can refer to absolute cytosolic delivery efficiency or relative cytosolic delivery efficiency.

Absolute cytosolic delivery efficiency is the ratio of cytosolic concentration of a cCPP (or a polypeptide conjugate) over the concentration of the cCPP (or the polypeptide conjugate) in the growth medium. Relative cytosolic delivery efficiency refers to the concentration of a cCPP in the cytosol compared to the concentration of a control cCPP in the cytosol. Quantification can be achieved by fluorescently labeling the cCPP (e.g., with a FITC dye) and measuring the fluorescence intensity using techniques well-known in the art.

In particular embodiments, relative cytosolic delivery efficiency is determined by comparing (i) the amount of a cCPP of the invention internalized by a cell type (e.g., HeLa cells) to (ii) the amount of the control cCPP internalized by the same cell type. To measure relative cytosolic delivery efficiency, the cell type may be incubated in the presence of a cell-penetrating peptide of the invention for a specified period of time (e.g., 30 minutes, 1 hour, 2 hours, etc.) after which the amount of the cCPP internalized by the cell is quantified using methods known in the art, e.g., fluorescence microscopy. Separately, the same concentration of the control cCPP is incubated in the presence of the cell type over the same period of time, and the amount of the control cCPP internalized by the cell is quantified.

In other embodiments, relative cytosolic delivery efficiency can be determined by measuring the IC$_{50}$ of a cCPP having a modified sequence for an intracellular target, and comparing the IC$_{50}$ of the cCPP having the modified sequence to a proper control sequence (as described herein).

In some embodiments, the relative cytosolic delivery efficiency of the cCPPs described herein in the range of from about 1% to about 1000% compared to, e.g., cyclo(FΦRRRRQ) or a linear cell-penetrating peptide sequence (such as HIV-TAT, a polyarginine sequence, and the like), e.g., about 1%, about 5%, about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, about 500%, about 510%, about 520%, about 530%, about 540%, about 550%, about 560%, about 570%, about 580%, or about 590%, about 600%, about 610%, about 620%, about 630%, about 640%, about 650%, about 660%, about 670%, about 680%, about 690%, about 700%, about 710%, about 720%, about 730%, about 740%, about 750%, about 760%, about 770%, about 780%, or about 790%, about 800%, about 810%, about 820%, about 830%, about 840%, about 850%, about 860%, about 870%, about 880%, about 890%, about 900%, about 910%, about 920%, about 930%, about 940%, about 950%, about 960%, about 970%, about 980%, or about 1000%, inclusive of all values and subranges therebetween.

In other embodiments, the absolute cytosolic delivery efficacy of from about 40% to about 100%, e.g., about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, inclusive of all values and subranges therebetween.

Non-limiting examples of suitable cyclic cell penetrating peptides are provided in Table 4.

TABLE 4

Examples of cyclic cell penetrating peptides.

| ID | cCPP Sequence |
|---|---|
| PCT 1 | cyclo(FΦRRRQ) |
| PCT 2 | cyclo(FΦRRRC) |
| PCT 3 | cyclo(FΦRRRU) |
| PCT 4 | cyclo(RRRΦFQ) |
| PCT 5 | cyclo(RRRRΦF) |
| PCT 6 | cyclo(FΦRRRR) |
| PCT 7 | cyclo(FΦrRrRq) |
| PCT 8 | cyclo(FΦrRrRQ) |
| PCT 9 | cyclo(FΦRRRRQ) |
| PCT 10 | cyclo(fΦRrRrQ) |
| PCT 11 | cyclo(RRFRΦRQ) |
| PCT 12 | cyclo(FRRRRΦQ) |
| PCT 13 | cyclo(rRFRΦRQ) |
| PCT 14 | cyclo(RRΦFRRQ) |
| PCT 15 | cyclo(CRRRRFWQ) (SEQ ID NO: 2, underlined portion only) |
| PCT 16 | cyclo(FfΦRrRrQ) |
| PCT 17 | cyclo(FFΦRRRRQ) |
| PCT 18 | cyclo(RFRFRΦRQ) |
| PCT 19 | cyclo(URRRRFWQ) (SEQ ID NO: 3, underlined portion only) |
| PCT 20 | cyclo(CRRRRFWQ) (SEQ ID NO: 4, underlined portion only) |
| PCT 21 | cyclo(FΦRRRRQK) |
| PCT 22 | cyclo(FΦRRRRQC) |
| PCT 23 | cyclo(fΦRrRrRQ) |
| PCT 24 | cyclo(FΦRRRRRQ) |
| PCT 25 | cyclo(RRRRΦFDΩC) |
| PCT 26 | cyclo(FΦRRR) |
| PCT 27 | cyclo(FWRRR) (SEQ ID NO: 5, underlined portion only) |
| PCT 28 | cyclo(RRRΦF) |
| PCT 29 | cyclo(RRRWF) (SEQ ID NO: 6, underlined portion only) |
| SAR 1 | cyclo(FΦRRRRQ) |
| SAR 19 | cyclo(FFRRRQ) (SEQ ID NO: 7, underlined portion only) |
| SAR 20 | cyclo(FFrRrQ) |
| SAR 21 | cyclo(FFRrRQ) |
| SAR 22 | cyclo(FRFRRQ) (SEQ ID NO: 8, underlined portion only) |
| SAR 23 | cyclo(FRRFRQ) (SEQ ID NO: 9, underlined portion only) |
| SAR 24 | cyclo(FRRRFQ) (SEQ ID NO: 10, underlined portion only) |
| SAR 25 | cyclo(GΦRRRQ) |
| SAR 26 | cyclo(FFFRAQ) (SEQ ID NO: 11, underlined portion only) |
| SAR 27 | cyclo(FFFRRQ) (SEQ ID NO: 12, underlined portion only) |
| SAR 28 | cyclo(FFRRRRQ) (SEQ ID NO: 13, underlined portion only) |
| SAR 29 | cyclo(FRRFRRQ) (SEQ ID NO: 14, underlined portion only) |

TABLE 4-continued

Examples of cyclic cell penetrating peptides.

| ID | cCPP Sequence |
|---|---|
| SAR 30 | cyclo(FRRRFRQ) (SEQ ID NO: 15, underlined portion only) |
| SAR 31 | cyclo(RFFRRRQ) (SEQ ID NO: 16, underlined portion only) |
| SAR 32 | cyclo(RFRFRRQ) (SEQ ID NO: 17, underlined portion only) |
| SAR 33 | cyclo(FRRRFRQ) (SEQ ID NO: 18, underlined portion only) |
| SAR 34 | cyclo(FFFRRRQ) (SEQ ID NO: 19, underlined portion only) |
| SAR 35 | cyclo(FFRRRFQ) (SEQ ID NO: 20, underlined portion only) |
| SAR 36 | cyclo(FRFFRRQ) (SEQ ID NO: 21, underlined portion only) |
| SAR 37 | cyclo(RRFFFRQ) (SEQ ID NO: 22, underlined portion only) |
| SAR 38 | cyclo(FFRRFRQ) (SEQ ID NO: 23, underlined portion only) |
| SAR 39 | cyclo(FFRRFRQ) (SEQ ID NO: 24, underlined portion only) |
| SAR 40 | cyclo(FRRFFRQ) (SEQ ID NO: 25, underlined portion only) |
| SAR 41 | cyclo(FRRFRFQ) (SEQ ID NO: 26, underlined portion only) |
| SAR 42 | cyclo(FRFRFRQ) (SEQ ID NO: 27, underlined portion only) |
| SAR 43 | cyclo(RFFRFRQ) (SEQ ID NO: 28, underlined portion only) |
| SAR 44 | cyclo(GΦRRRRQ) |
| SAR 45 | cyclo(FFFRRRRQ) (SEQ ID NO: 29, underlined portion only) |
| SAR 46 | cyclo(RFFRRRRQ) (SEQ ID NO: 30, underlined portion only) |
| SAR 47 | cyclo(RRFFRRRQ) (SEQ ID NO: 31, underlined portion only) |
| SAR 48 | cyclo(RFFFRRRQ) (SEQ ID NO: 32, underlined portion only) |
| SAR 49 | cyclo(RRFFFRRQ) (SEQ ID NO: 33, underlined portion only) |
| SAR 50 | cyclo(FFFRRRRQ) (SEQ ID NO: 34, underlined portion only) |
| SAR 51 | cyclo(FFRRRRFQ) (SEQ ID NO: 35, underlined portion only) |
| SAR 52 | cyclo(FRRFFRRQ) (SEQ ID NO: 36, underlined portion only) |
| SAR 53 | cyclo(FFFRRRRRQ) (SEQ ID NO: 37, underlined portion only) |
| SAR 54 | cyclo(FFFRRRRRRQ) (SEQ ID NO: 38, underlined portion only) |
| SAR 55 | cyclo(FΦRrRrQ) |
| SAR 56 | cyclo(XXRRRRQ) (SEQ ID NO: 39, underlined portion only) |
| SAR 57 | cyclo(FfFRrRQ) |
| SAR 58 | cyclo(fFfrRrQ) |
| SAR 59 | cyclo(fFfRrRQ) |
| SAR 60 | cyclo(FfFrRrQ) |
| SAR 61 | cyclo(fFΦRrRQ) |
| SAR 62 | cyclo(fΦfrRrQ) |
| SAR 63 | cyclo(ΦFfrRrQ) |
| SAR 64 | cyclo(FΦrRrQ) |
| SAR 65 | cyclo(fΦrRrQ) |
| SAR 66 | Ac-(Lys-fFRrRrD) |
| SAR 67 | Ac-(Dap-fFRrRrD) |
| SAR 68 | CWWRRRRC (S—S cyclized) |
| SAR 69 | CWWWRRRRC (S—S cyclized) |
| SAR 70 | CFWRRRRC (S—S cyclized) |
| SAR 71 | CWWWRRRC (S—S cyclized) |
| Pin1 15 | cyclo(Pip-Nal-Arg-Glu-arg-arg-glu) |
| Pin1 16 | cyclo(Pip-Nal-Arg-Arg-arg-arg-glu) |
| Pin1 17 | cyclo(Pip-Nal-Nal-Arg-arg-arg-glu) |
| Pin1 18 | cyclo(Pip-Nal-Nal-Arg-arg-arg-Glu) |
| Pin1 19 | cyclo(Pip-Nal-Phe-Arg-arg-arg-glu) |
| Pin1 20 | cyclo(Pip-Nal-Phe-Arg-arg-arg-Glu) |
| Pin1 21 | cyclo(Pip-Nal-phe-Arg-arg-arg-glu) |
| Pin1 22 | cyclo(Pip-Nal-phe-Arg-arg-arg-Glu) |
| Pin1 23 | cyclo(Pip-Nal-nal-Arg-arg-arg-glu) |
| Pin1 24 | cyclo(Pip-Nal-nal-Arg-arg-arg-glu) |
| Rev-13 | [Pim-RQRR-Nlys]GRRR[b] |
| hLF | KCFQWQRNMRKVRGPPVSC (cyclized) |
| cTat | [KrRrGrKkRrE][c] |
| cR10 | [KrRrRrRrRrRE][c] |
| L-50 | [RVRTRGKRRIRRpP] |
| L-51 | [RTRTRGKRRIRVpP] |
| [WR]4 | [WRWRWRWR] |
| MCoTI-II | [GGVCPKILKKCRRDSDCPGACICRGNGYCGSGSD] |
| Rotstein et al. Chem. Eur. J. 2011 | [P-Cha-r-Cha-r-Cha-r-Cha-r-G][d] |
| Lian et al. J. Am. Chem. Soc. 2014 | Tm(SvP-F₂Pmp-H)-Dap-(FΦRRRR-Dap)][f] |
| Lian et al. J. Am. Chem. Soc. 2014 | [Tm(a-Sar-D-pThr-Pip-ΦRAa)-Dap-(FΦRRR-Dap)][f] |
| IA8b | [CRRSRRGCGRRSRRCG][g] |
| Dod-[R5] | [K(Dod)RRRR] |
| LK-3 | LKKLCKLLKKLCKLAG / LKKLCKLLKKLCKLAG |
| | RRRR-[KRRRE][e] |
| | RRR-[KRRRRE][e] |
| | RR-[KRRRRRE][e] |
| | R-[KRRRRRRE][e] |
| [CR]4 | [CRCRCRCR] |
| cyc3 | [Pra-LRKRLRKFRN-AzK][h] |
| PMB | T-Dap-[Dap-Dap-f-L-Dap-Dap-T] |
| GPMB | T-Agp-[Dap-Agp-f-L-Agp-Agp-T] |
| cCPP1 | cyclo(FΦRRRRQ) |
| cCPP12 | cyclo(FfΦRrRrQ) |
| cCPP9 | cyclo(fΦRrRrQ) |
| cCPP11 | cyclo(fΦRrRrRQ) |
| cCPP18 | cyclo(FΦrRrRq) |
| cCPP13 | cyclo(FΦrRrRQ) |
| cCPP6 | cyclo(FΦRRRRRQ) |
| cCPP3 | cyclo(RRFRΦRQ) |
| cCPP7 | cyclo(FFΦRRRRQ) |
| cCPP8 | cyclo(RFRFRΦRQ) |
| cCPP5 | cyclo(FΦRRRQ) |
| cCPP4 | cyclo(FRRRRΦQ) |
| cCPP10 | cyclo(rRFRΦRQ) |
| cCPP2 | cyclo(RRΦFRRQ) |

Φ, L-2-naphthylalanine; Pim, pimelic acid; Nlys, lysine peptoid residue; D-pThr, D-phosphothreonine; Pip, L-piperidine-2-carboxylic acid; Cha, L-3-cyclohexyl-alanine; Tm, trimesic acid; Dap, L-2,3-diaminopropionic acid; Sar, sarcosine; F₂Pmp, L-difluorophosphonomethyl phenylalanine; Dod, dodecanoyl; Pra, L-propargylglycine; AzK, L-6-Azido-2-amino-hexanoic; Agp, L-2-amino-3-guanidinylpropionic acid;
[b]Cyclization between Pim and Nlys;
[c]Cyclization between Lys and Glu;
[d]Macrocyclization by multicomponent reaction with aziridine aldehyde and isocyanide;
[e]Cyclization between the main-chain of Gln residue;
[f]N-terminal amine and side chains of two Dap residues bicyclized with Tm;
[g]Three Cys side chains bicyclized with tris(bromomethyl)benzene;
[h]Cyclization by the click reaction between Pra and Azk.

Additionally, the cCPP used in the polypeptide conjugates and methods described herein can include any sequence disclosed in: U.S. application Ser. No. 15/312,878 (US Pub. No. US 2017/0190743 A1); U.S. application Ser. No. 15/360,719 (US Pub. No. US 2017/0355730); PCT/US2017/060881 (and the resulting US publication); and PCT/US2017/062951 (and the resulting US publication), each of which is incorporated by reference in its entirety for all purposes.

In some embodiments, the cCPP improves the cytosolic delivery efficiency by about 1.1 fold to about 30 fold, compared to a linear cell-penetrating peptide sequence (such as HIV-TAT, polyarginine and the like), e.g., about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 10, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20, about 20.5, about 21.0, about 21.5, about 22.0, about 22.5, about 23.0, about 23.5, about 24.0, about 24.5, about 25.0, about 25.5, about 26.0, about 26.5, about 27.0, about 27.5, about 28.0, about 28.5, about 29.0, or about 29.5 fold, inclusive of all values and subranges therebetween.

Linker

As discussed above, the cCPP may be directly conjugated to the stapled peptide (e.g., by a covalent bond between a side chain of an amino acid on the cCPP and an appropriate group on the stapled peptide) or a linker may be used to conjugate the cCPP to the stapled peptide. As used herein, "linker" refers to a moiety that forms a covalent bond between the two or more components of the polypeptide conjugates disclosed herein (e.g., a cCPP and a stapled peptide via the staple or the peptide).

In various embodiments, the linker is covalently bound to an amino acid on the cCPP and either an amino acid on the peptide or the staple. The linker may be any moiety which conjugates two or more of the cCPP moiety, the peptide, and the staple. In some embodiments, the linker can be an amino acid. In other embodiments, the precursor to the linker can be any appropriate molecule which is capable of forming two or more bonds with amino acids in the cCPP, the peptide, the staple, and combinations thereof. Thus, in various embodiments, the precursor of the linker has two or more functional groups, each of which are capable of forming a covalent bond to at least two of the cCPP moiety, the peptide, and the staple. For example, the linker can be covalently bound to the N-terminus, C-terminus, or side chain, or combinations thereof, of any amino acid in the cCPP moiety, the peptide, or the staple. In particular embodiments, the linker forms a covalent bond between the cCPP and peptide.

In some embodiments, the linker is selected from the group consisting of at least one amino acid, alkylene, alkenylene, alkynylene, aryl, cycloalkyl, cycloalkenyl, cycloalkynyl, heterocyclyl, heteroaryl, ether, each of which can be optionally substituted as defined above. Non-limiting examples of linkers include polyethylene glycol, optionally conjugated to a lysine residue.

In some embodiments, the linker is covalently bound to the N or C-terminus of an amino acid on the stapled peptide, or to a side chain of glutamine, asparagine, or lysine, or a modified side chain of glutamine or asparagine (e.g., a reduced side chain having an amino group), on the cCPP, peptide, or staple. In particular embodiments, the linker forms a bond with the side chain of glutamine on the cCPP. In other particular embodiments, the linker described herein has a structure of L-1 or L-2:

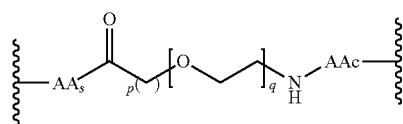

L-1

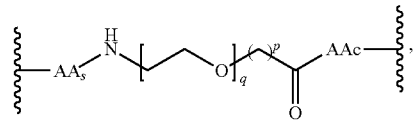

L-2 wherein

AA$_s$ is a side chain or terminus of an amino acid on the peptide or staple;

AA$_c$ is a side chain or terminus of an amino acid of the cCPP;

p is an integer from 0 to 10; and q is an integer from 1 to 50.

In some embodiments, the linker is capable of releasing the stapled peptide from the cCPP after the polypeptide conjugate enters the cytosol of the cell. In some embodiments, the linker contains a group, or forms a group after binding to cCPP, peptide, staple, or a combination thereof, that is cleaved after cytosolic uptake of the polypeptide conjugate to thereby release the peptide. Non-limiting examples of physiologically cleavable linking group include carbonate, thiocarbonate, thioester, disulfide, sulfoxide, hydrazine, protease-cleavable dipeptide linker, and the like.

For example, in embodiments, the linker is covalently bound to the stapled peptide through a disulfide bond e.g., with the side chain of cysteine or cysteine analog located in the stapled peptide or the cCPP. In some embodiments, the disulfide bond is formed between a thiol group on a precursor of the linker, and the side chain of cysteine or an amino acid analog having a thiol group on the peptide, wherein the bond to hydrogen on each of the thiol groups is replaced by a bond to a sulfur atom. Non-limiting examples of amino acid analogs having a thiol group which can be used with the polypeptide conjugates disclosed herein are discussed above.

Methods of Treatment

As discussed above, the polypeptide conjugates described herein can be used to treat or prevent a disease, disorder, or condition in a patient in need thereof. In some embodiments, treatment refers to partial or complete alleviation, amelioration, relief, inhibition, delaying onset, reducing severity and/or incidence of the disease, disorder, or condition in the patient.

The terms, "improve," "increase," "reduce," "decrease," and the like, as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein.

The individual (also referred to as "patient") being treated is an individual (fetus, infant, child, adolescent, or adult human) having a disease, disorder, or condition, or having the potential to develop a disease, disorder, or condition.

In some embodiments, the individual is an individual who has been recently diagnosed with a disease, disorder or condition. Typically, early treatment (treatment commencing as soon as possible after diagnosis) is important to minimize the effects of the disease, disorder or condition and to maximize the benefits of treatment.

In some embodiments, the polypeptide conjugates may be used to treat an individual diagnosed with a cancer. The polypeptide conjugates of the instant invention may be used to treat, for example, the following cancers: brain tumors such as for example acoustic neurinoma, astrocytomas such as fibrillary, protoplasmic, gemistocytic, anaplastic, pilocytic astrocytomas, glioblastoma, gliosarcoma, pleomorphic xanthoastrocytoma, subependymal large-cell giant cell astrocytoma and desmoplastic infantile astrocytoma; brain lymphomas, brain metastases, hypophyseal tumor such as prolactinoma, hypophyseal incidentaloma, HGH (human growth hormone) producing adenoma and corticotropic adenoma, craniopharyngiomas, medulloblastoma, meningioma and oligodendroglioma; nerve tumors such as for example tumors of the vegetative nervous system such as neuroblastoma, ganglioneuroma, paraganglioma (pheochromocytoma, chromaffinoma) and *glomus*-caroticum tumor, tumors on the peripheral nervous system such as amputation neuroma, neurofibroma, neurinoma (neurilemmoma, Schwannoma) and malignant Schwannoma, as well as tumors of the central nervous system such as brain and bone marrow tumors; intestinal cancer such as for example carcinoma of the rectum, colon, anus and duodenum; eyelid tumors (basalioma or adenocarcinoma of the eyelid apparatus); retinoblastoma; carcinoma of the pancreas; carcinoma of the bladder; lung tumors (bronchial carcinoma—small-cell lung cancer (SCLC), non-small-cell lung cancer (NSCLC) such as for example spindle-cell plate epithelial carcinomas, adenocarcinomas (acinary, papillary, bronchiolo-alveolar) and large-cell bronchial carcinoma (giant cell carcinoma, clear-cell carcinoma)); breast cancer such as ductal, lobular, mucinous or tubular carcinoma, Paget's carcinoma; non-Hodgkin's lymphomas (B-lymphatic or T-lymphatic NHL) such as for example hair cell leukemia, Burkitt's lymphoma or mycosis fungoides; Hodgkin's disease; uterine cancer (corpus carcinoma or endometrial carcinoma); CUP syndrome (Cancer of Unknown Primary); ovarian cancer (ovarian carcinoma-mucinous or serous cystoma, endometriodal tumors, clear cell tumor, Brenner's tumor); gall bladder cancer; bile duct cancer such as for example Klatskin tumor; testicular cancer (germinal or non-germinal germ cell tumors); laryngeal cancer such as for example supra-glottal, glottal and subglottal tumors of the vocal cords; bone cancer such as for example osteochondroma, chondroma, chondroblastoma, chondromyxoid fibroma, chondrosarcoma, osteoma, osteoid osteoma, osteoblastoma, osteosarcoma, non-ossifying bone fibroma, osteofibroma, desmoplastic bone fibroma, bone fibrosarcoma, malignant fibrous histiocytoma, osteoclastoma or giant cell tumor, Ewing's sarcoma, and plasmocytoma, head and neck tumors (HNO tumors) such as for example tumors of the lips, and oral cavity (carcinoma of the lips, tongue, oral cavity), nasopharyngeal carcinoma (tumors of the nose, lymphoepithelioma), pharyngeal carcinoma, oropharyngeal carcinomas, carcinomas of the tonsils (tonsil malignant) and (base of the) tongue, hypopharyngeal carcinoma, laryngeal carcinoma (cancer of the larynx), tumors of the paranasal sinuses and nasal cavity, tumors of the salivary glands and ears; liver cell carcinoma (hepatocellular carcinoma (HCC); leukemias, such as for example acute leukemias such as acute lymphatic/lymphoblastic leukemia (ALL), acute myeloid leukemia (AML); chronic lymphatic leukemia (CLL), chronic myeloid leukemia (CML); stomach cancer (papillary, tubular or mucinous adenocarcinoma, adenosquamous, squamous or undifferentiated carcinoma; malignant melanomas such as for example superficially spreading (SSM), nodular (NMM), lentigo-maligna (LMM), acral-lentiginous (ALM) or amelanotic melanoma (AMM); renal cancer such as for example kidney cell carcinoma (hypernephroma or Grawitz's tumor); oesophageal cancer; penile cancer; prostate cancer; vaginal cancer or vaginal carcinoma; thyroid carcinomas such as for example papillary, follicular, medullary or anaplastic thyroid carcinoma; thymus carcinoma (thymoma); cancer of the urethra (carcinoma of the urethra, urothelial carcinoma) and cancer of the vulva.

In other embodiments, the polypeptide conjugates may be used to treat an inflammatory disease or disorder. The inflammatory disease or disorder may be a respiratory disease such as, for example, asthma or chronic obstructive pulmonary disease, a chronic degenerative disease such as rheumatoid arthritis, osteoarthritis or osteoporosis, a dermatological condition such as psoriasis, scleroderma, atopic dermatitis, ichthyosis, pemphigus, acne, skin aging or wrinkles, a chronic demyelinating disease such as multiple sclerosis; an inflammatory bowel disease such as ulcerative colitis or Crohn's disease; a dental disease such as periodontal disease or gingivitis; an inflammatory nail disease such as nail psoriasis; lichen planus, alopecia areata, systemic lupus erythematosus, diabetic nephropathy, lupus nephritis, IgA nephropathy or glomerulonephritis, graft versus host disease or an ophthalmic condition.

In other embodiments, the polypeptide conjugates are used to treat an autoimmune disease or condition. The autoimmune disease or condition may be insulin-dependent diabetes mellitus, multiple sclerosis, rheumatoid arthritis, autoimmune uveitis, primary biliary cirrhosis, myasthenia gravis, Sjogren's syndrome, pemphigus vulgaris, scleroderma, pernicious anemia, systemic lupus erythematosus, Grave's disease, inflammatory bowel disease, celiac disease, autoimmune thyroid disease such as Hashimoto's disease, autoimmune liver disease, Addison's disease, transplant rejection, graft vs. host disease, host vs. graft disease, ankylosing spondylitis, Chagas disease, chronic obstructive pulmonary disease, Crohns Disease, dermatomyositis, endometriosis, Goodpasture's syndrome, Guillain-Barre syndrome (GBS), hidradenitis suppurativa, Kawasaki disease, IgA nephropathy, idiopathic thrombocytopenic purpura, interstitial cystitis, mixed connective tissue disease, morphea, narcolepsy, neuromyotonia, psoriasis, psoriatic arthritis, polymyositis, relapsing polychondritis, sarcoidosis, schizophrenia, stiff person syndrome, temporal arteritis, ulcerative colitis, vasculitis, vitiligo, Wegener's granulomatosis, and combinations thereof.

The polypeptide conjugates provided herein can treat the above-described diseases, disorders, or conditions, for instance, by disrupting native protein-protein, protein-ligand, and/or protein-receptor interactions. For example, many biologically important protein/protein interactions, such as p53/MDM2 and Bcl-X1/Bak, are mediated by one protein donating a helix into a cleft of its helix-accepting partner. The interaction of p53 and MDM2 and mutations in the p53 gene have been identified in virtually half of all reported cancer cases (see, Shair Chem. & Biol. 1997, 4, 791, the entire contents of which are incorporated herein by reference). As stresses are imposed on a cell, p53 is believed to orchestrate a response that leads to either cell-cycle arrest and DNA repair, or programmed cell death. As well as mutations in the p53 gene that alter the function of the p53 protein directly, p53 can be altered by changes in MDM2. The MDM2 protein has been shown to bind to p53 and disrupt transcriptional activation by associating with the transactivation domain of p53. For example, an 11 amino-acid peptide derived from the transactivation domain of p53 forms an amphipathic alpha-helix of 2.5 turns that inserts into the MDM2 crevice.

Combination Therapies

In some embodiments, the polypeptide conjugates disclosed herein can be administered in combination with other therapies. The polypeptide conjugates can be administered simultaneous, sequentially, or at distinct time points as part of the same therapeutic regimen.

In some embodiments, the polypeptide conjugates disclosed herein are administered in combination with one or more chemotherapeutic agents. Chemotherapeutic agents which may be administered in combination with the compounds according to the invention include, without being restricted thereto, hormones, hormone analogues and anti-hormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, leuprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example gefitinib, lapatinib and trastuzumab); signal transduction inhibitors (e.g. imatinib and sorafenib); antimetabolites (e.g. antifolates such as methotrexate, pemetrexed and raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, mechlorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastim, interferon alpha, leucovorin, rituximab, procarbazine, levamisole, mesna, mitotane, pamidronate and porfimer.

Methods of Making

The polypeptide conjugates described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high-performance liquid chromatography (HPLC) or thin layer chromatography.

The disclosed compounds can be prepared by solid phase peptide synthesis wherein the amino acid α-N-terminal is protected by an acid or base protecting group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is particularly preferred for the synthesis of the disclosed compounds. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxy-carbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for aspartic acid and glutamic acid, benzyl and t-butyl and for cysteine, triphenylmethyl (trityl). In the solid phase peptide synthesis method, the α-C- terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. Solid supports for synthesis of α-C-terminal carboxy peptides is 4-hydroxymethylphenoxymethyl-copoly(styrene-1% divinylbenzene) or 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCl), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. One method for coupling to the deprotected 4 (2',4'-dimethoxyphenyl-Fmoc-aminomethyl) phenoxy-acetamidoethyl resin is O-benzotriazol-1-yl-N,N,N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer. In one example, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underderivatized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Methods of Administration

In vivo application of the disclosed polypeptide conjugates, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 2003/0032594 and 2002/0120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane: sebacic acid] in a 20:80 molar ratio (as used in GLIADEL); chondroitin; chitin; and chitosan.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

A number of embodiments of the invention have been described. Nevertheless, it will be understood that various modifications may be made without departing from the spirit and scope of the invention. Accordingly, other embodiments are within the scope of the following claims.

A number of publications, patents, and patent applications have been cited herein. Each of the cited publications, patents, and patent applications is hereby incorporated by reference in their entireties to the same extent as if each individual publication, patent or patent application was specifically and individually indicated as incorporated by reference in its entirety.

EXAMPLES

Example 1: Design Strategy and Synthesis of Cyclic CPP-Stapled Peptide Conjugates We chose to prepare the cCPP-stapled peptide conjugates by using a convergent synthesis method (FIG. 1). First, the cargo peptide was synthesized by standard solid-phase peptide synthesis (SPPS) with two homocysteine residues incorporated at the i and i+4 positions. After cleavage from the resin and side-chain deprotection, the peptide was treated with 1.5 equivalents of 1,3-dichloroacetone (DCA) to staple the peptide into an alpha-helical conformation. This stapling procedure also incorporates a ketone group into the stapled peptide for subsequent bioorthogonal conjugation with a cCPP. Next, a cCPP [e.g., CPP9] was synthesized by SPPS with a miniPEG-Lys(Mtt) linker attached to the Gln side chain. While still on resin, the Mtt group on the Lys side chain was selectively removed by treatment with 5% trifluoroacetic acid (TFA) and the exposed amine was acylated with a Boc-aminooxyacetyl moiety. Cleavage from resin and side chain deprotection with TFA gave CPP9 derivatized with a nucleophilic hydroxylamine group (aminoxy-CPP9; FIG. 1). Finally, the DCA-stapled peptide and aminoxy-CPP9 were conjugated in an aqueous solution (pH 4.7) through the formation of an oxime linkage. Note that the oxime formation results in two different stereoisomers (Z and E isomers).

Example 2: Cell-Permeable Stapled Peptides Against MDM2-p53 Interaction

As a proof of concept, we synthesized a cell-permeable stapled peptide against the MDM2-p53 interaction. Activation of the p53 protein protects the organism against the propagation of cells that carry damaged DNA with potentially oncogenic mutations. MDM2, a p53-specific E3 ubiquitin ligase, is the principal cellular antagonist of p53, acting to limit the p53 growth-suppressive function in cancer cells. MDM2 mediates the monoubiquitination and proteasomal degradation of p53. Disruption of the p53-MDM2 complex with small molecules and stapled peptides has been a popular approach to treating cancers with WT p53 proteins. See Wade, M., et al., Nature Reviews Cancer 13, 83-96 (2013).

Figure 5:
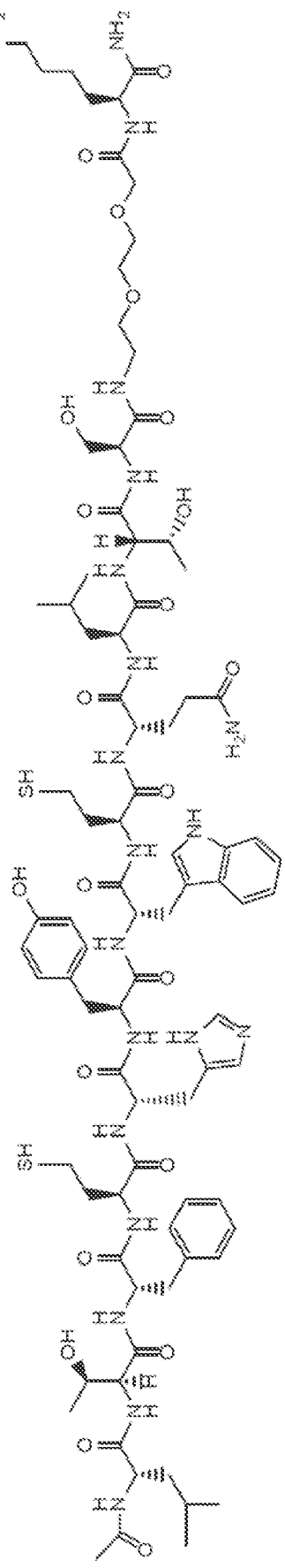
FIG. 5 shows the chemical structure of unstapled peptides 4 and 5 (stereoisomers), an HPLC chromatogram, and a low-resolution MALDI-TOF MS spectrum for the product (retention time=32 minutes).
Figure 5:
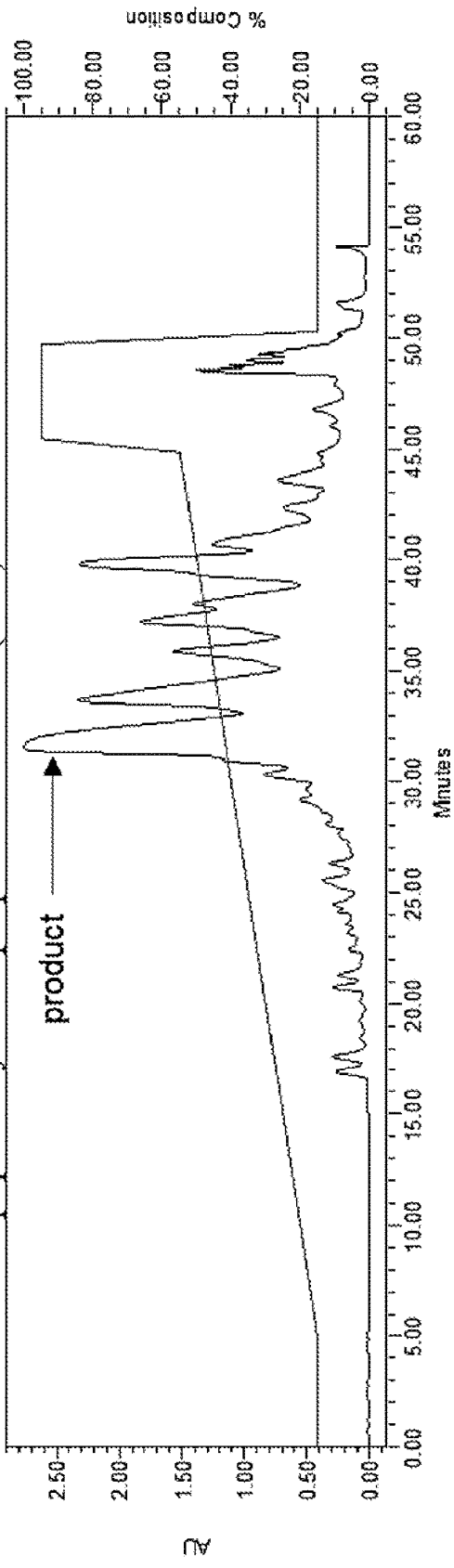
Figure 5:
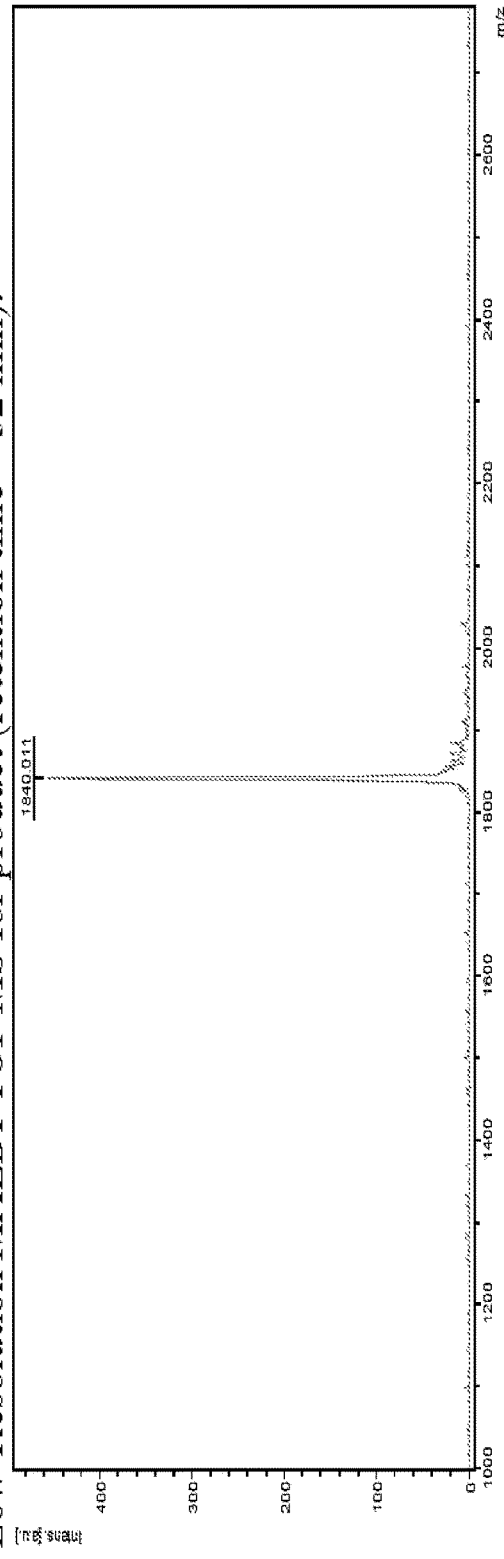
Figure 6:
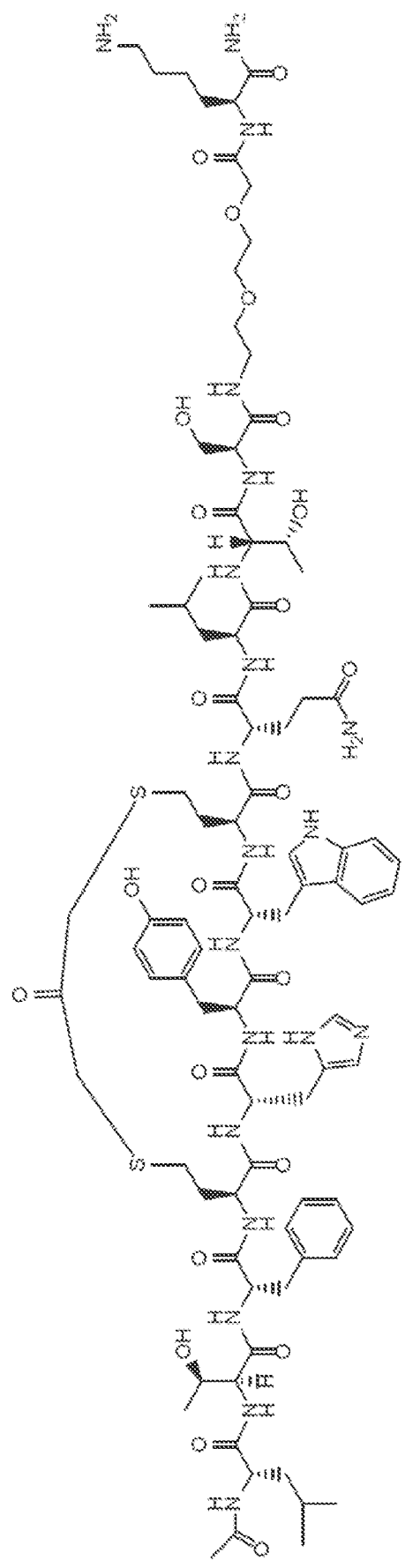
FIG. 6 shows the chemical structure of stapled peptide 3, an HPLC chromatogram, and a low-resolution MALDI-TOF MS spectrum for the product (retention time=30.5 minutes).
Figure 6:
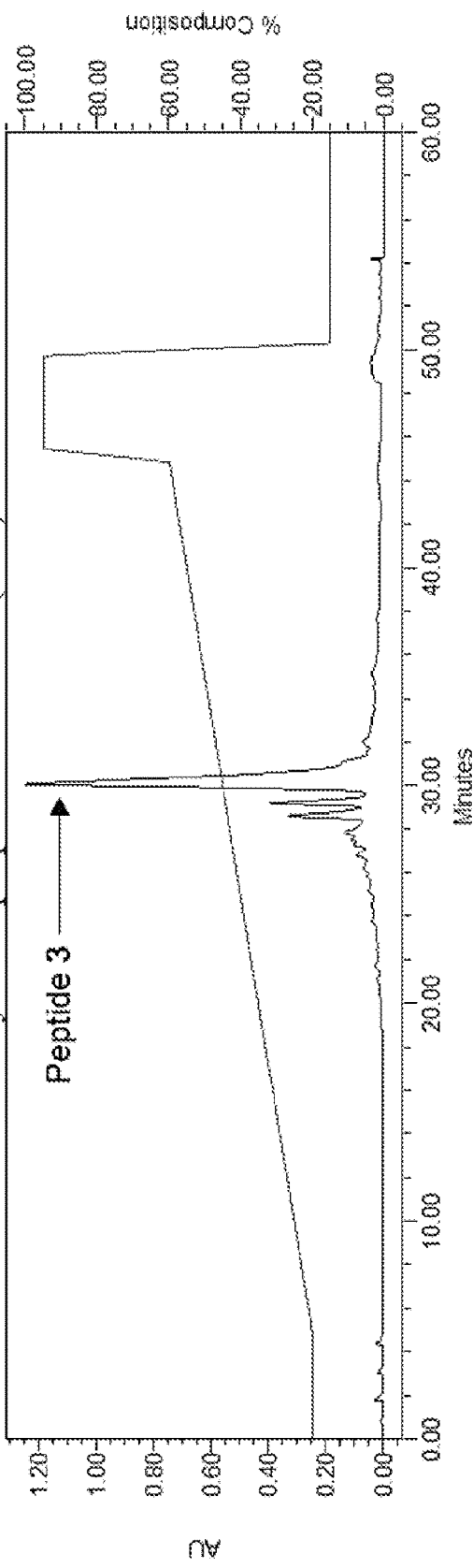
Figure 6:
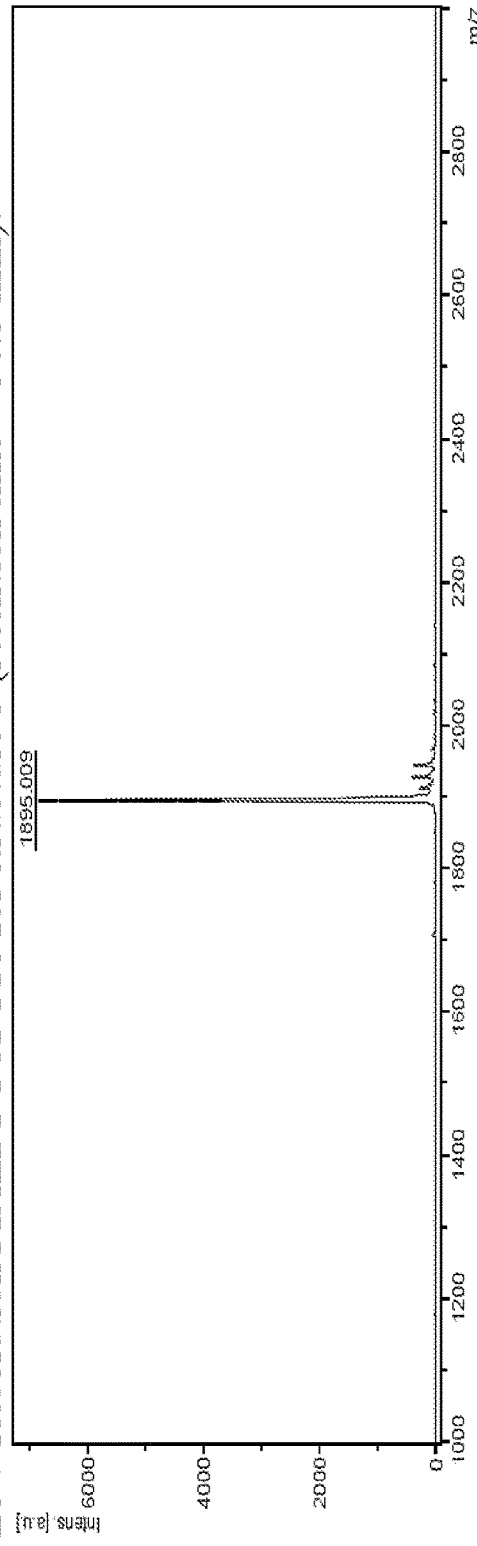
Figure 7:
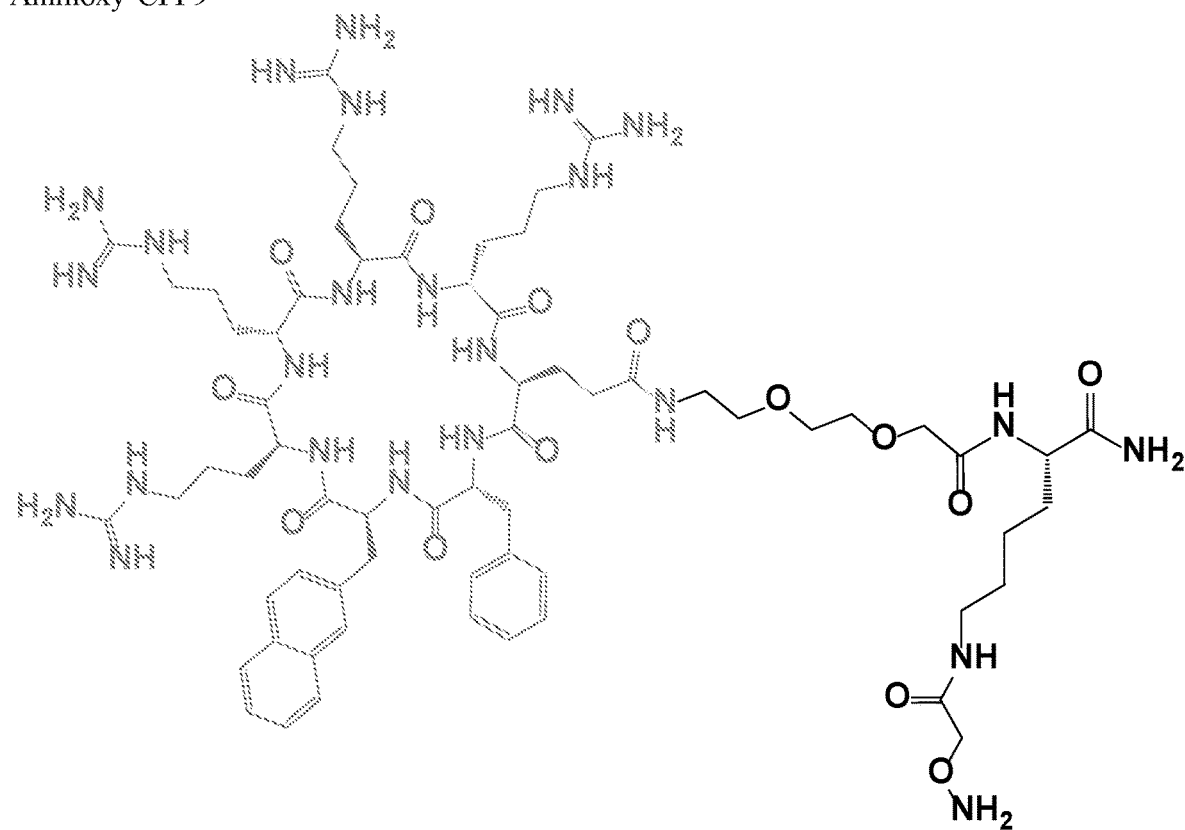
FIG. 7 shows the chemical structure of aminoxy-cCPP9, an HPLC chromatogram, and a low-resolution MALDI-TOF MS spectrum for aminoxy cCPP9 (retention time=22 min).
Figure 7:
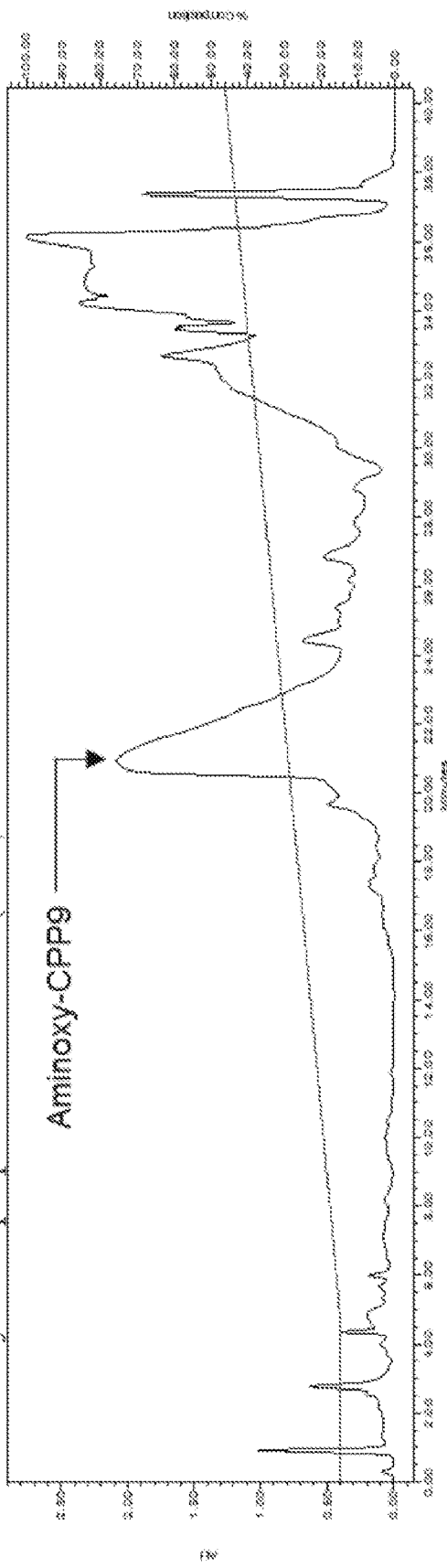
Figure 7:
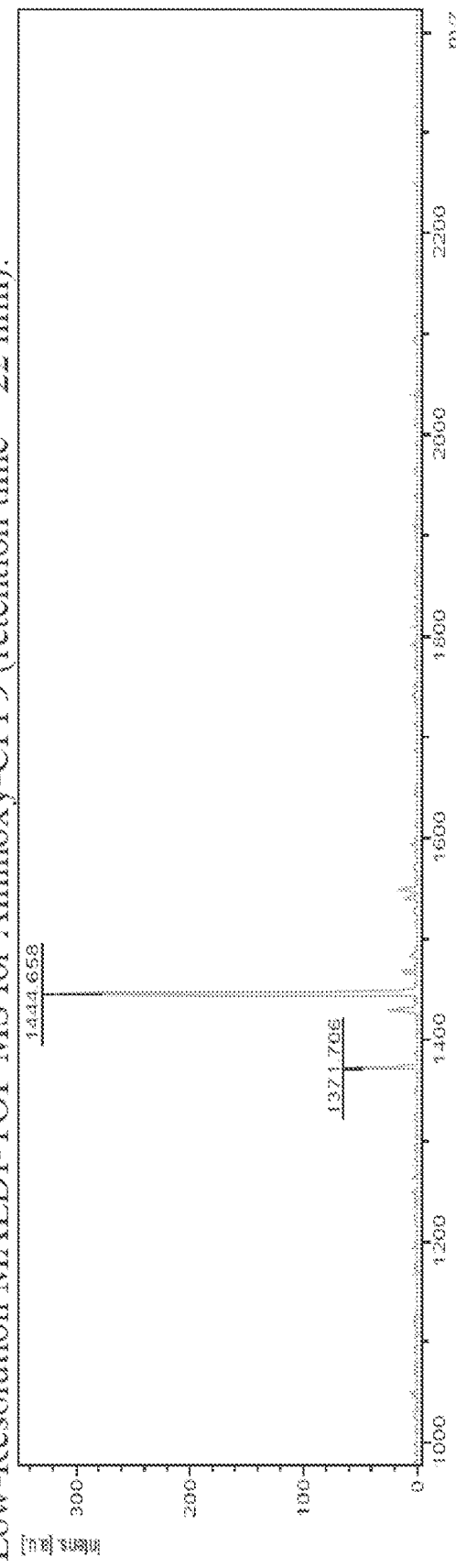
Figure 8A:
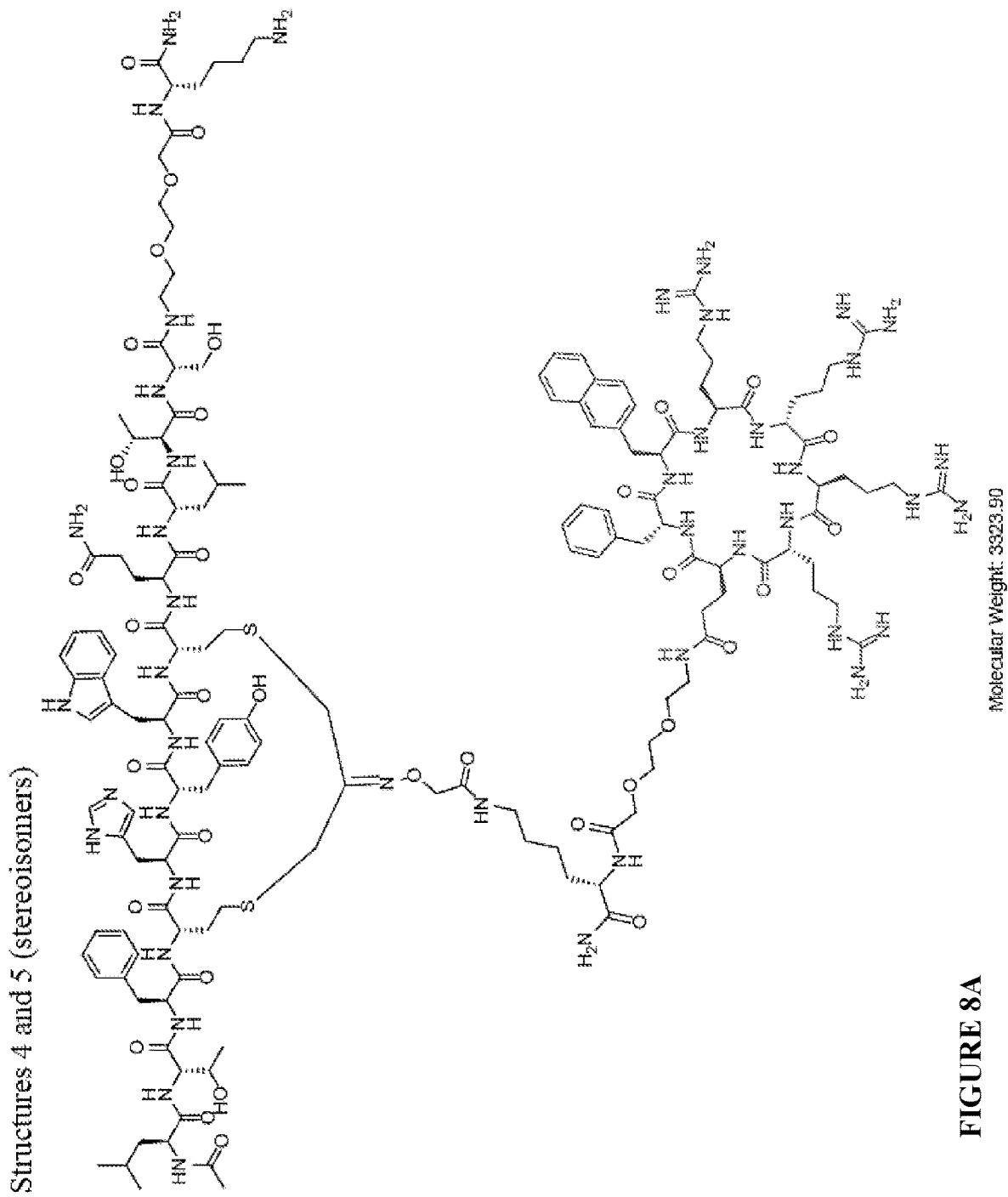
FIG. 8A shows the chemical structure of stapled peptide 4 and 5 (stereoisomers) which has been conjugated to a cCPP (cCPP 9) via a linker and an HPLC chromatogram.
Figure 8A:
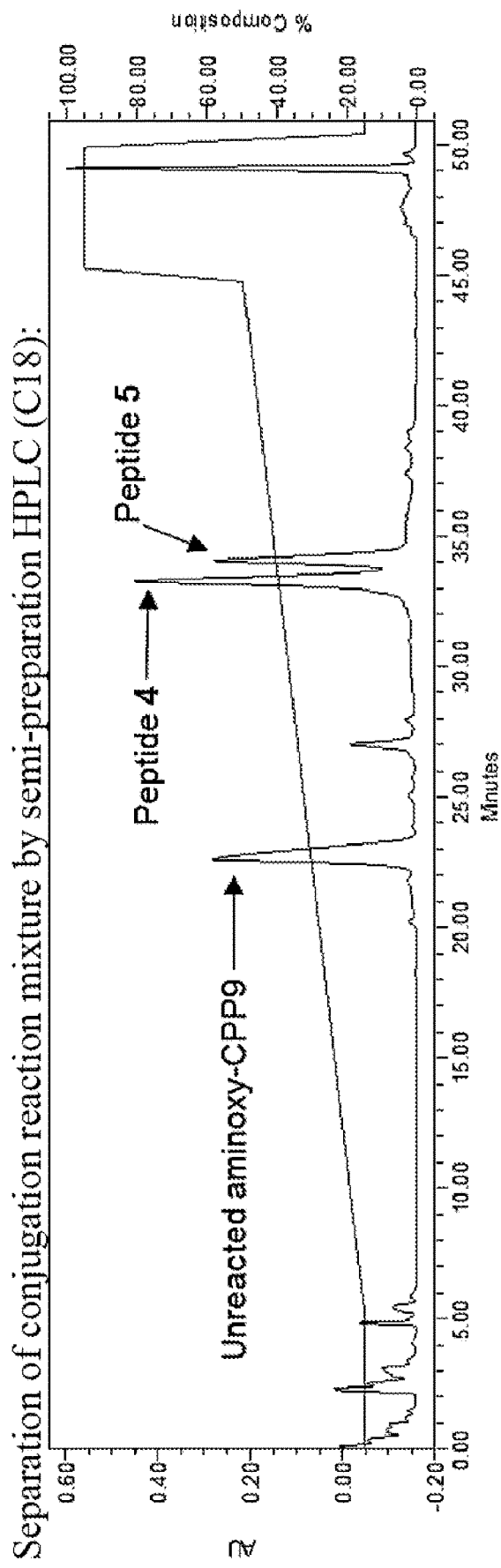
Figure 8B:
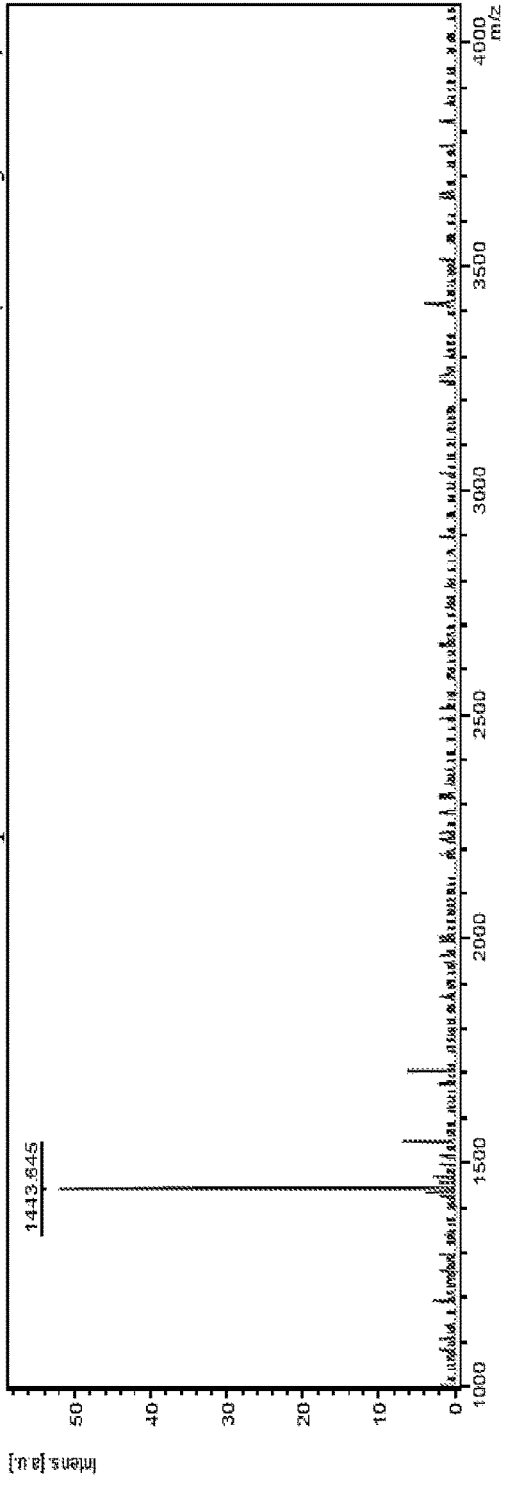
FIG. 8B shows low-resolution MALDI-TOF MS spectra for aminoxy-cCPP9 (peak at retention time=23 minutes), structure 4 (peak at retention time=33.5 minutes), and structure 5 (peak at retention time=34.5 minutes).
Figure 8B:
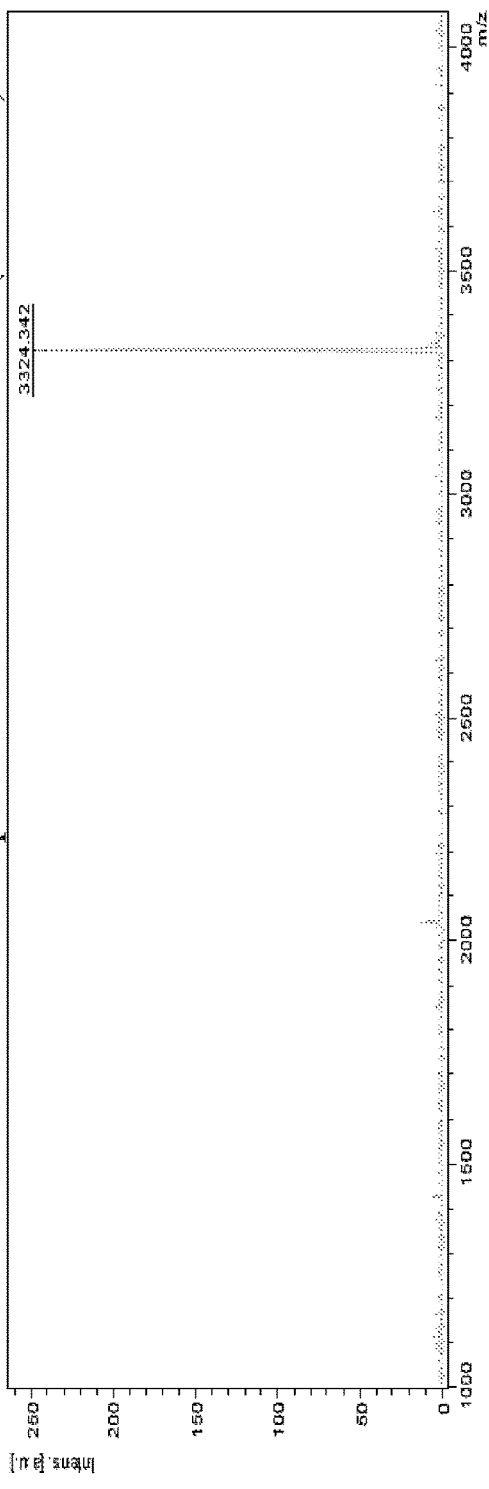
Figure 8B:
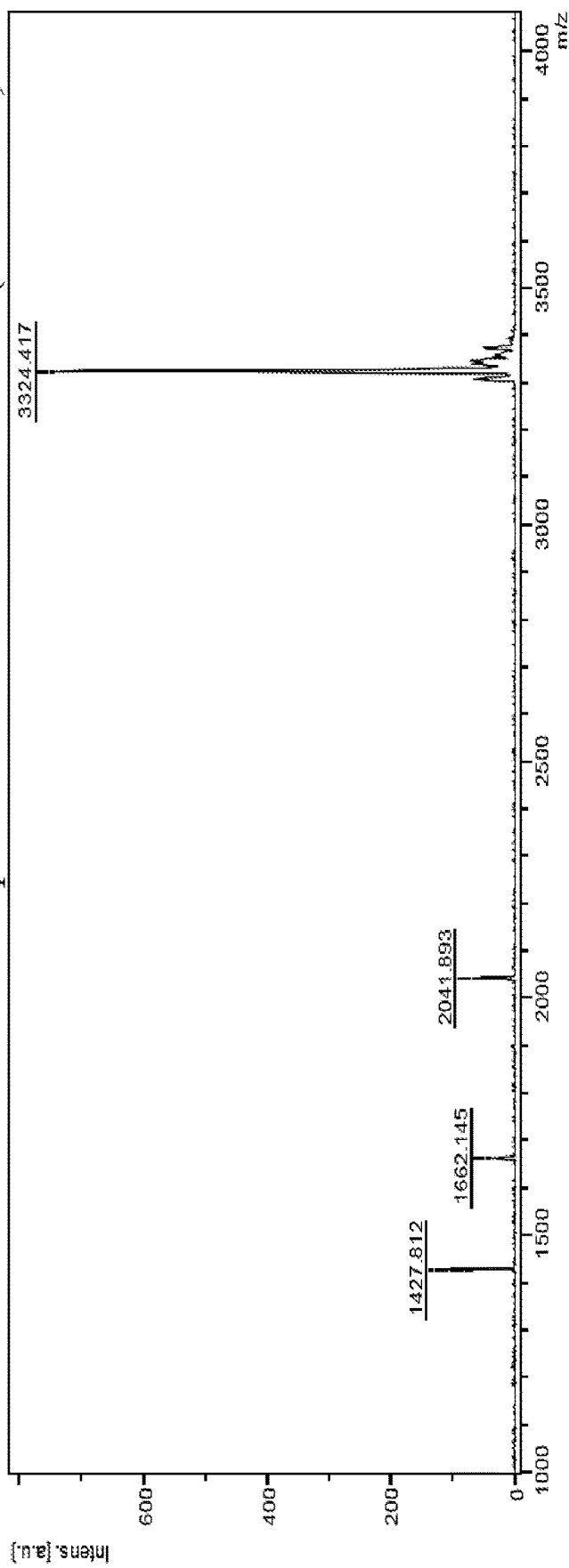
Figure 9:
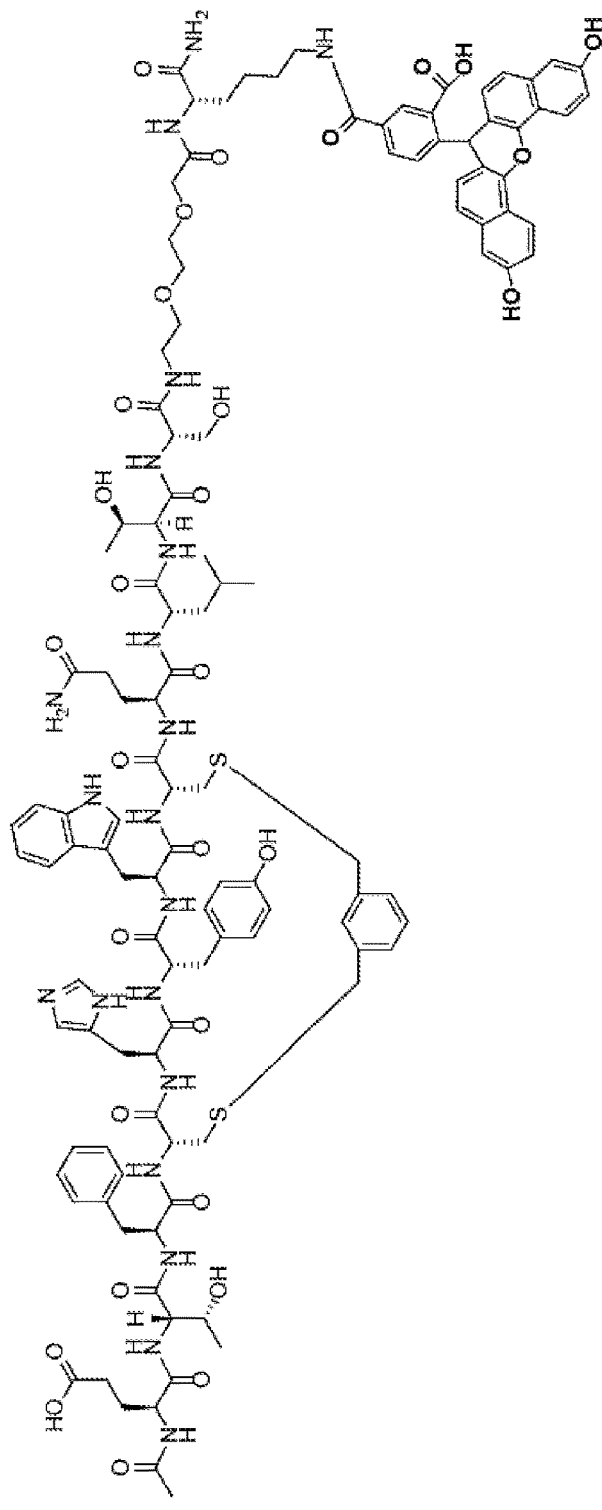
FIG. 9 shows the chemical structure for stapled, labeled peptide 10, HPLC chromatograms and an MS spectrum.
Figure 9:
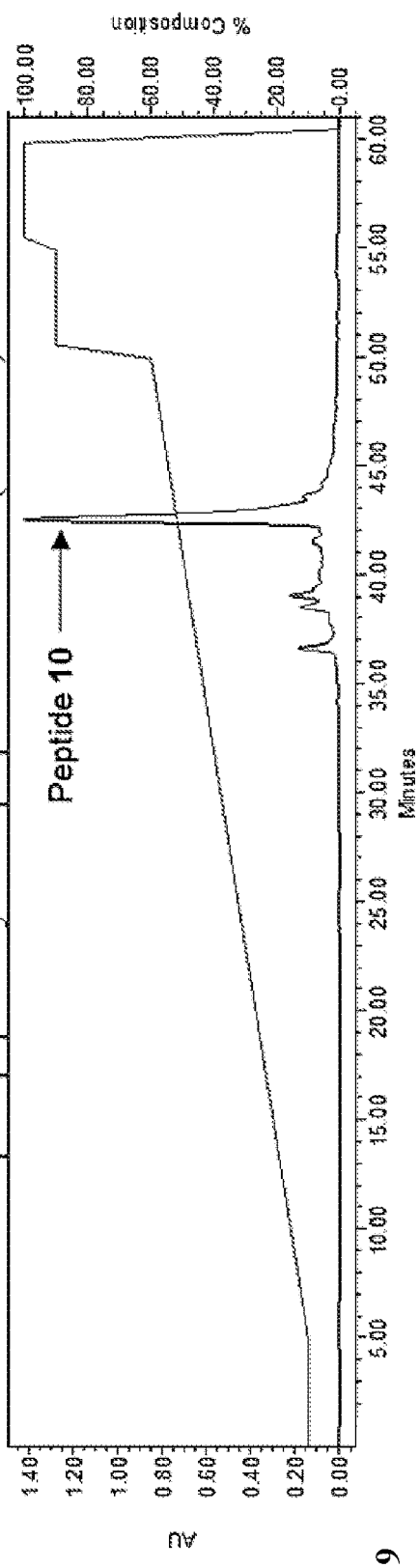
Figure 9:
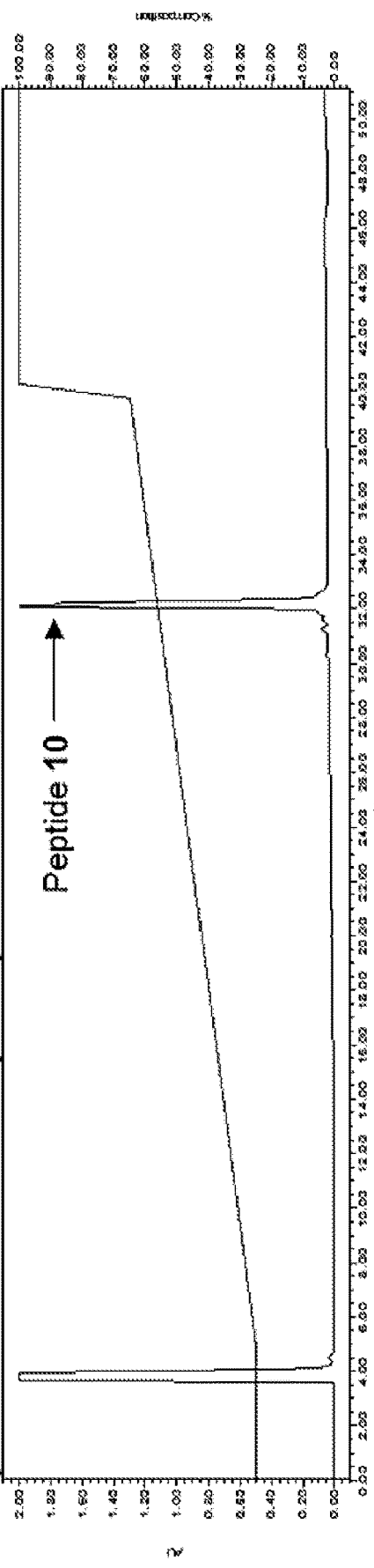
Figure 9:
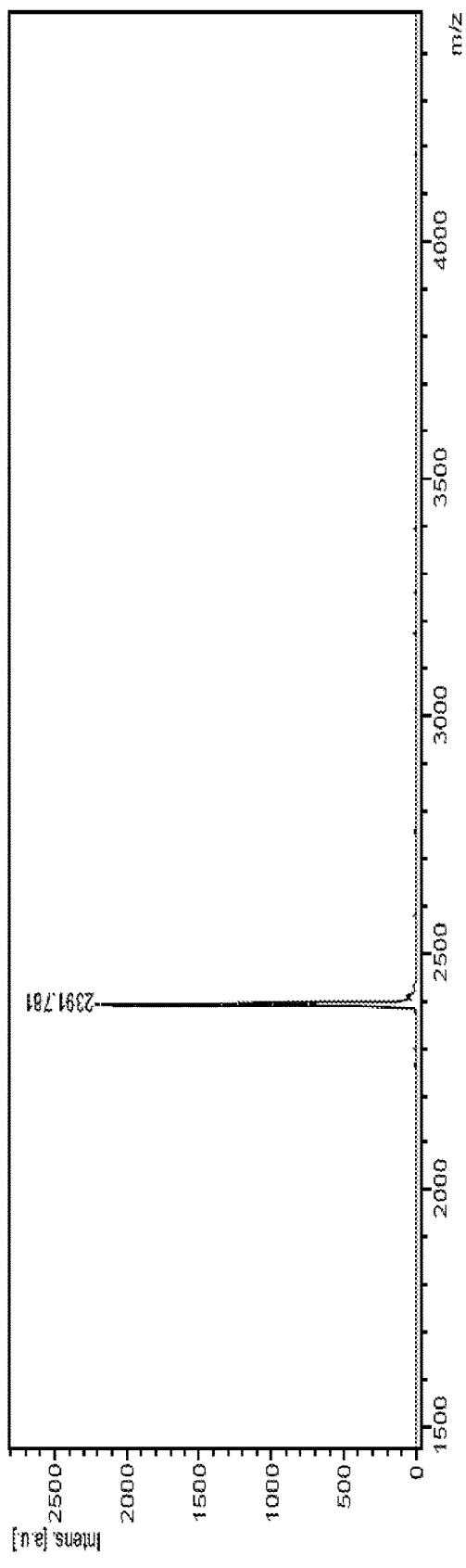
Figure 10A:
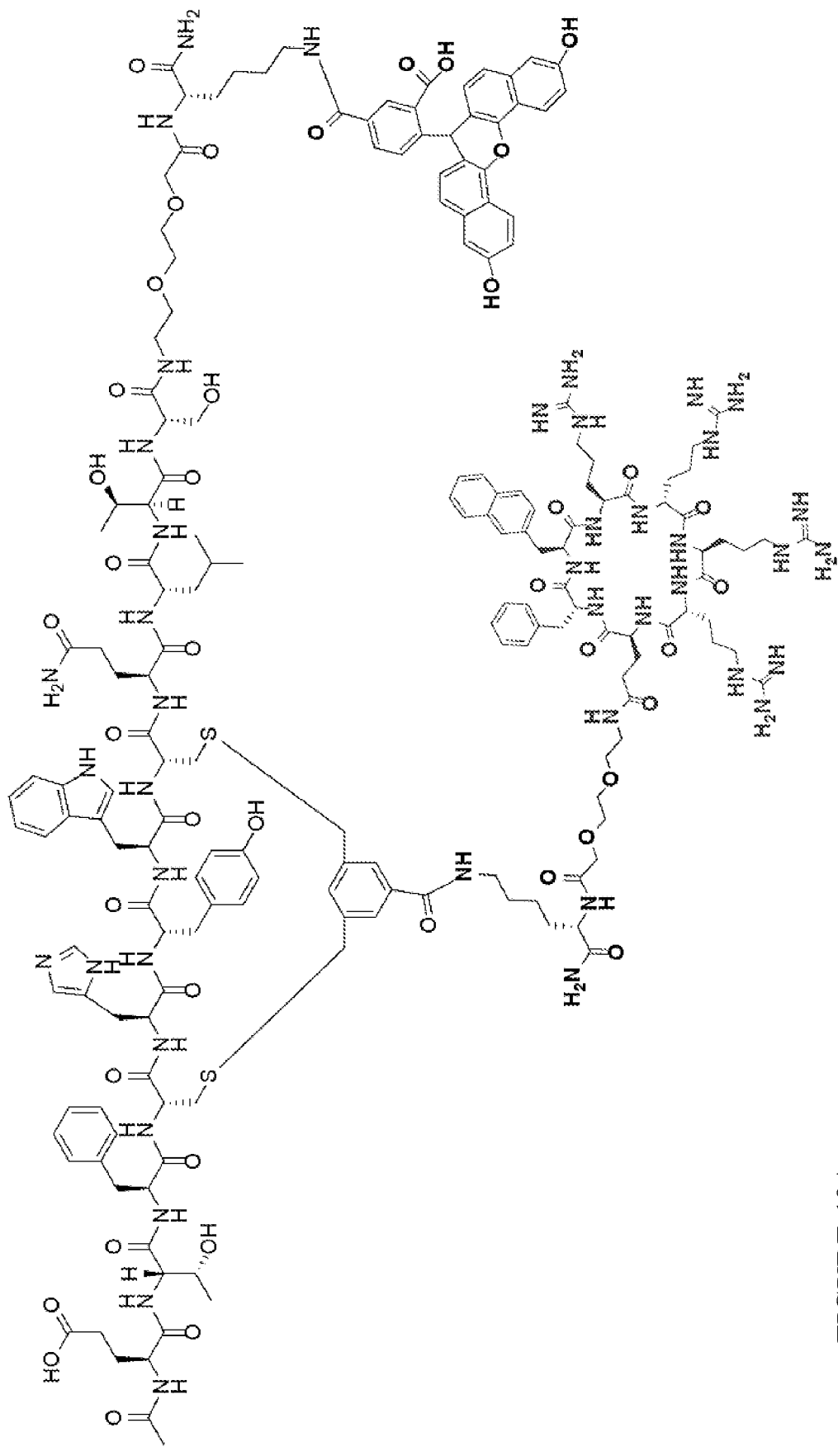
FIGS. 10A-10B shows the chemical structure of stapled, labeled peptide 11 conjugated to a cCPP via a linker, HPLC chromatograms (FIG. 10A) and an MS spectrum (FIG. 10B).
Figure 10A:
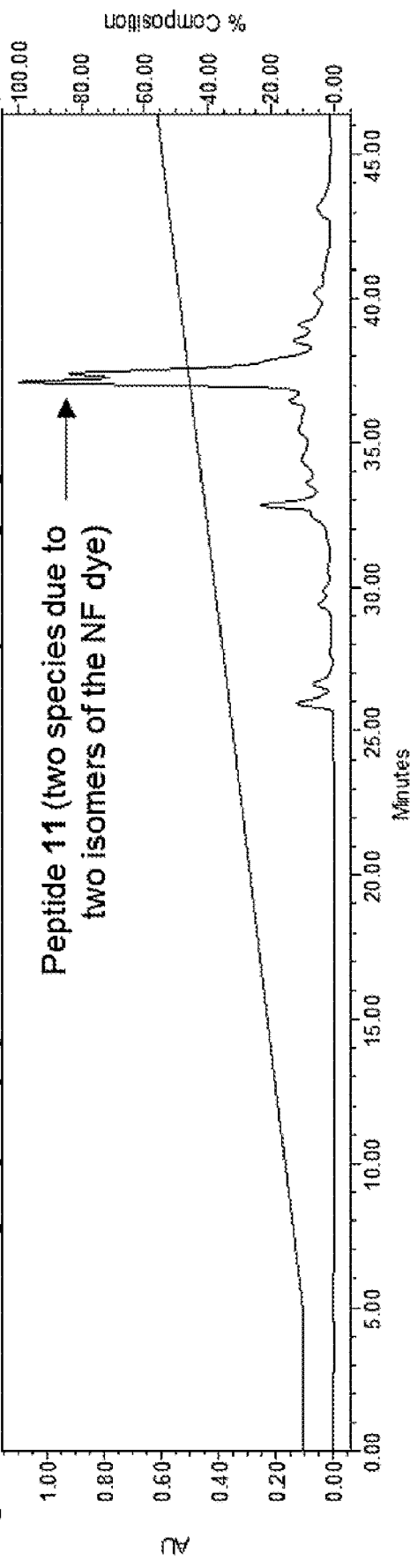
Figure 10A:
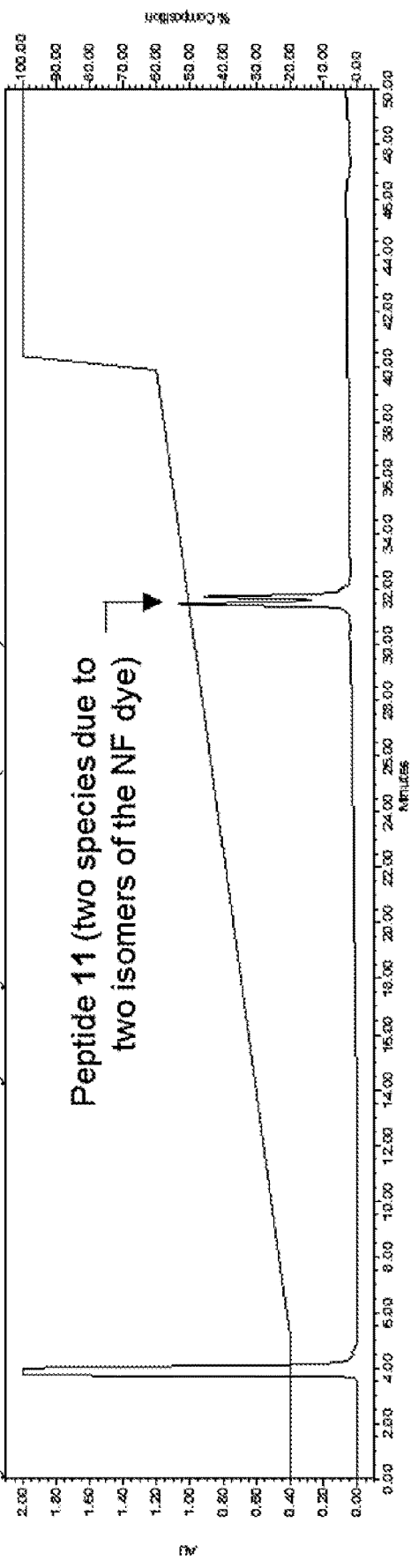
Figure 10B:
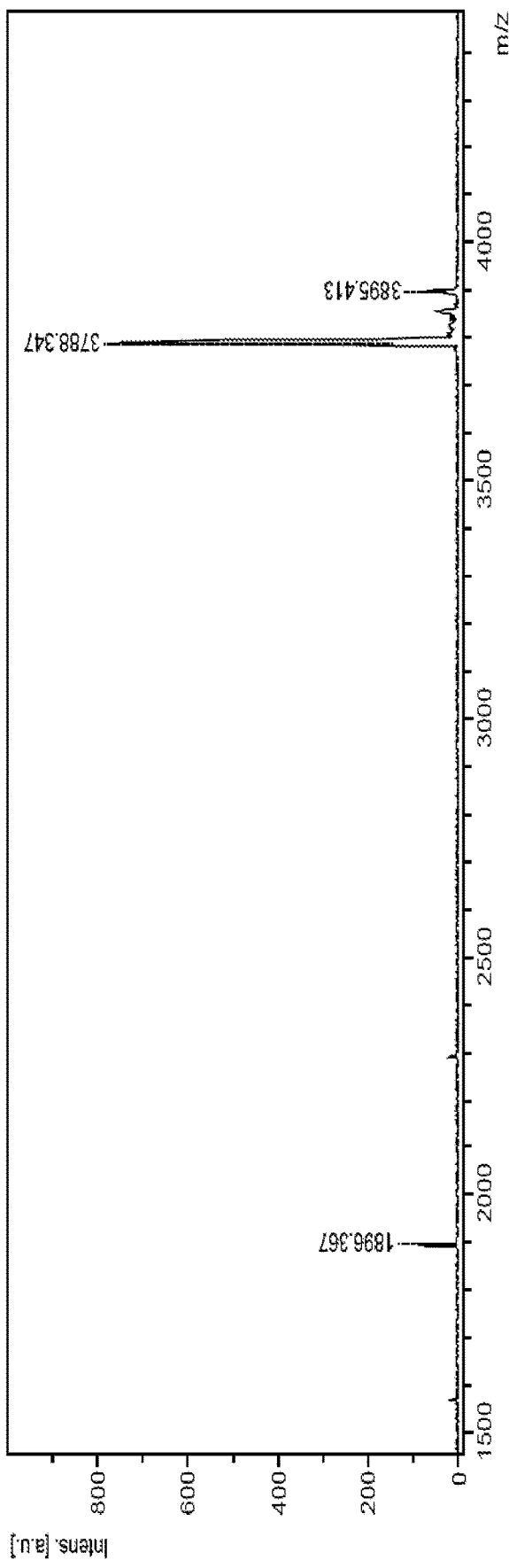
Figure 11A:
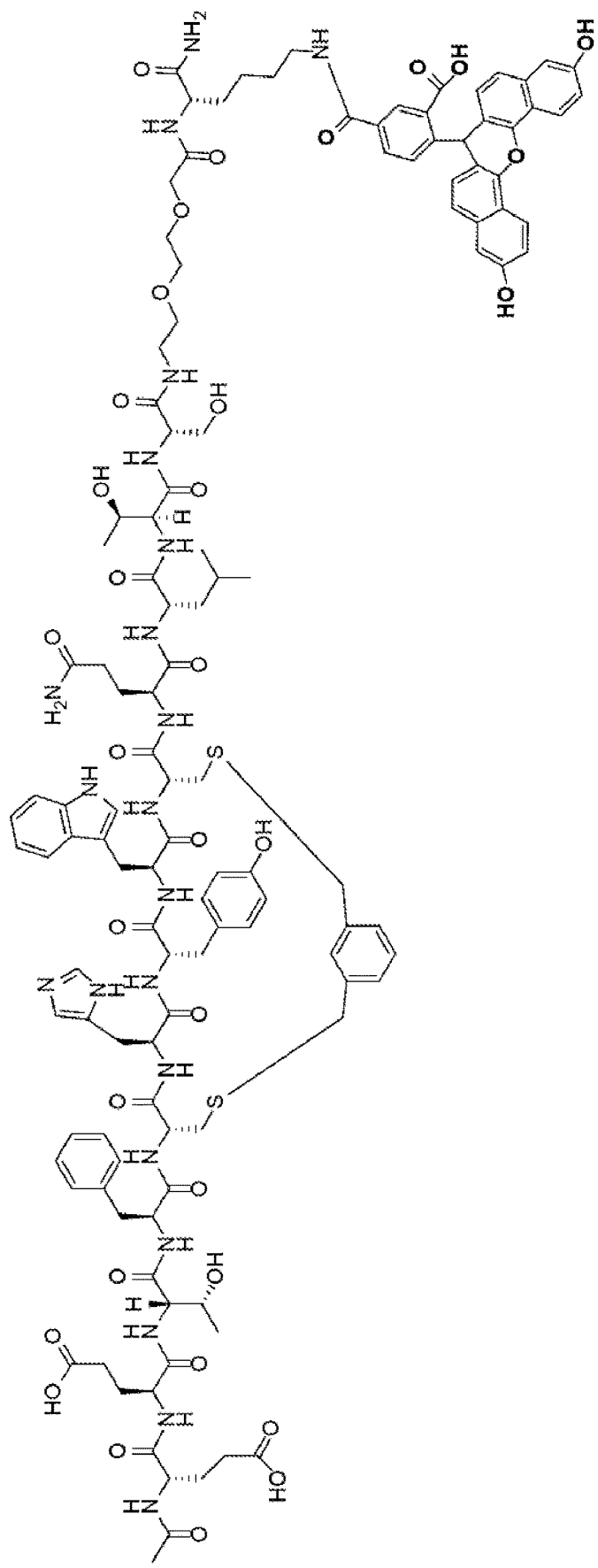
FIGS. 11A-11B shows the chemical structure of stapled, labeled peptide 12, HPLC chromatograms (FIG. 11A) and MS spectra (FIG. 11B).
Figure 11A:
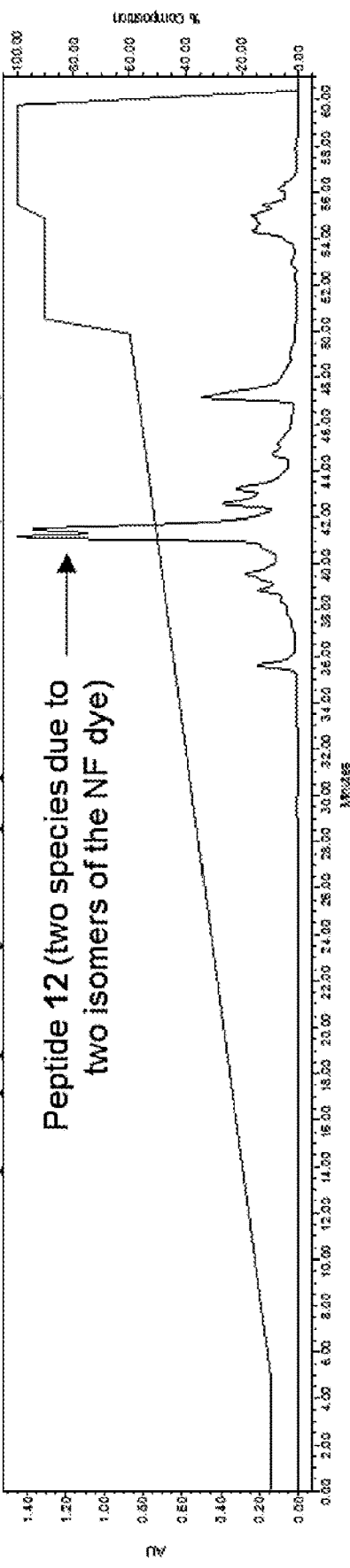
Figure 11A:
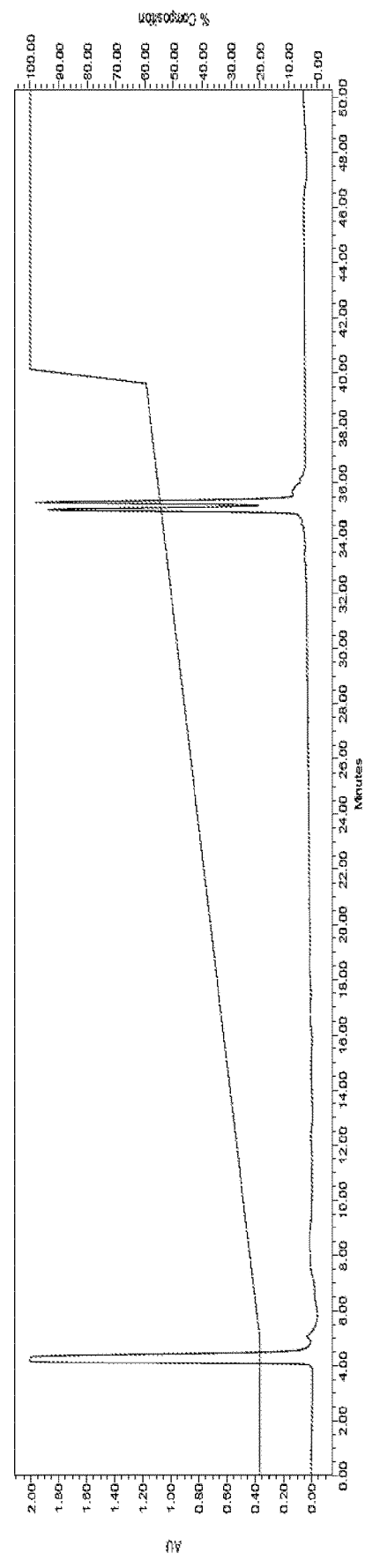
Figure 11B:
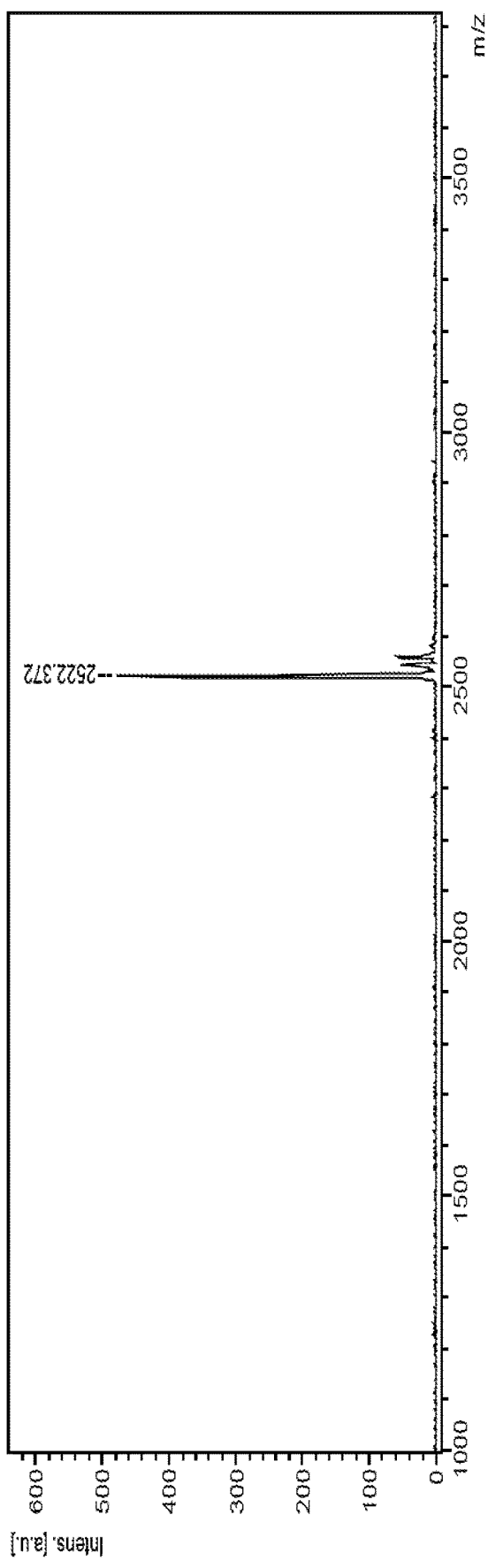
Figure 12A:
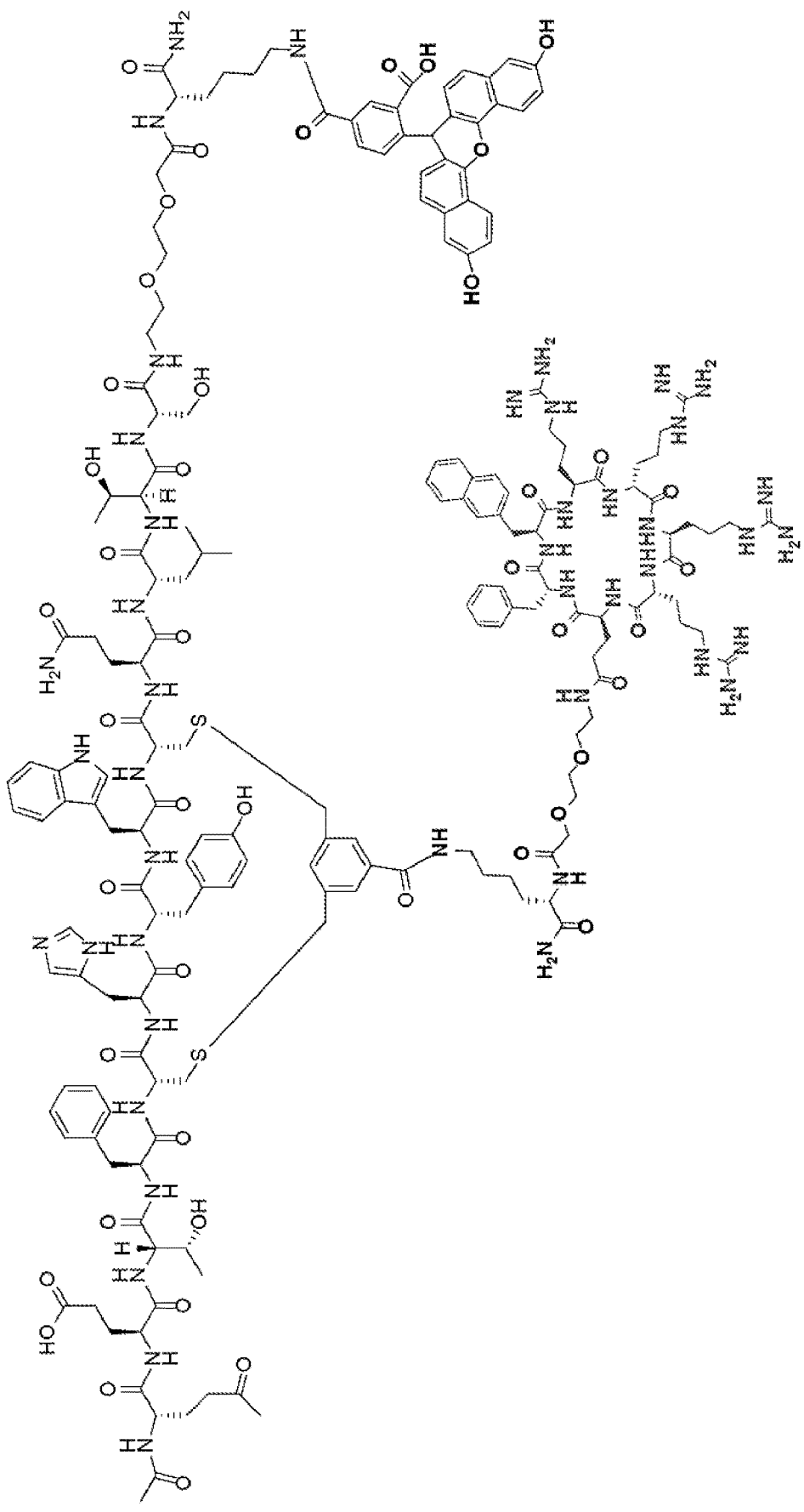
FIGS. 12A-12B shows the chemical structure of stapled, labeled peptide 13 conjugated to a cCPP via a linker, HPLC chromatograms (FIG. 12A), and an MS spectrum (FIG. 12B).
Figure 12A:
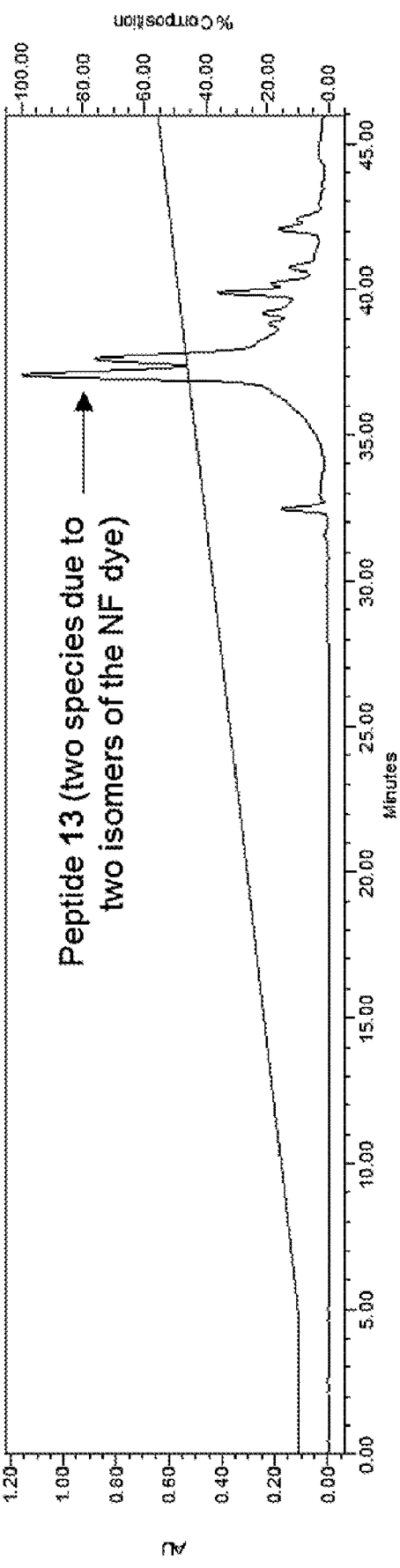
Figure 12A:
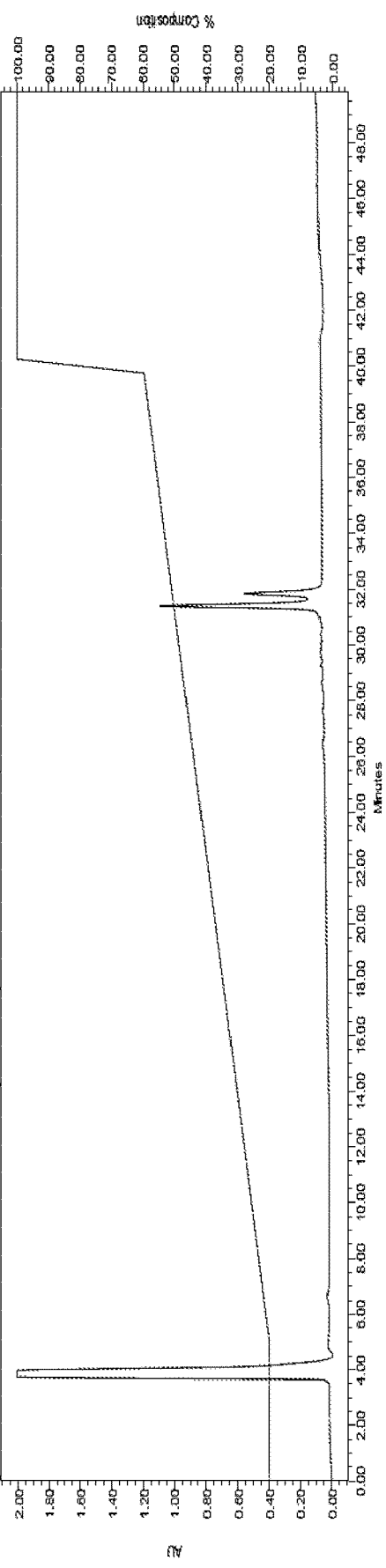
Figure 12B:
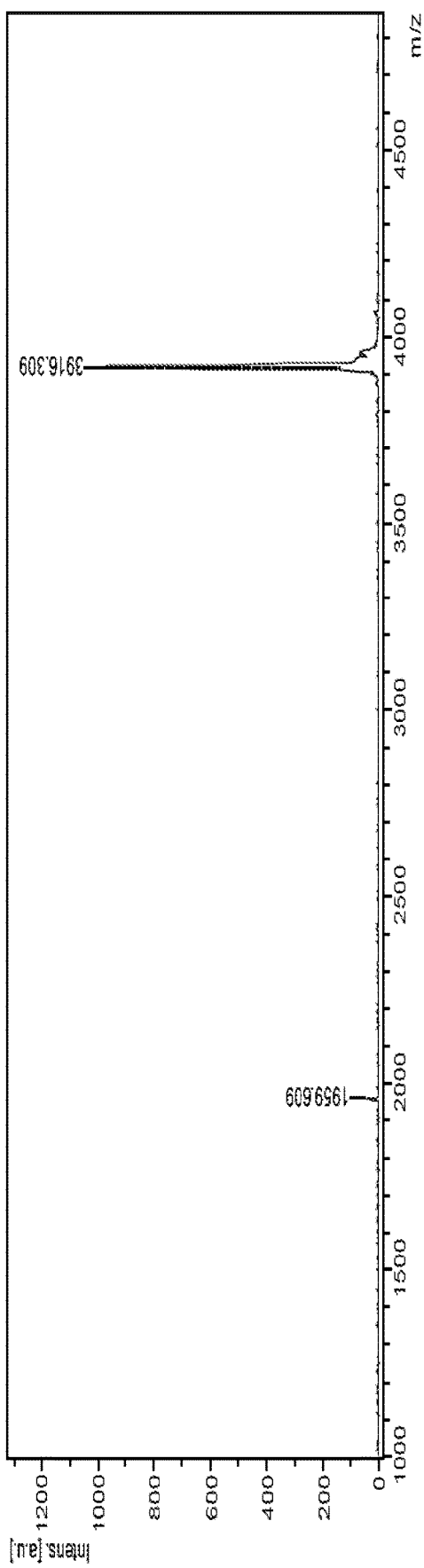
Figure 13:
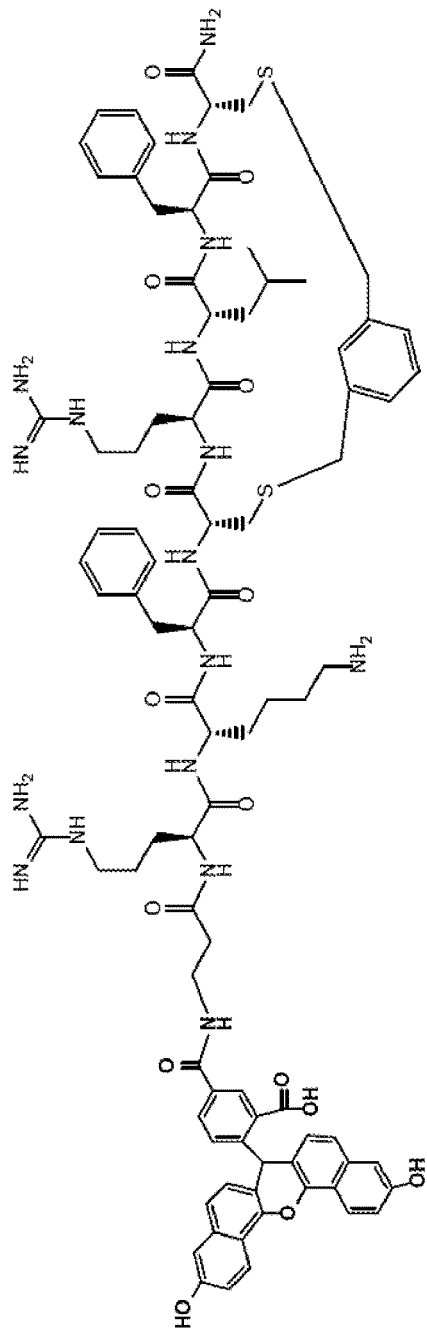
FIG. 13 shows the chemical structure of stapled, labeled peptide 14, HPLC chromatograms, and an MS spectrum.
Figure 13:
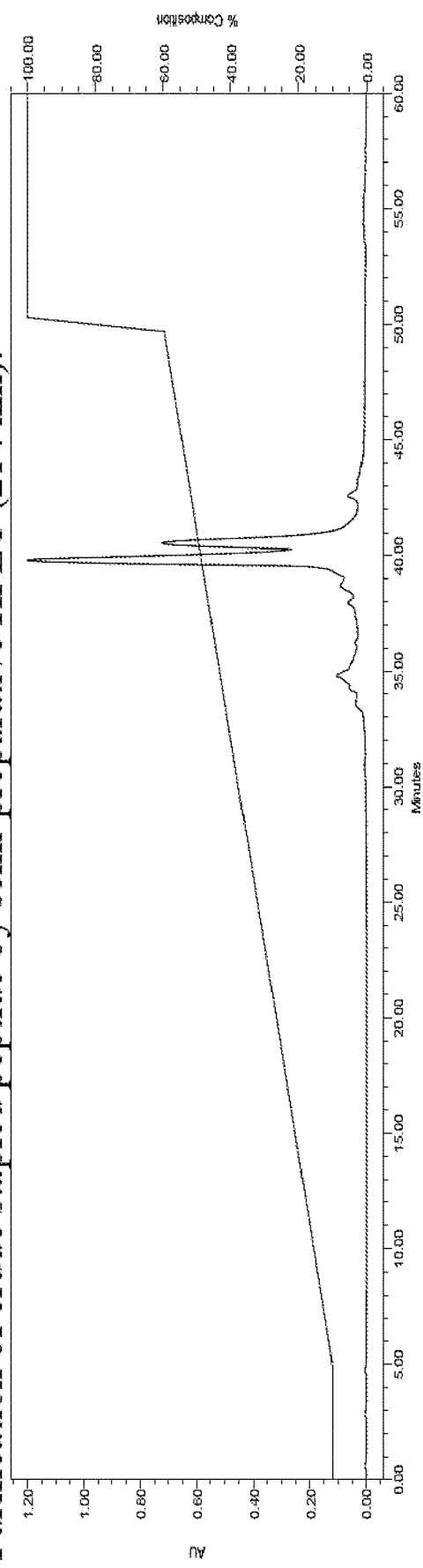
Figure 13:
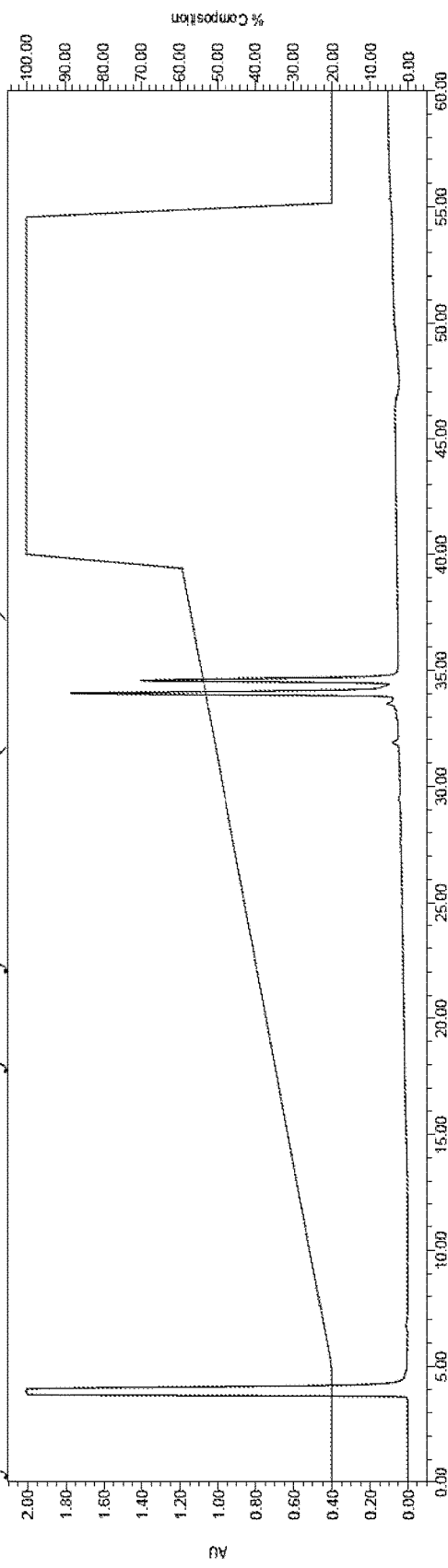
Figure 13:
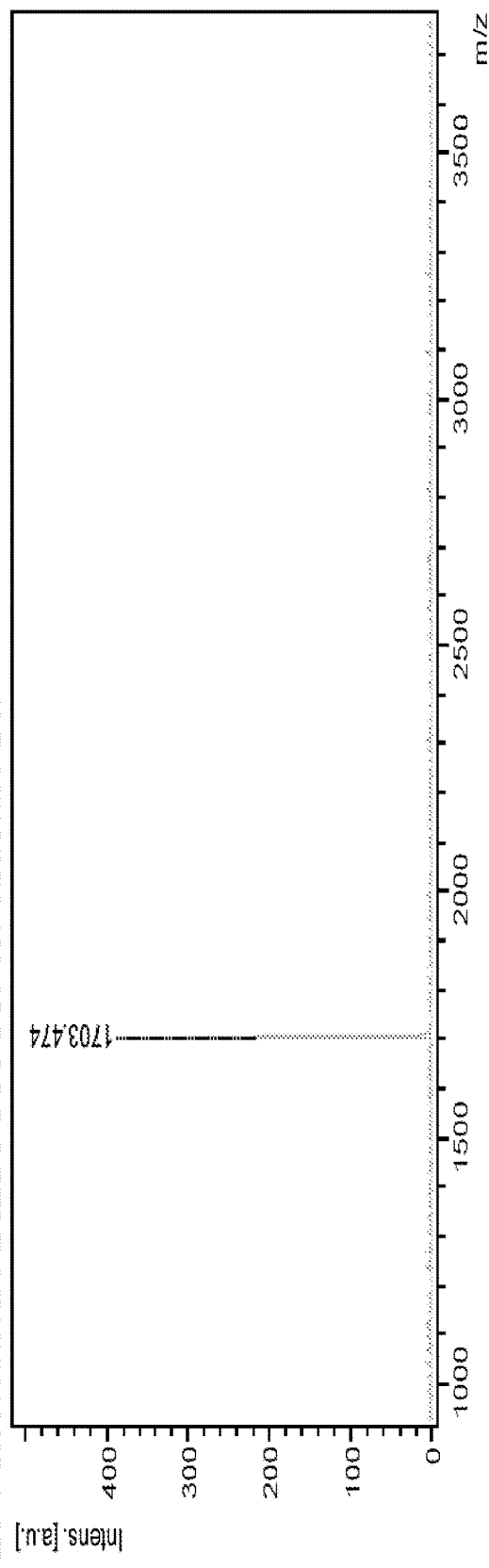
Figure 14A:
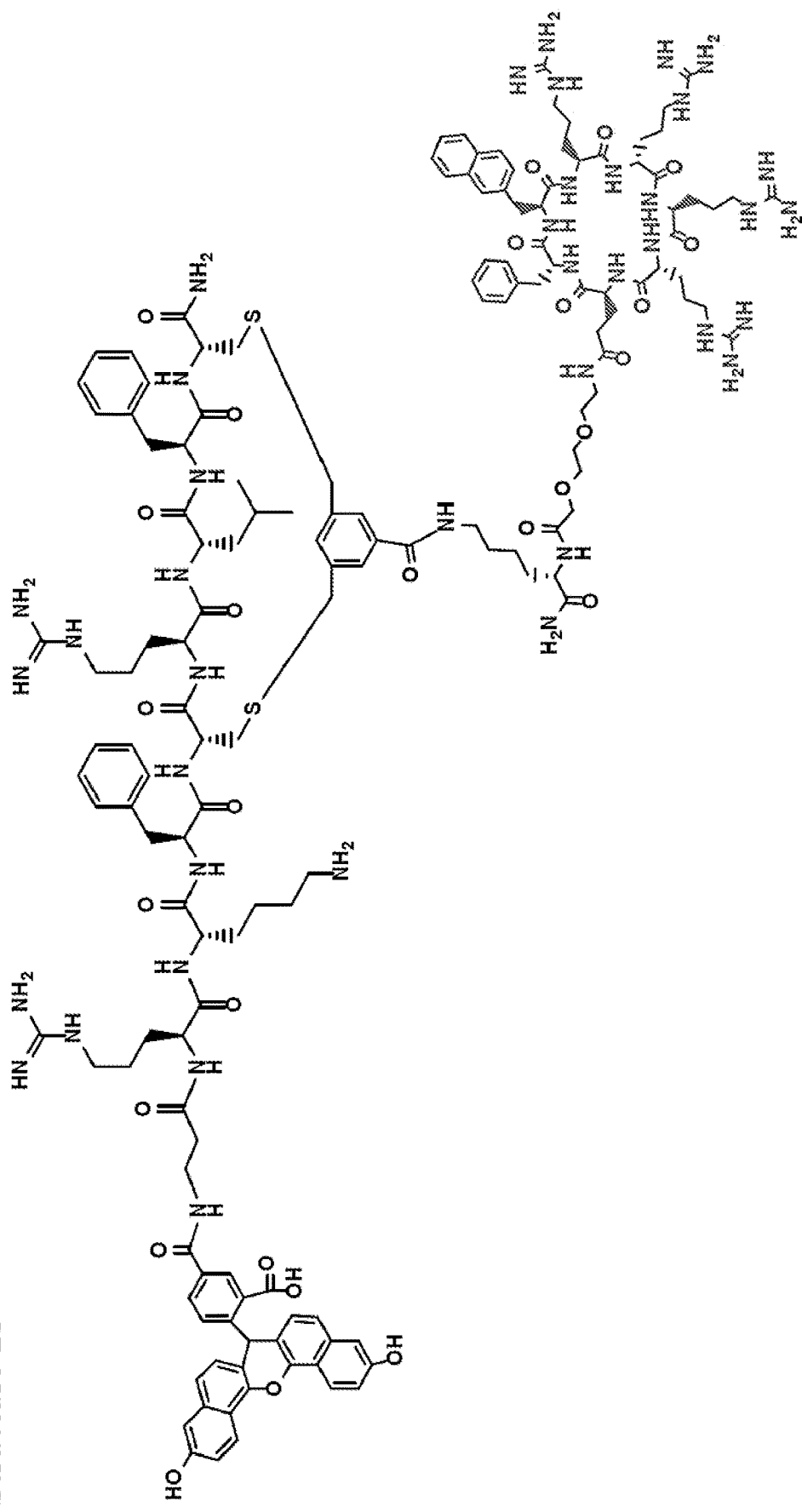
FIGS. 14A-14B shows the chemical structure of stapled, labeled peptide 15 conjugated to a cCPP via a linker, HPLC chromatograms (FIG. 14A) and a MS spectrum (FIG. 14B).
Figure 14A:
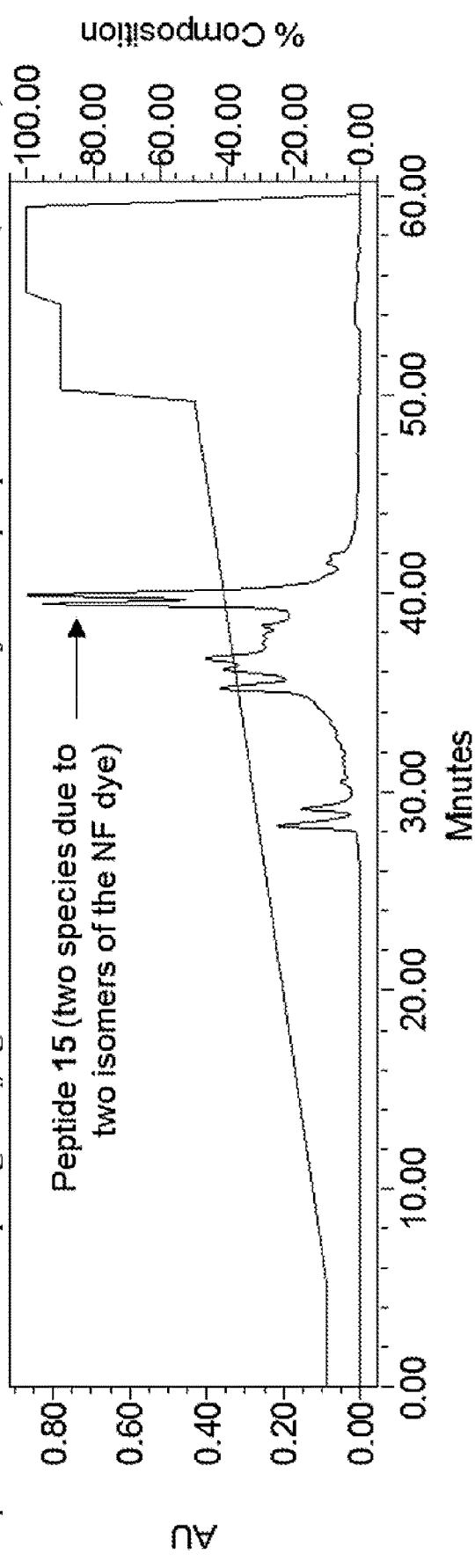
Figure 14A:
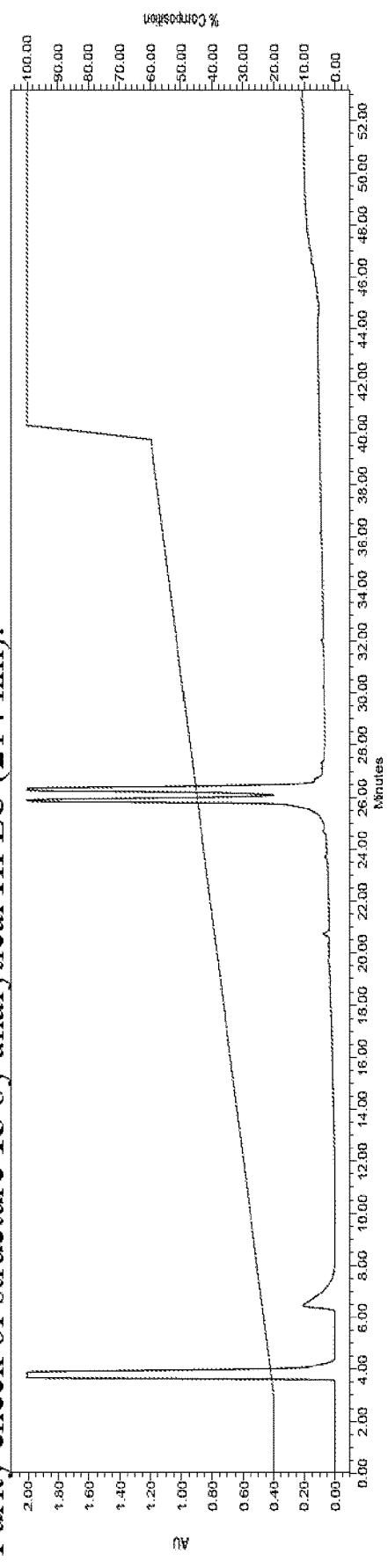
Figure 14B:
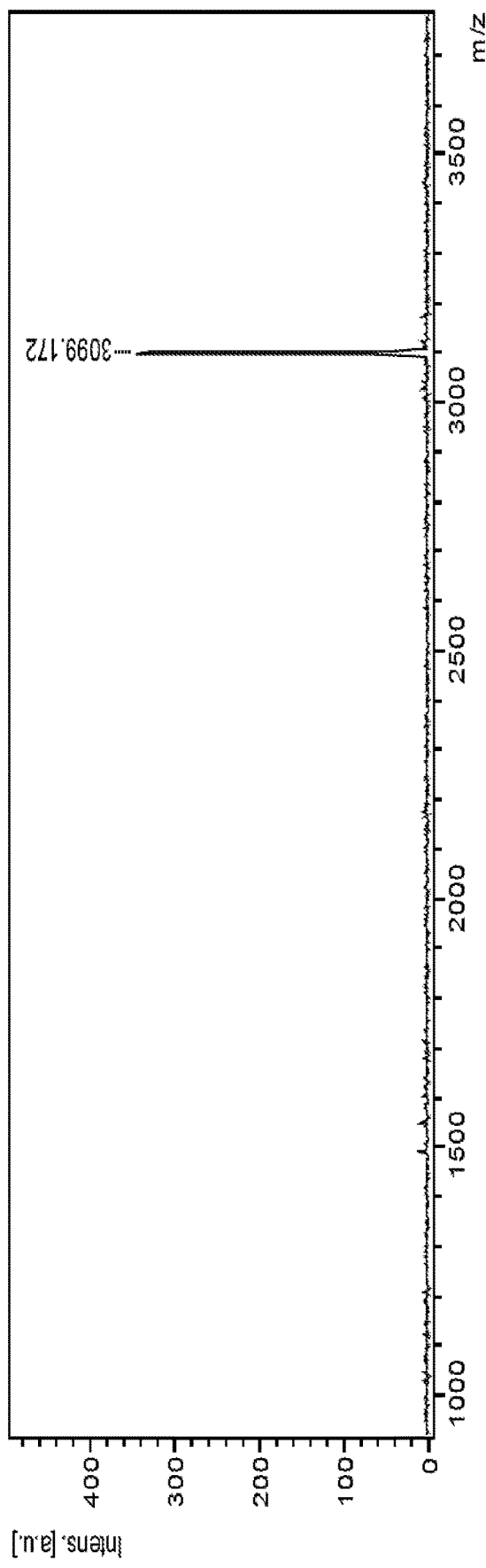
Figure 15:
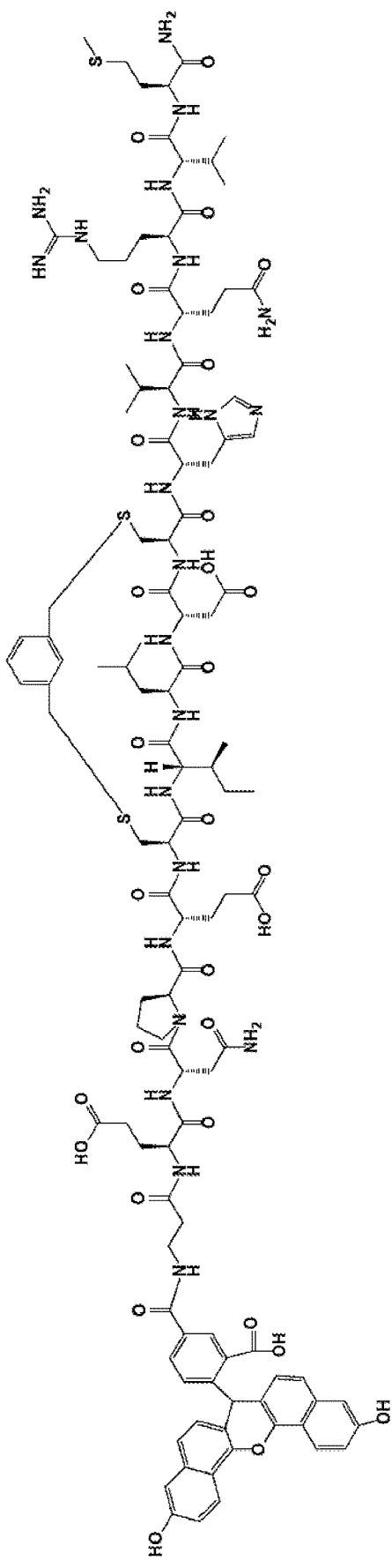
FIG. 15 shows the chemical structure of a stapled, labeled peptide 16, HPLC chromatograms, and a MS spectrum.
Figure 15:
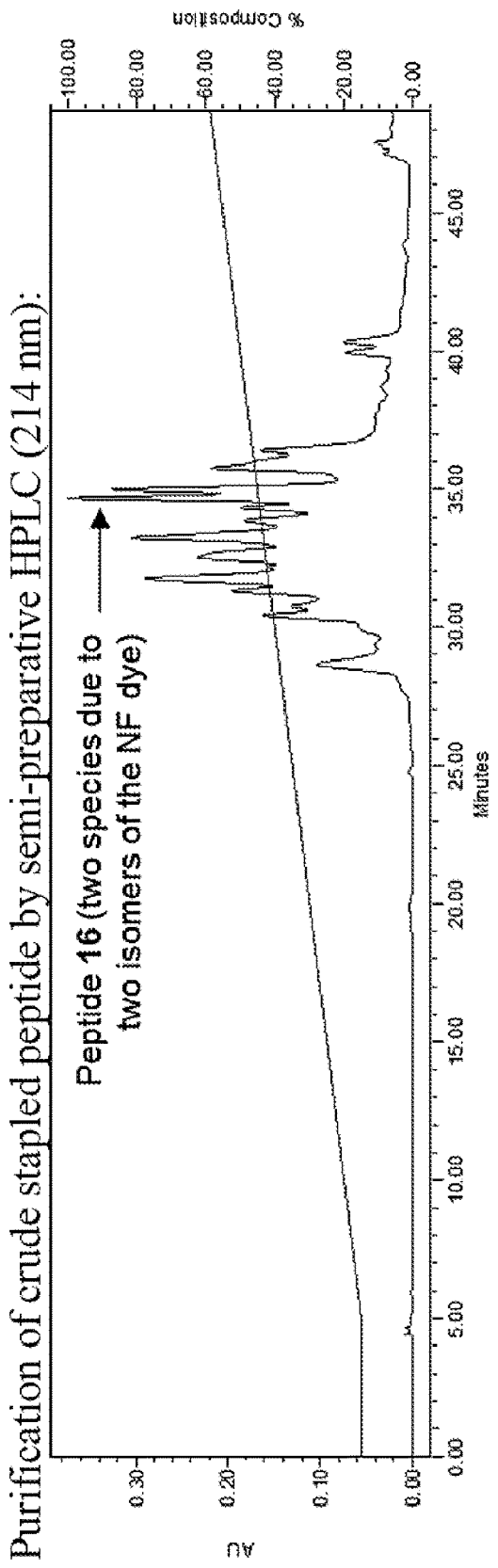
Figure 15:
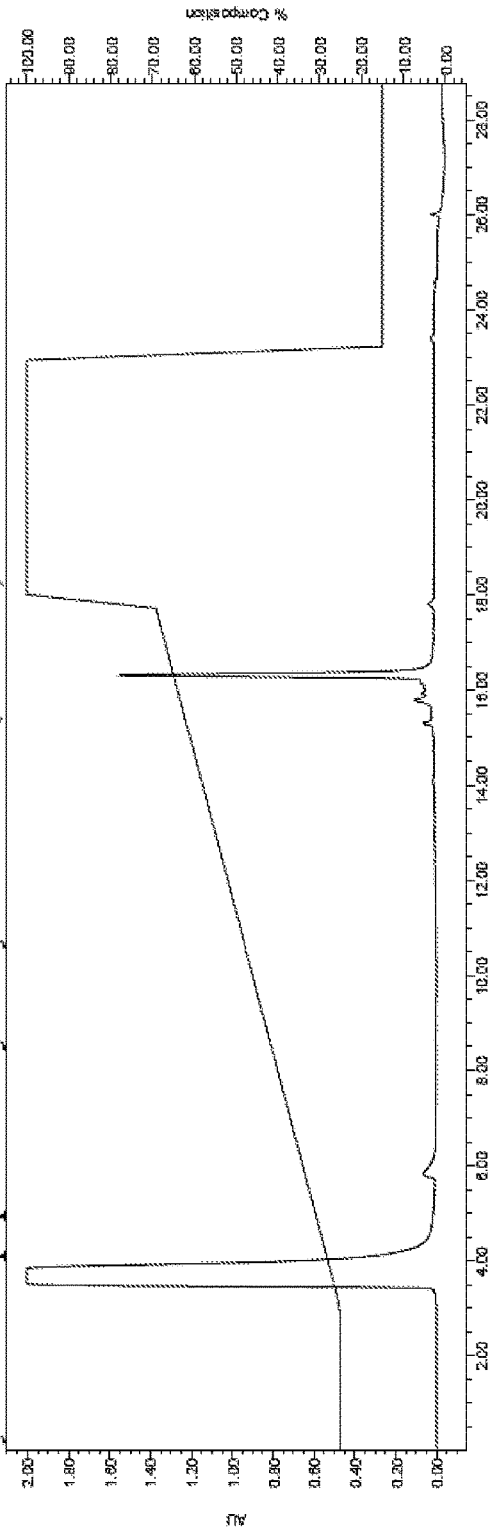
Figure 15:
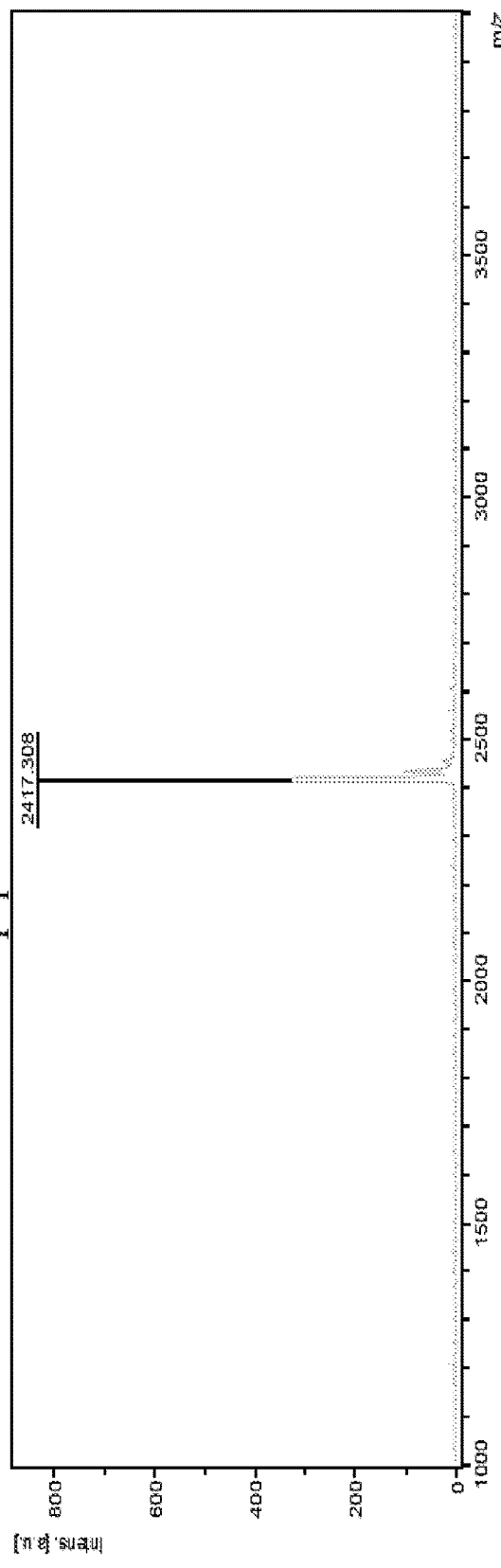
Figure 16A:
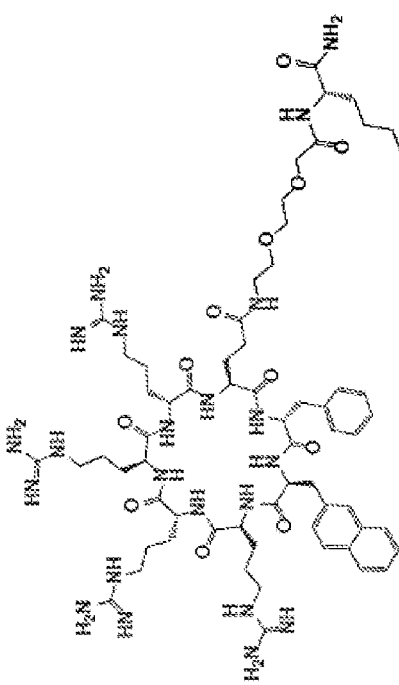
FIGS. 16A-16B shows the chemical structure of a stapled, labeled peptide 17 conjugated to a cCPP via a linker, HPLC chromatograms (FIG. 16A) and an MS spectrum (FIG. 16B).
Figure 16A:
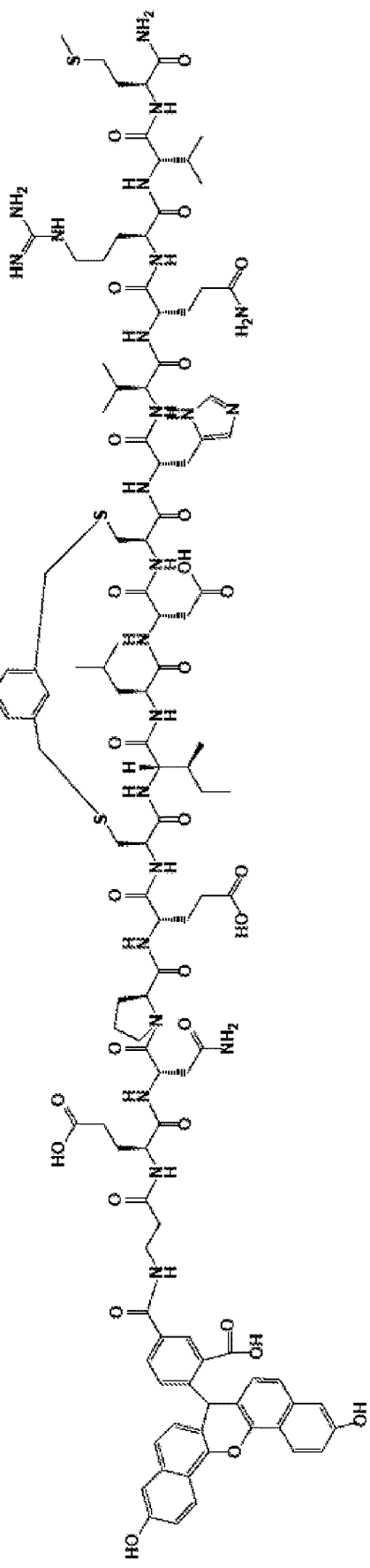
Figure 16A:
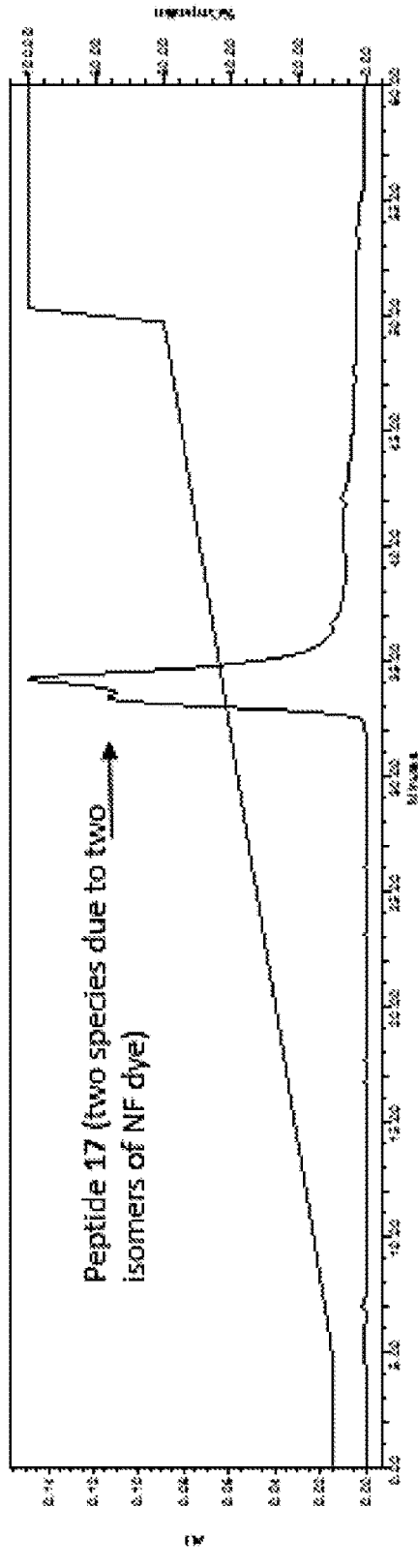
Figure 16A:
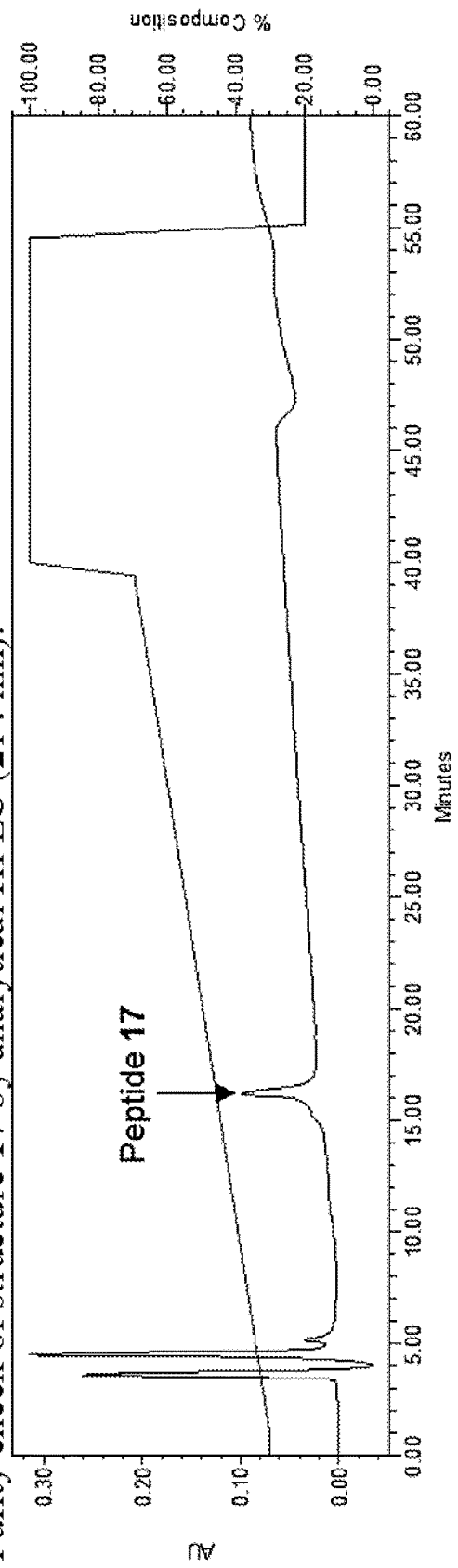
Figure 16B:
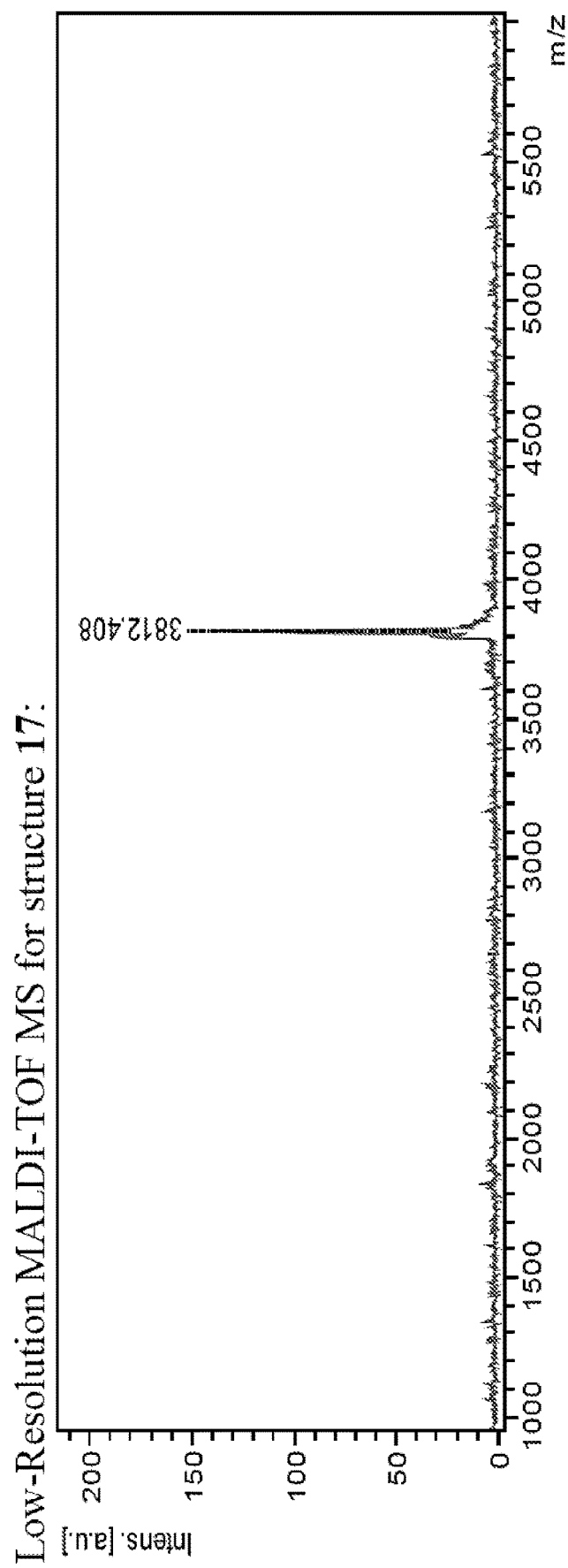
Figure 17:
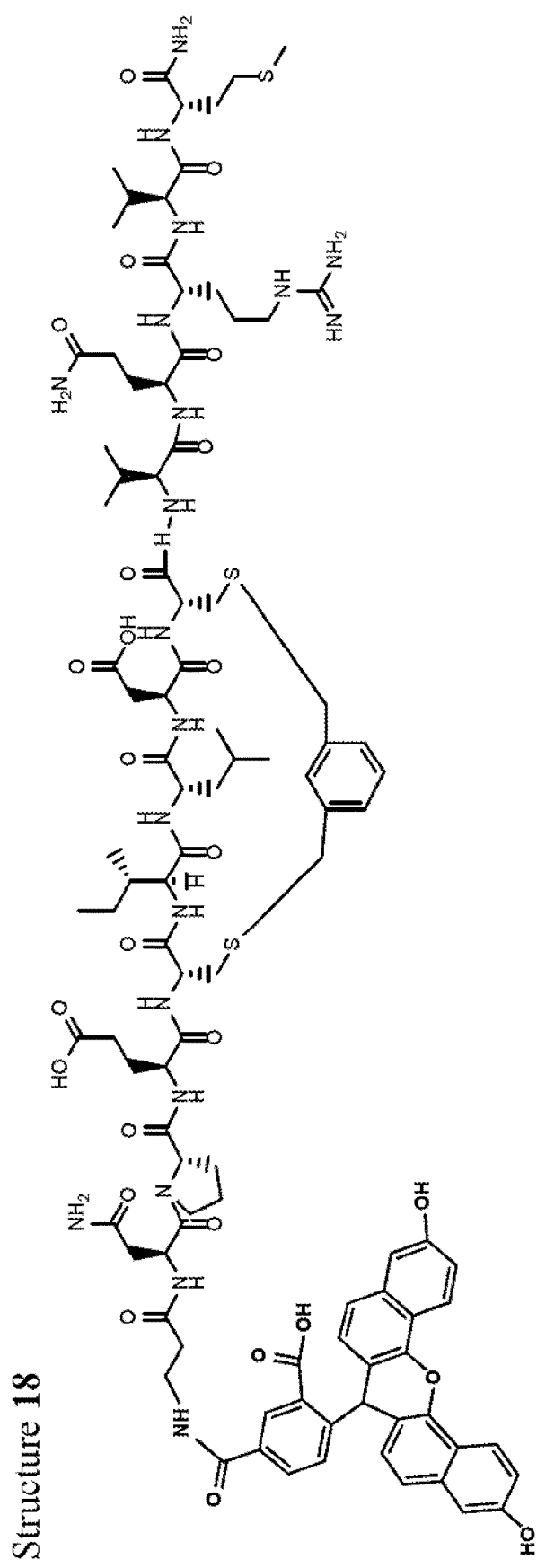
FIG. 17 shows the chemical structure of a stapled, labeled peptide 18, HPLC chromatograms, and a MS spectrum.
Figure 17:
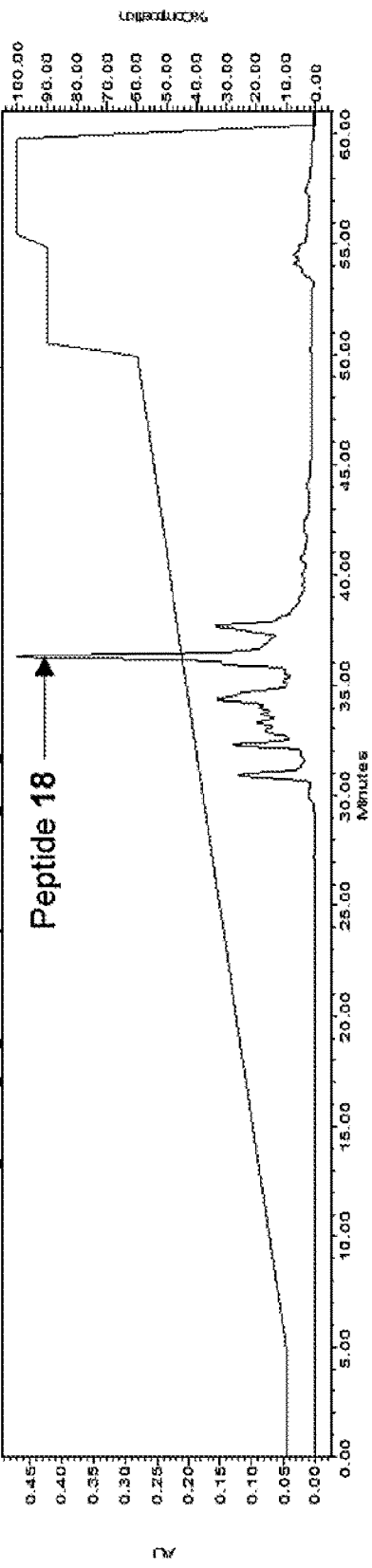
Figure 17:
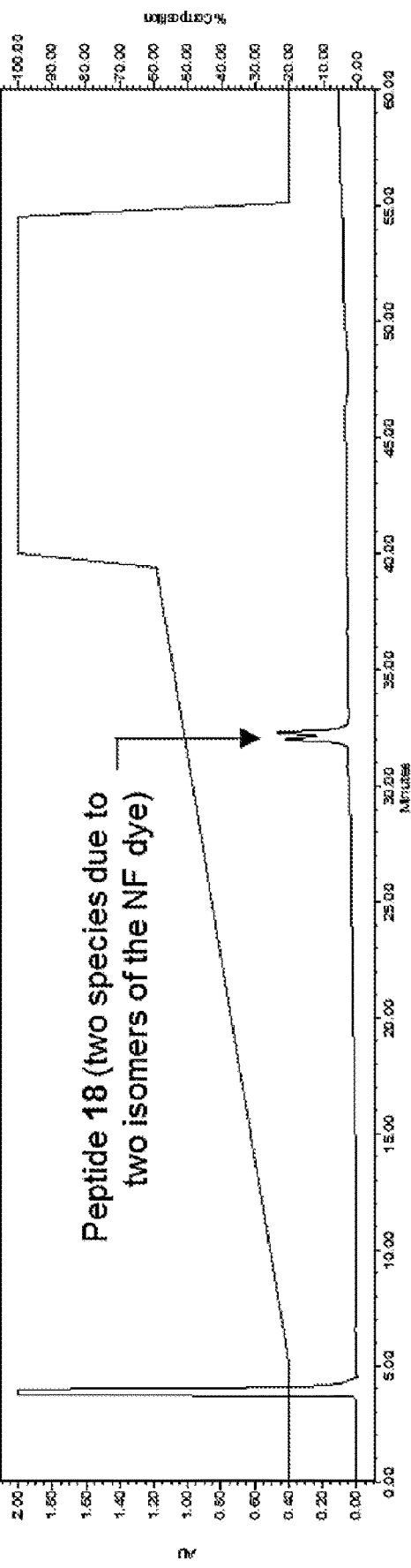
Figure 17:
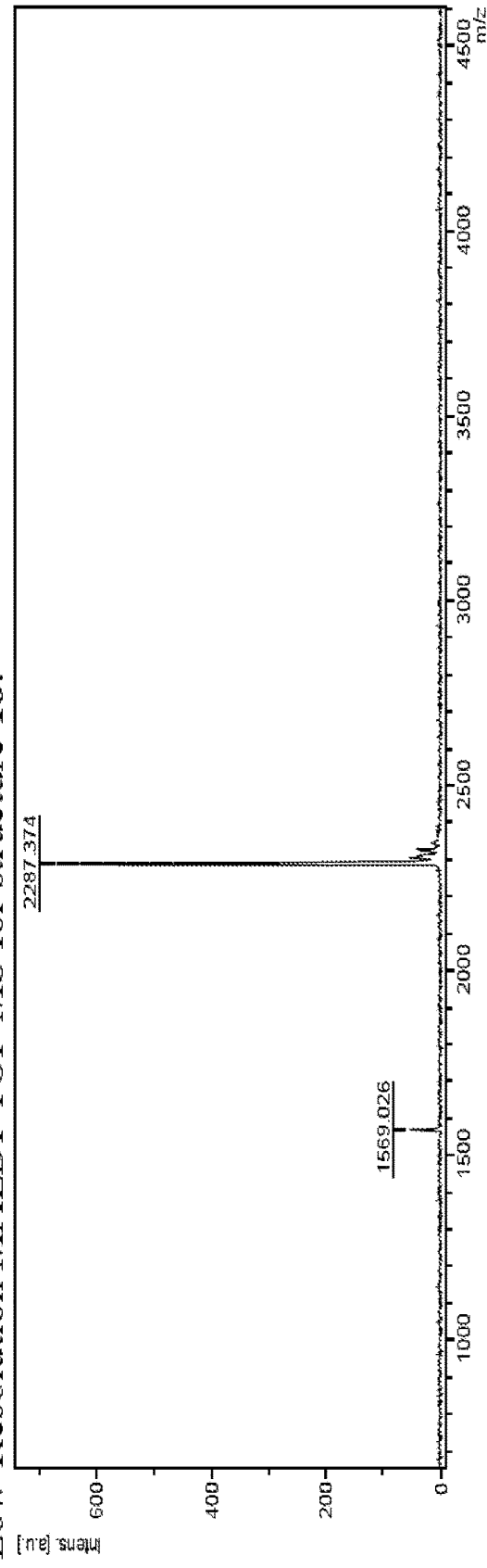
Figure 18A:
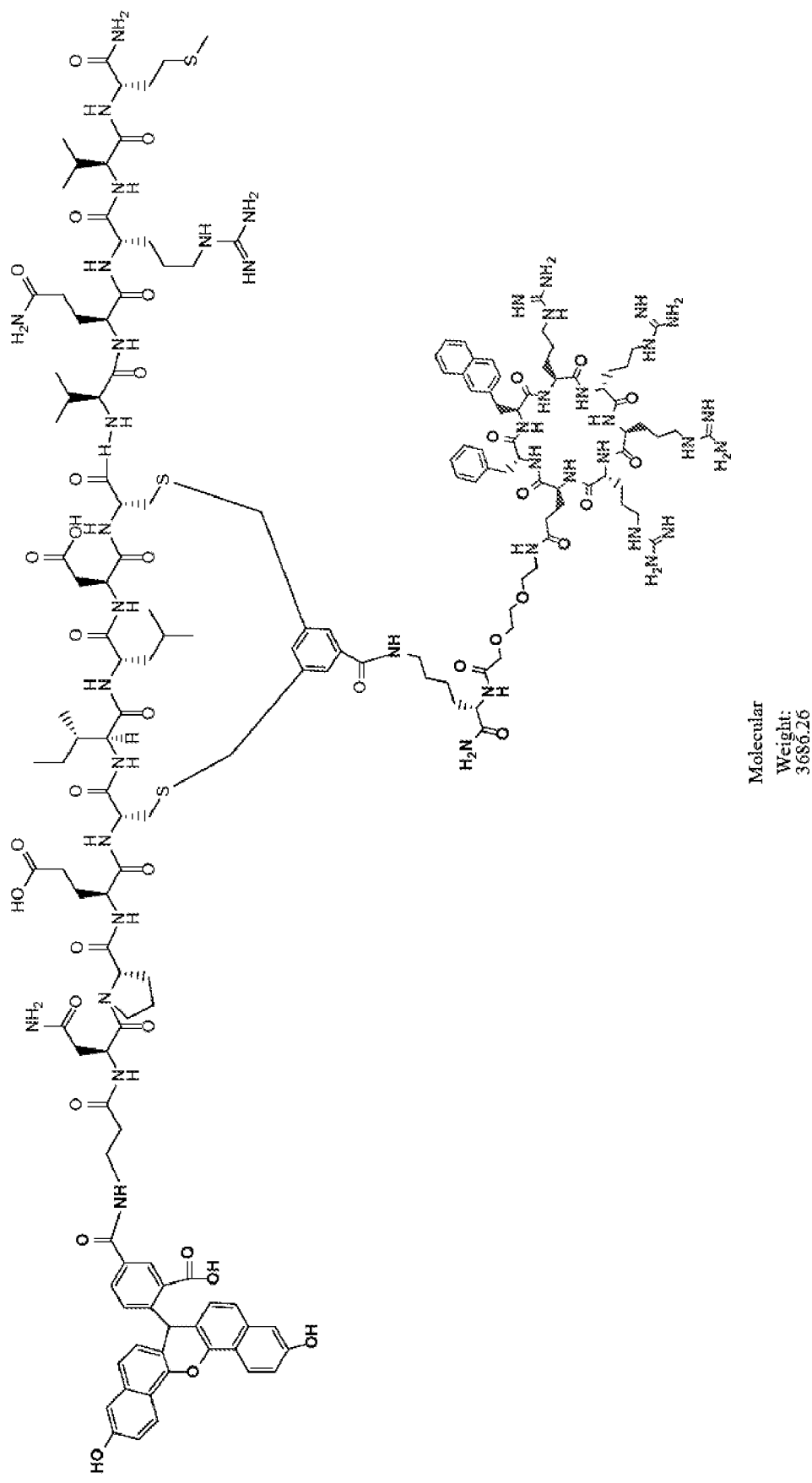
FIGS. 18A-18B shows the chemical structure of a stapled, labeled peptide 19 conjugated to a cCPP via a linker, HPLC chromatograms (FIG. 18A) and a MS spectrum (FIG. 18B).
Figure 18A:
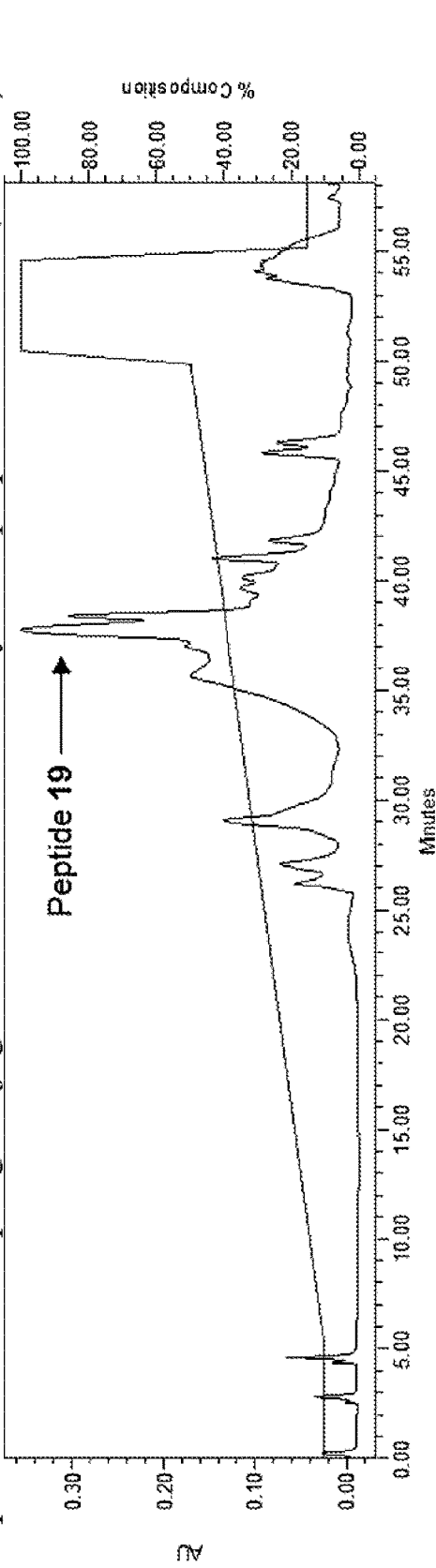
Figure 18A:
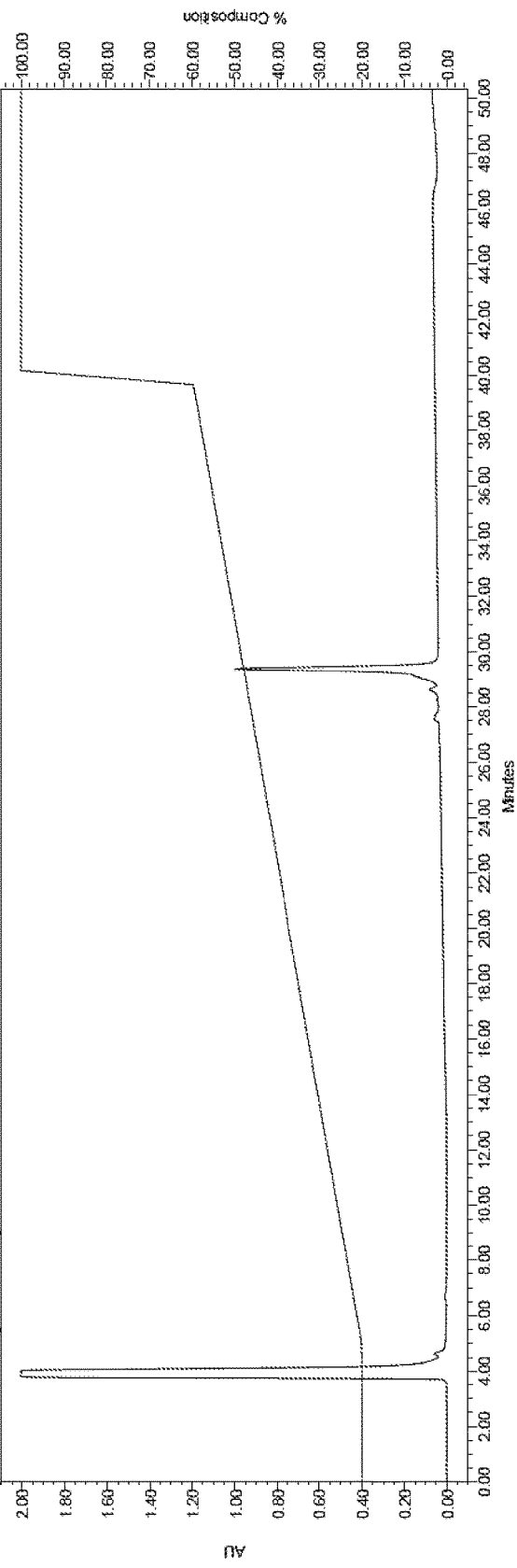
Figure 18B:
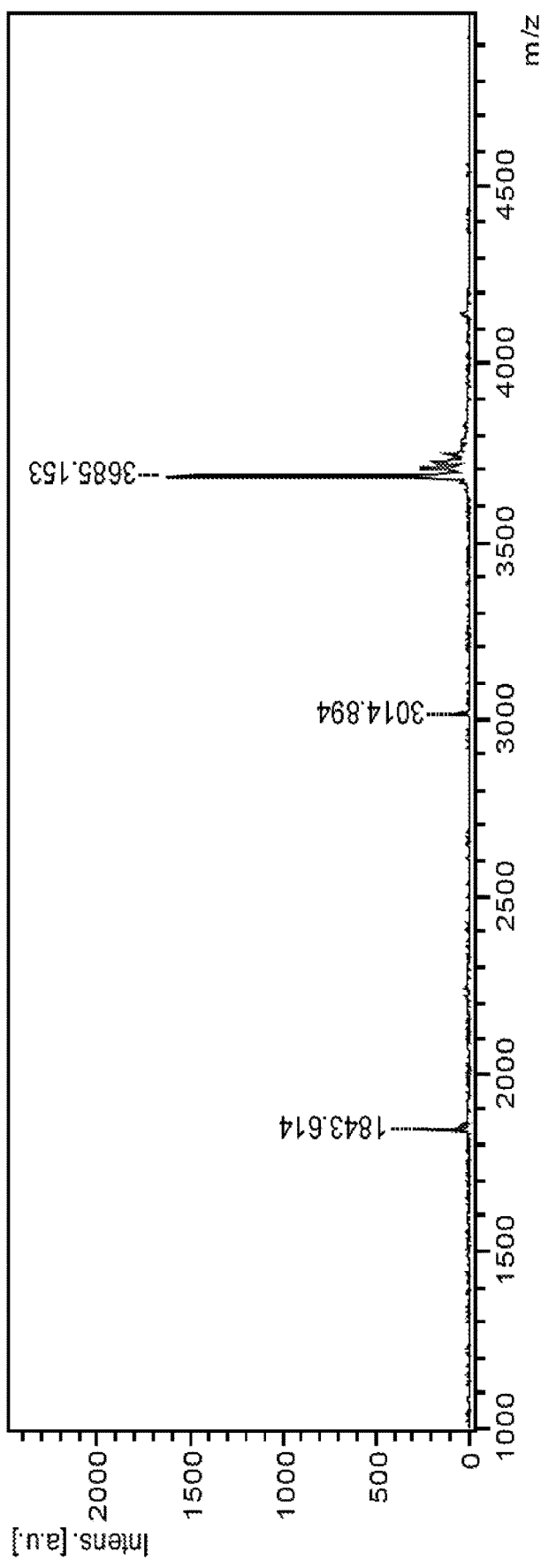
Figure 19:
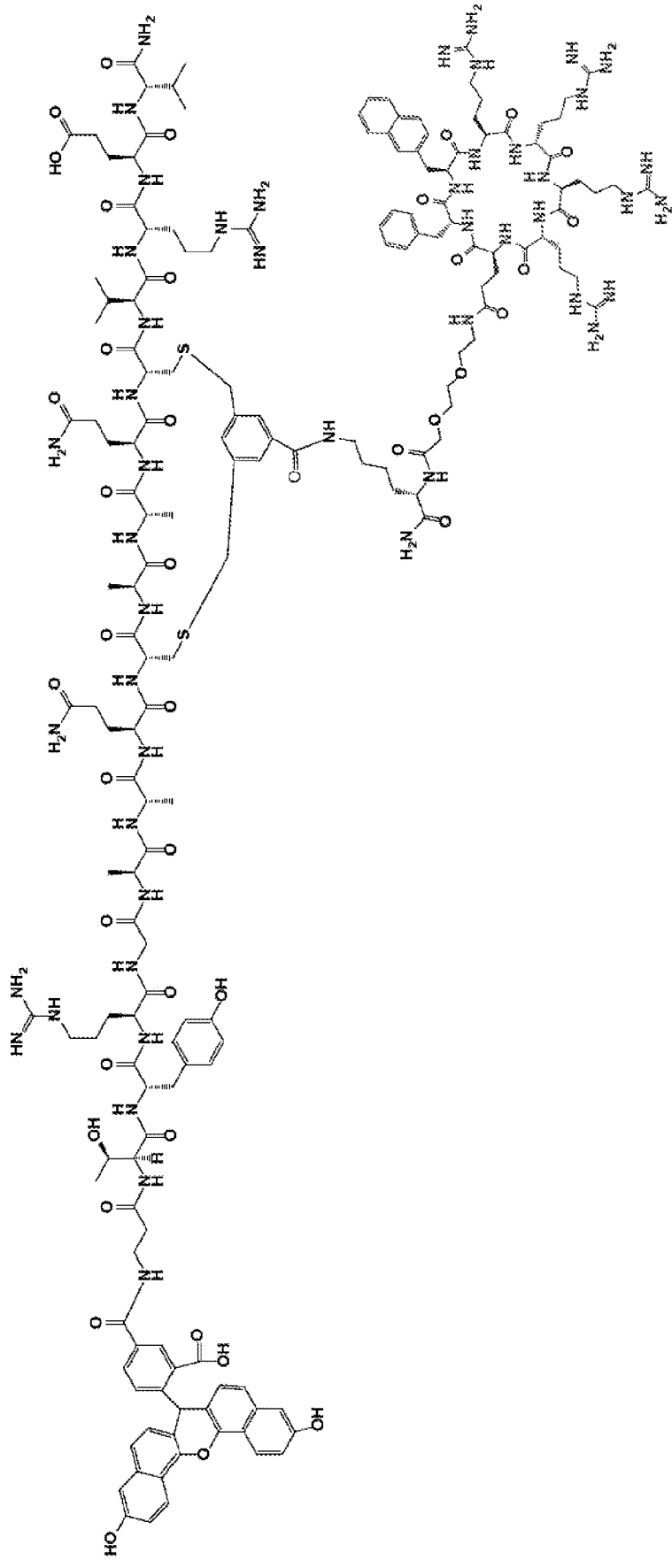
FIG. 19 shows the chemical structure of a stapled, labeled peptide 21, which has been conjugated to a cCPP via a linker, and HPLC chromatograms.
Figure 19:
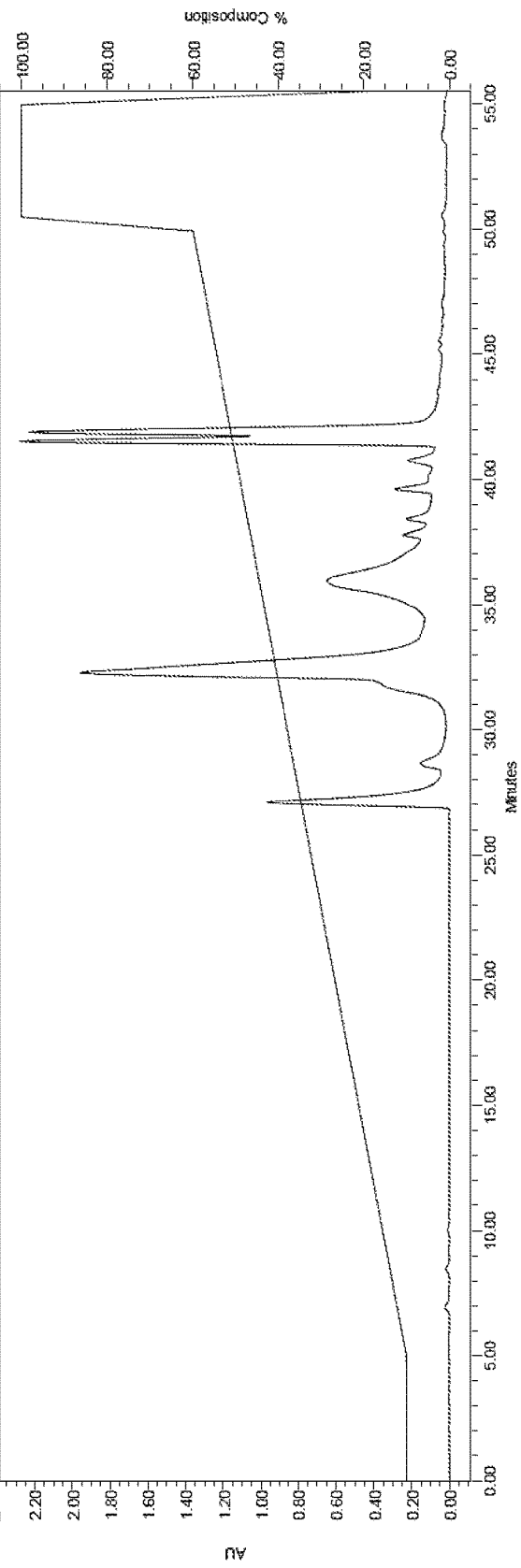
Figure 19:
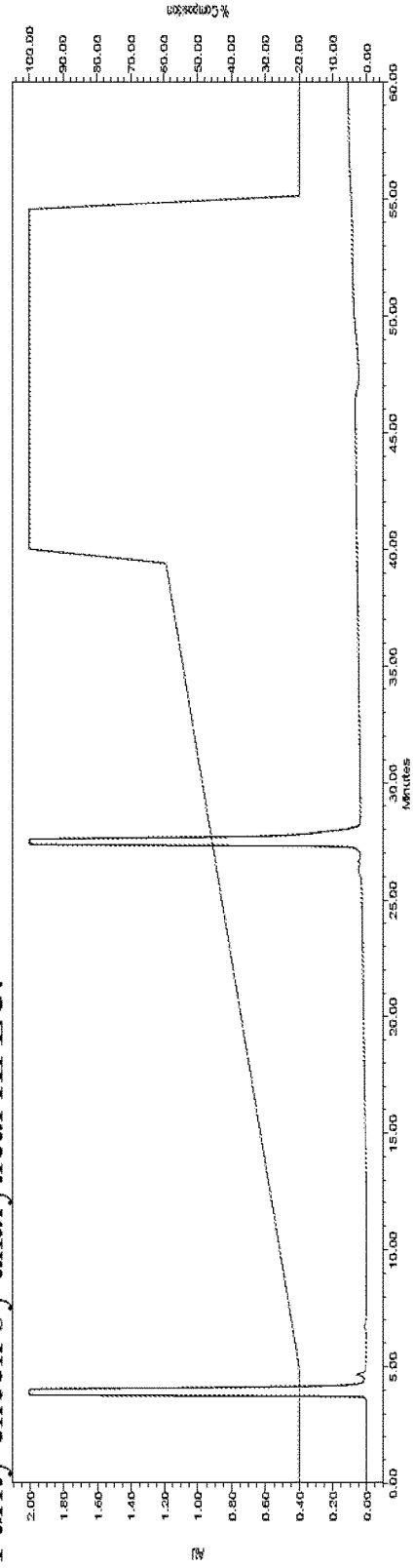
Figure 20A:
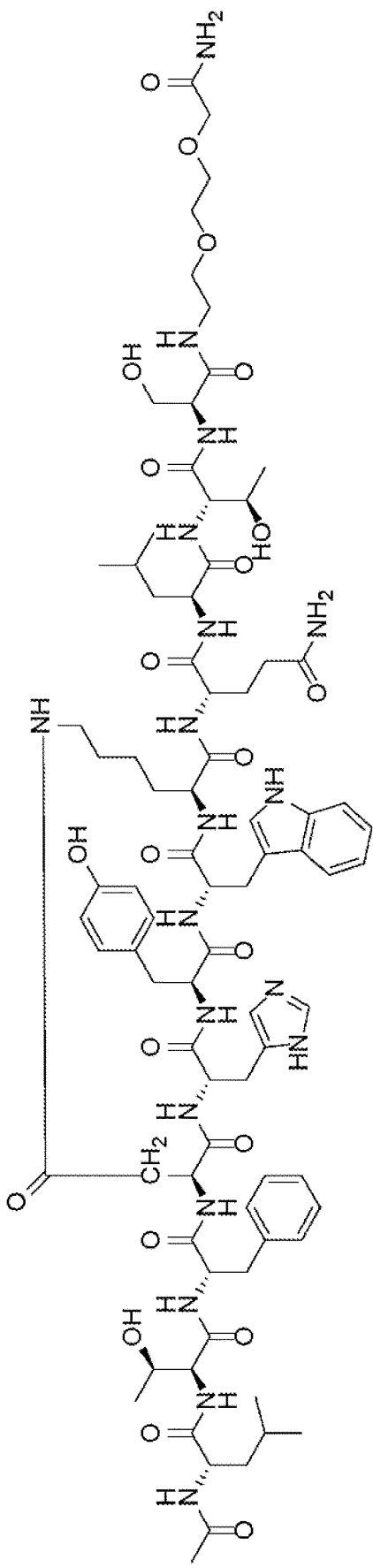
FIGS. 20A-20D shows the chemical structures of amide stapled peptides and conjugates, including sPDI peptide 22 (FIG. 20A), CPP9-sPDI peptide conjugate 23 (FIG. 20B), R9-sPDI peptide conjugate 24 (FIG. 20C), and Tat-sPDI peptide conjugate 25 (FIG. 20D). CPP9, R9, and Tat are each conjugated to the peptide via a linker attached to the C-terminus.
Figure 20B:
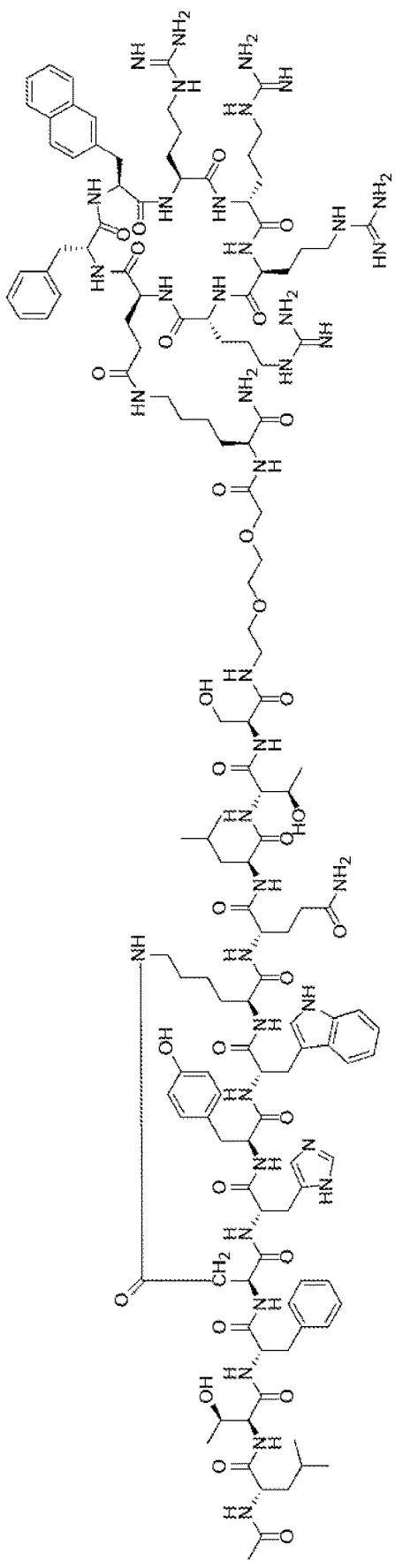
Figure 20C:
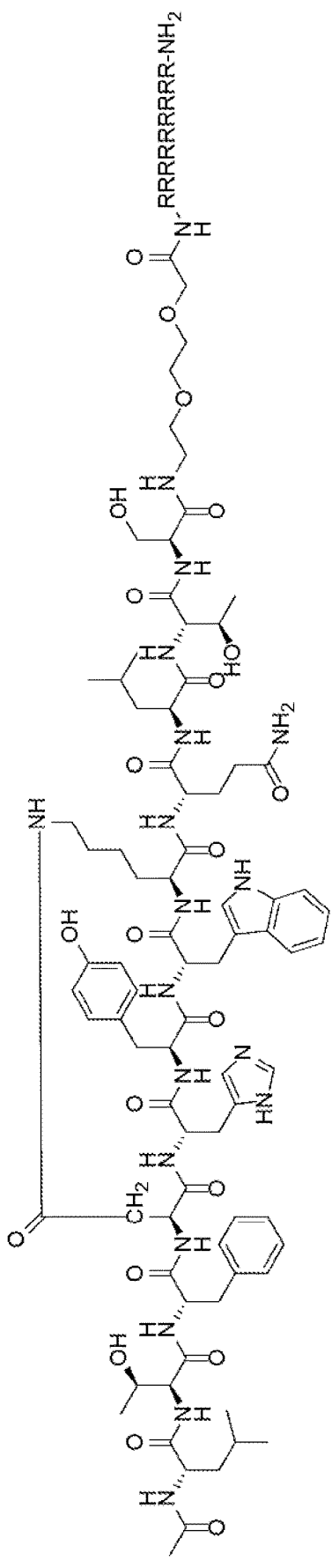
Figure 20D:
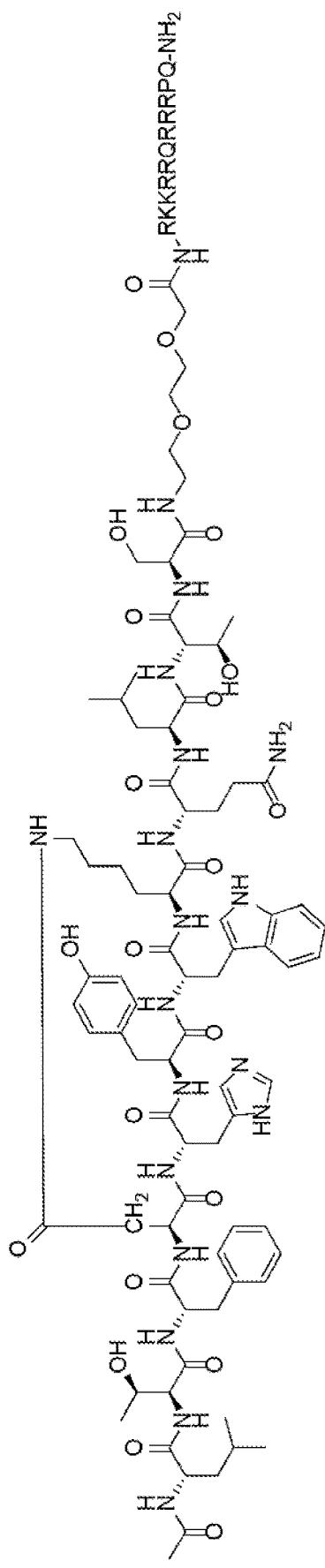

We chose a previously reported MDM2 ligand, Ac-LT-FEHYWAQLTS (SEQ ID NO:1) ("PDI"; see Phan, J., et al., J. Biol. Chem. 285, 2174-2183 (2010)), and labeled at its C-terminus with fluorescein isothiocyanate (FITC) via a miniPEG-Lys linker. The FITC-labeled peptide (Table 5, peptide 1) bound to MDM2 with a $K_D$ value of 80 nM, similar to the reported values. For stapling, we replaced Glu-4 and Ala-8 or His-5 and Gln-9 with homocysteine residues, respectively and stapled the two resulting peptides with DCA as described above (Table 5, peptides 2 and 3). Peptides 2 and 3 bound to MDM2 with $K_D$ values of 144 and 171 nM, respectively. Because of its somewhat higher potency, peptide 2 was selected for conjugation with CPP9 as described above, to give two stereoisomers, peptides 4 and 5, which were separated by HPLC (FIG. 5) although their actual Z/E configuration at the oxime moiety was not determined. The binding affinity of peptides 4 and 5 for MDM2 was determined by examining their ability to compete with FITC-labeled peptide 1 for binding to MDM2 in a fluorescence anisotropy (FA)-based assay. Peptides 4 and 5 showed $IC_{50}$ values of 220 and 201 nM, respectively (Table 1), suggesting that conjugation to CPP9 does not significantly affect the binding of the stapled peptides to MDM2.

TABLE 5

Sequences and Potency of Peptidyl MDM2 Ligands

| Structure/ Peptide ID | Sequence[a] (C term to N term) | $K_D$ or $IC_{50}$ (nM) |
|---|---|---|
| 1 | Ac-L-T-F-E-H-Y-W-A-Q-L-T-S-miniPEG-K-(dye) | 80 ± 10 |
| 2 | Ac-L-T-F-homoC-H-Y-W-homoC-Q-L-T-S-miniPEG-K-(dye) <br> └─DCA─┘ | 144 ± 28 |
| 3 | Ac-L-T-F-E-homoC-Y-W-A-homoC-Q-L-T-S-miniPEG-K-(dye) <br> └─DCA─┘ | 171 ± 36 |
| 4 | Ac-L-T-F-homoC-H-Y-W-homoC-Q-L-T-S-miniPEG-K <br> └─DCA─┘ <br> ⋮cCPP | 220 ± 19 |
| 5 | Ac-L-T-F-homoC-H-Y-W-homoC-Q-L-T-S-miniPEG-K <br> └─DCA─┘ <br> ⋮cCPP | 201 ± 12 |

[a]miniPEG, 8-amino-3,6-dioxaoctanoic acid; homoC, homocysteine; DCA, 1,3-dichloroacetone. Reported values are $K_D$ values for FITC-peptides 1-3 and $IC_{50}$ values for unlabeled peptides 4 and 5.

Figure 2:
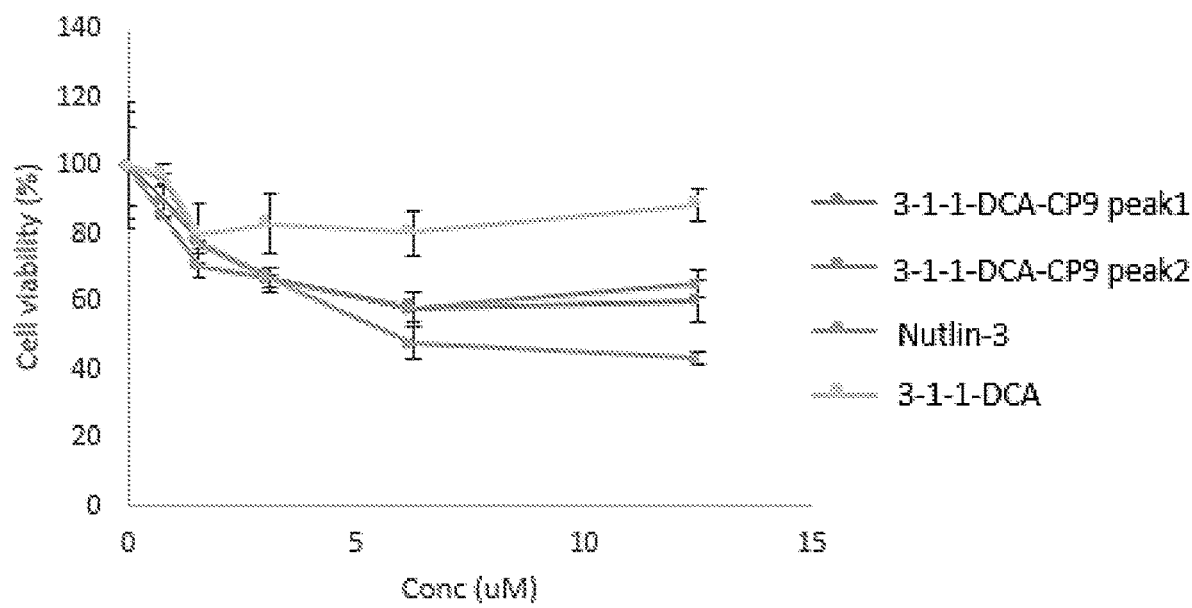
FIG. 2 is a survival curve, showing the effect of stapled peptide 2 (3-1-1-DCA), CPP9-stapled peptide conjugates 4 and 5 (3-1-1-DCA-CP9 peak1 and peak2), and nutlin-3 on the viability of wild type p53 cell line (HCT116 WT) and the p53 knockout cell line (HCT116 p53−/−).
Figure 2:
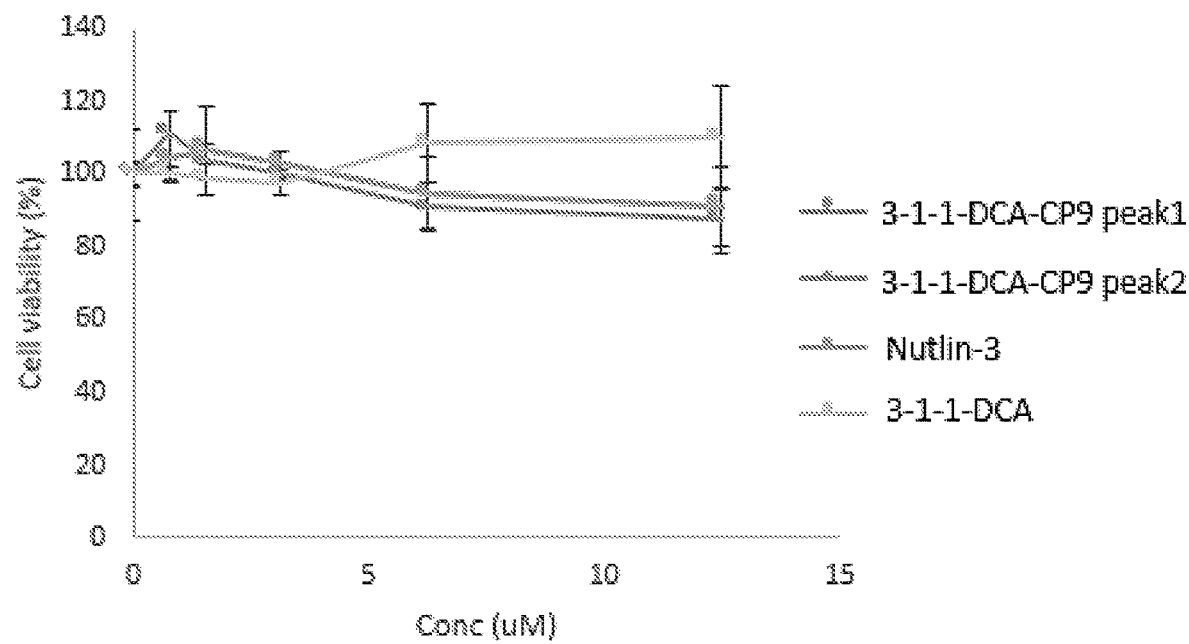

Peptides 4 and 5 were tested for anticancer activity against human colon carcinoma cell lines harboring WT (HCT116 p53+/+) and mutant p53 genes (HCT116 p53-/-) using the MTT viability assay. Peptides 4 and 5 dose-dependently reduced the viability of WT p53 cells, but not p53 mutant cells (FIG. 2). Nutlin-3, a small-molecule inhibitor of MDM2, also selectively killed the WT p53 cells in a dose-dependent manner, as previously reported. See Vassilev, L. T., et al., *Science*, 303, 844-848 (2004).

On the other hand, the stapled peptide without CPP9 (peptide 2) showed no significant effect against either cell line, presumably because it cannot penetrate the cell membrane (see below).

Figure 3A:
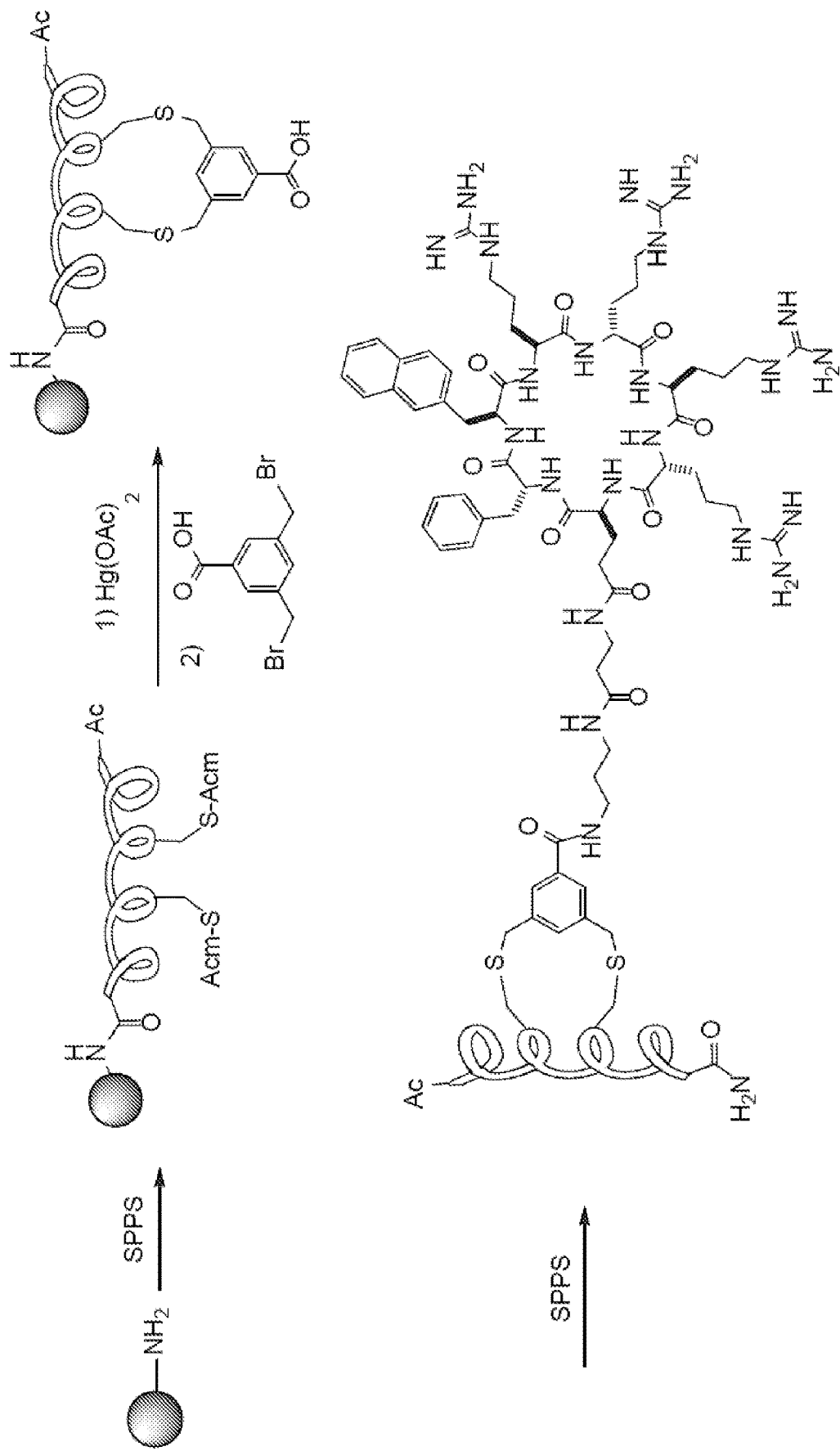
FIGS. 3A-3B is a schematic showing two different strategies for synthesizing cCPP-stapled peptide conjugates with BBA as the staple/linker.

Example 3: Peptide Stapling and Conjugation with 3,5-Bis(Bromomethyl)Benzoic Acid The main limitation of the oxime-based conjugation method is the formation of two different stereoisomers, which complicates product isolation and further clinical development. To overcome this limitation, we next employed 3,5-bis(bromomethyl)benzoic acid ("BBA") as the stapling agent. A structurally similar compound, m-xylene dibromide, has previously been used to staple alpha-helical peptides. See Jo, H., et al., *J Am Chem Soc.* 134, 17704-17713 (2012). m-Xylene dibromide reacts rapidly with two cysteines within spatial proximity to form a single stapled peptide product with high yields and at a low reagent/peptide stoichiometry. We developed two methods to staple/conjugate alpha-helical peptides with BBA. In the first method (FIG. 3A), a cargo peptide containing two acetamidomethyl (Acm)-protected cysteines is first synthesized on solid support by standard solid-phase peptide synthesis (SPPS). The Acm groups are removed with $Hg(OAc)_2$ and the exposed free thiols are alkylated with BBA. While still on resin, the benzoic acid group is reacted with an N-Fmoc-1,3-diaminopropane linker in the presence of a coupling agent (e.g., HATU) to generate an amine moiety, which serves as an handle for subsequent synthesis of beta-Ala-CPP9 by SPPS.

Figure 3B:
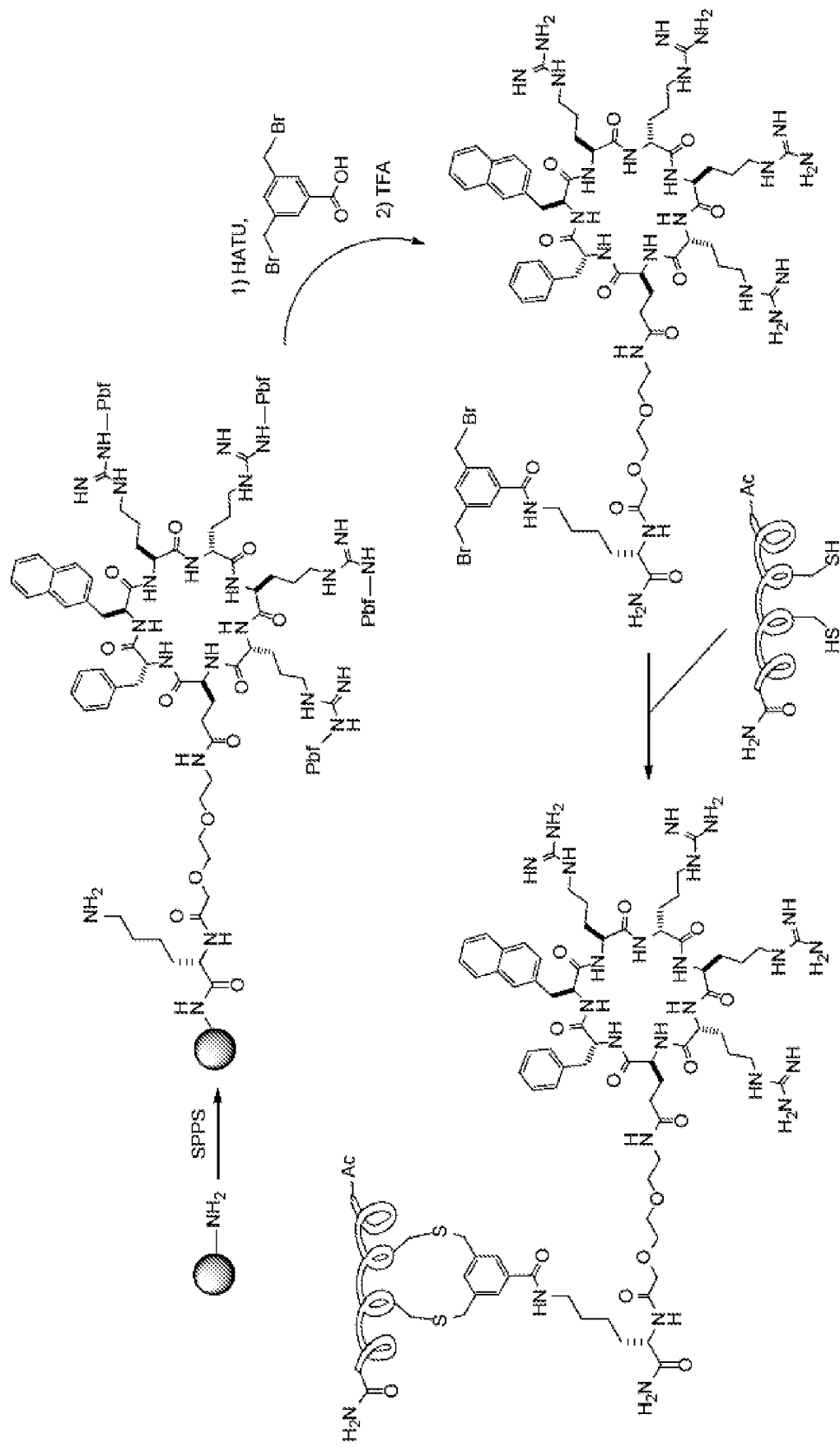

In the second method (FIG. 3B), CPP9 is synthesized on solid phase with a miniPEG-Lys(Mtt) linker. The Mtt group on the lysine side chain is selectively removed with 5% TFA and the exposed amine is coupled to BBA by using HATU as the coupling agent. Cleavage from resin and side chain deprotection by TFA followed by HPLC purification gives the BBA-derivatized CPP9, which is then conjugated to a fully deprotected cysteine-containing peptide by simply mixing the two peptides in a neutral aqueous solution.

The advantage of the first method is that the entire CPP-stapled peptide conjugate can be synthesized on the solid phase and the product only needs to be purified once. The second method, on the other hand, is modular and convergent, and can be applied to rapidly generate a large number of different CPP/cargo combinations for testing in order to identify the optimal CPP-cargo conjugate(s).

Example 4: CPP9 Confers Consistent Cell-Permeability to Stapled Peptides

We applied the stapling/conjugation method (FIG. 3B) to the known MDM2 ligand, Ac-LTFEHYWAQLTS (SEQ ID NO:1) ("PDI"). See Hu, B., et al., *Cancer Res.* 67, 8810-8817 (2007). The Glu-4 and Ala-8 residues were replaced with cysteine (peptides 6 and 7) or homocysteine (peptides 8 and 9) and the resulting peptides were stapled with BBA and conjugated to CPP9 (Table 2, peptides 7 and 9). As controls (without CPP), we also stapled the peptides with m-xylene dibromide to give a neutral hydrophobic staple (peptides 6 and 8). The cytosolic entry efficiencies of the peptides were assessed by labeling their C-termini with 5(6)-carboxynaphthofluorescein (NF) through a flexible miniPEG-Lys linker and quantitating the intracellular fluorescence by flow cytometry. With a pKa of 7.8, NF is fluorescent in the neutral environments of the cytosol and nucleus (pH 7.4) but has minimal fluorescence in the acidic endosome/lysosome (pH≤6.0). As expected, both CPP9 conjugated peptides (peptides 7 and 9) were readily cell-permeable, having cytosolic entry efficiencies of 497% and 30% relative to that of CPP9 (100%), one of the most active CPPs reported to date. Unfortunately, the unconjugated peptides 6 and 8 were poorly soluble and their cellular uptake efficiencies could not be reliably determined. To increase the aqueous solubility, we replaced the N-terminal leucine of peptide 6 with a glutamate to give peptide 10, and added a second glutamate residue to the N-terminus of peptide 10 to produce peptide 12 (Table 6). Conjugation of peptides 10 and 12 with CPP9 generated peptides 11 and 13, respectively. Remarkably, while treatment of HeLa cells with 5 µM peptide 10 or 12 (no CPP) for 2 h at 37° C. resulted in minimal cellular uptake (2.8% for both), conjugation of the peptides with CPP9 increased their cytosolic entry efficiency by 48- and 86-fold, respectively (Table 6, peptides 11 and 13).

To test whether the dramatic improvement in cell-permeability is general for other stapled peptides, we synthesized four additional pairs of stapled peptides, with and without conjugation to CPP9, and compared their cytosolic entry efficiencies (Table 6, peptides 14-21). After analyzing more than 200 stapled peptides, Verdine and co-workers previously reported peptide 14 as one of the most cell-permeable stapled peptides, whereas peptides 16, 18, and 20 as among the least permeable ones. See Chu, Q., *Med. Chem. Commun.* 6, 111-119 (2015). In agreement with Verdine's finding, xylene-stapled peptide 14 (no CPP) demonstrated excellent cell-permeability (47% of CPP9), whereas peptides 16 and 18 did not (2.5% and 8.9%, respectively). The cellular entry efficiency of peptide 20 could not be determined due to limited solubility. Again, after conjugation with CPP9, all four peptides (15, 17, 19, and 21) were highly cell-permeable, showing 11- to 152-fold improvement over their unconjugated counterparts. The variation in cell-permeability among the CPP9 conjugated peptides (30-508%) is likely at least partially caused by differential binding to serum proteins (all flow cytometry experiments in this work were conducted in the presence of 10% fetal bovine serum). In general, hydrophobic cargoes are prone to binding to serum proteins and/or aggregation, resulting in greater reduction in the cellular uptake efficiency.

Figure 4:
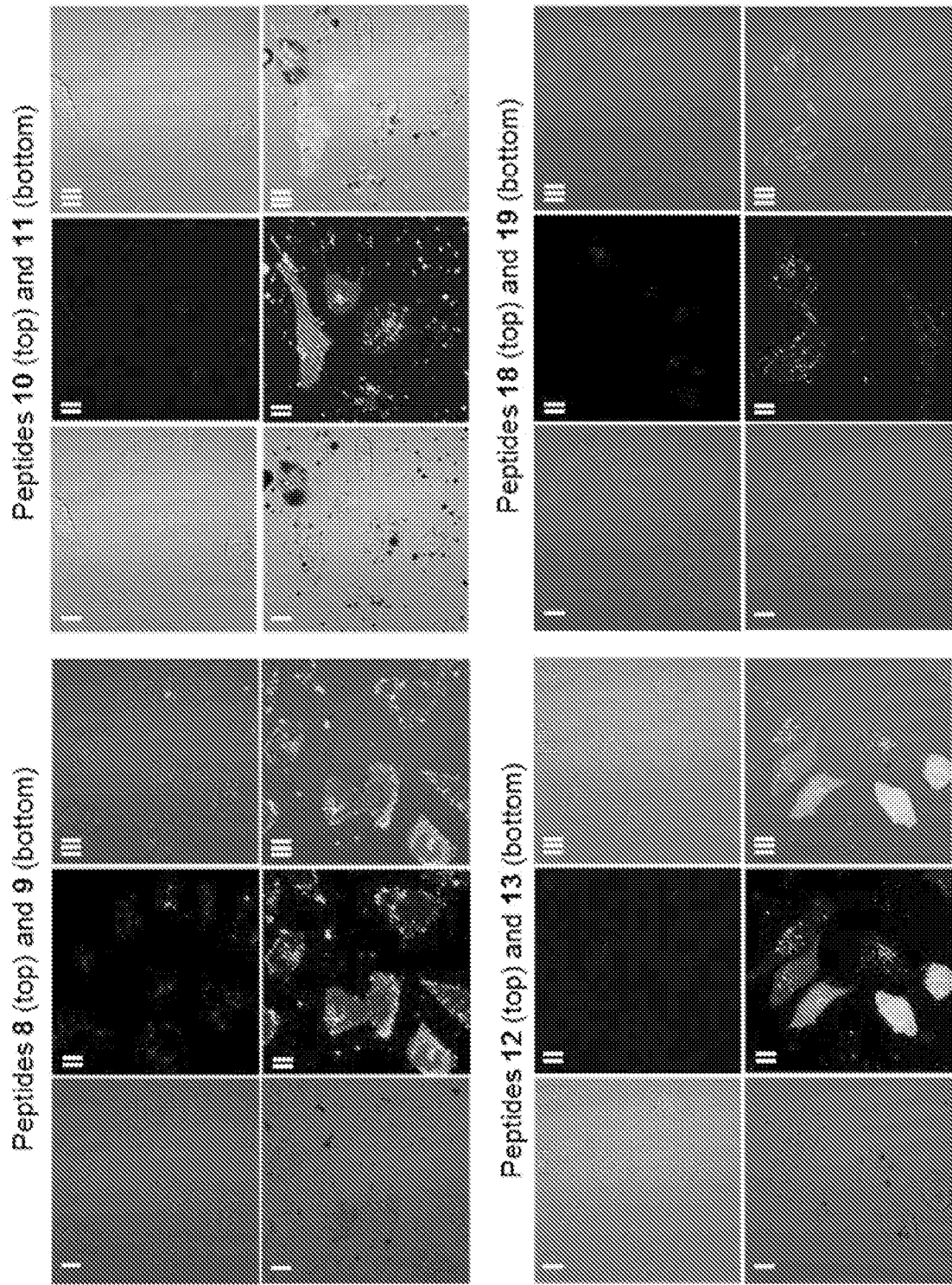
FIG. 4 shows a comparison of the cellular entry efficiency of stapled peptides with and without CPP9 conjugation. HeLa cells were treated with 5 µM FITC-labeled peptide for 2 h at 37° C., washed to remove excess peptide, and subjected to live-cell confocal microscopy. I, DIC; II, GFP channel; and III, overlap of I and II.

Four pairs of the peptides from Table 6 were also labeled with FITC and their entry into HeLa cells were monitored by live-cell confocal microscopy (FIG. 4). In all four cases, the stapled peptides alone (no CPP) showed minimal uptake, whereas the CPP9-peptide conjugates entered the cells efficiently. Consistent with the flow cytometry data, diffuse fluorescence was present throughout the entire cell volume, indicating that a significant fraction of the endocytosed peptides escaped from the endosomes into the cytosol and nucleus. Taken together, our data suggest that conjugation to a cCPP (e.g., CPP9) is capable of endowing stapled peptides with high and consistent cell-permeability.

TABLE 6

Sequences and cytosolic entry efficiencies of stapled alpha-helical peptides with and without conjugation to CPP9

| Structure/ Peptide ID | Sequence$^a$ (C term to N term) | Staple | Cellular Uptake (MFI$^{NF}$, %)$^b$ |
|---|---|---|---|
| CPP9 | cyclo(f-Φ-R-r-R-r-Q)-miniPEG-K(NF)-NH$_2$ | N/A | 100 |
| 6 | Ac-<u>LTFCHYWCQLTS</u>-miniPEG-K(NF)-NH$_2$ (SEQ ID NO: 40, underlined portion only) | xylene | ND |
| 7 | Ac-<u>LTFCHYWCQLTS</u>-miniPEG-K(NF)-NH$_2$ (SEQ ID NO: 40, underlined portion only) | BBA-CPP9 | 497 ± 22 |
| 8 | Ac-<u>LTFhCHYWhCQLTS</u>-miniPEG-K(NF)-NH$_2$ (SEQ ID NO: 41, underlined portion only) | xylene | ND |
| 9 | Ac-<u>LTFhCHYWhCQLTS</u>-miniPEG-K(NF)-NH$_2$ (SEQ ID NO: 41, underlined portion only) | BBA-CPP9 | 30 ± 5 |
| 10 | Ac-<u>ETFCHYWCQLTS</u>-miniPEG-K(NF)-NH$_2$ (SEQ ID NO: 42, underlined portion only) | xylene | 2.8 ± 0.1 |
| 11 | Ac-<u>ETFCHYWCQLTS</u>-miniPEG-K(NF)-NH$_2$ (SEQ ID NO: 42, underlined portion only) | BBA-CPP9 | 135 ± 46 |
| 12 | Ac-<u>EETFCHYWCQLTS</u>-miniPEG-K(NF)-NH$_2$ (SEQ ID NO: 43, underlined portion only) | xylene | 2.8 ± 0.5 |
| 13 | Ac-<u>EETFCHYWCQLTS</u>-miniPEG-K(NF)-NH$_2$ (SEQ ID NO: 43, underlined portion only) | BBA-CPP9 | 242 ± 17 |
| 14 | NF-βA-<u>RKFCRLFC</u>-NH$_2$ (SEQ ID NO: 44, underlined portion only) | xylene | 47 ± 9 |
| 15 | NF-βA-<u>RKFCRLFC</u>-NH$_2$ (SEQ ID NO: 44, underlined portion only) | BBA-CPP9 | 508 ± 214 |
| 16 | NF-βA-<u>ENPECILDCHVQRVM</u>-NH$_2$ (SEQ ID NO: 45, underlined portion only) | xylene | 2.5 ± 0.5 |
| 17 | NF-βA-<u>ENPECILDCHVQRVM</u>-NH$_2$ (SEQ ID NO: 45, underlined portion only) | BBA-CPP9 | 381 ± 129 |
| 18 | NF-βA-<u>NPECILDCHVQRVM</u>-NH$_2$ (SEQ ID NO: 46, underlined portion only) | xylene | 8.9 ± 2.9 |
| 19 | NF-βA-<u>NPECILDCHVQRVM</u>-NH$_2$ (SEQ ID NO: 46, underlined portion only) | BBA-CPP9 | 112 ± 21 |
| 20 | NF-βA-<u>TYRGAAQCAAQCVREV</u>-NH$_2$ (SEQ ID NO: 47, underlined portion only) | xylene | ND |
| 21 | NF-βA-<u>TYRGAAQCAAQCVREV</u>-NH$_2$ (SEQ ID NO: 47, underlined portion only) | BBA-CPP9 | 83 ± 8 |

$^a$Φ, L-2-naphthylalanine; βA, beta-alanine; r, D-arginine; NF, 5(6)-carboxynaphthofluorescein; hC, homocysteine; BBA, 3,5-dimethylbenzoyl; miniPEG, 8-amino-3,6-dioxaoctanoic acid.
$^b$All values reported are relative to that of CPP9, which is defined as 100%. ND, not determined due to limited aqueous solubility.

Example 5: Biochemical and Biological Activity of Stapled Peptides

Peptides 6-13, which were variants of the MDM2 ligand PDI, were tested for binding to MDM2. Replacement of Glu-4 and Ala-8 residues with cysteine and stapling with BBA decreased the MDM2-binding affinity by ~2.5-fold ($K_D$=80 and 190 nM for peptides 1 and 6, respectively). Conjugation with CPP9 further reduced the MDM2 binding affinity by ~2-fold ($K_D$~300 nM for peptide 7) (Table 7). Substitution of homocysteine for Glu-4 and Ala-8 followed by BBA stapling improved the MDM2 binding affinity by 5-fold ($K_D$=14 nM for peptide 8), but further conjugation with CPP9 decreased the affinity by ~8-fold ($K_D$=114 nM for peptide 9). Replacement of Leu-1 with Glu improved the binding affinity of peptide 6 by 5-fold ($K_D$=36 nM for peptide 10), likely by engaging in electrostatic interactions with the positively charged MDM2 surface near the N-terminus of the peptide ligand. Again, conjugation with CPP9 reduced MDM2 binding affinity by 6-fold ($K_D$=225 nM for peptide 11). Addition of a second Glu at the N-terminus of peptide 11, however, did not further improve the binding affinity ($K_D$=365 nM peptide 13).

TABLE 7

MDM2 binding affinity of BBA-stapled alpha-helical peptides

| Structure/ Peptide ID | Sequence[a] (C term to N term) | Staple | $K_D$ (nM) |
|---|---|---|---|
| 1 | Ac-LTFEHYWAQLTS-miniPEG-K(FITC)-NH$_2$ (SEQ ID NO: 1, underlined portion only) | none | 80 ± 10 |
| 6 | Ac-LTFCHYWCQLTS-miniPEG-K(FITC)-NH$_2$ (SEQ ID NO: 40, underlined portion only) | BBA | 190 ± 150 |
| 7 | Ac-LTFCHYWCQLTS-miniPEG-K(FITC)-NH$_2$ (SEQ ID NO: 40, underlined portion only) | BBA-CPP9 | ~300 |
| 8 | Ac-LTFhCHYWhCQLTS-miniPEG-K(FITC)-NH2 (SEQ ID NO: 41, underlined portion only) | BBA | 15 ± 9 |
| 9 | Ac-LTFhCHYWhCQLTS-miniPEG-K(FITC)-NH$_2$ (SEQ ID NO: 41, underlined portion only) | BBA-CPP9 | 114 ± 19 |
| 10 | Ac-ETFCHYWCQLTS-miniPEG-K(FITC)-NH$_2$ (SEQ ID NO: 42, underlined portion only) | xylene | 36 ± 8 |
| 11 | Ac-ETFCHYWCQLTS-miniPEG-K(FITC)-NH$_2$ (SEQ ID NO: 42, underlined portion only) | BBA-CPP9 | 225 ± 19 |
| 12 | Ac-EETFCHYWCQLTS-miniPEG-K(FITC)-NH$_2$ (SEQ ID NO: 43, underlined portion only) | xylene | 187 ± 37 |
| 13 | Ac-EETFCHYWCQLTS-miniPEG-K(FITC)-NH$_2$ (SEQ ID NO: 43, underlined portion only) | BBA-CPP9 | 365 ± 82 |

[a]hC, homocysteine; BBA, 3,5-dimethylbenzoyl; miniPEG, 8-amino-3,6-dioxaoctanoic acid.

Example 6: Cytosolic Delivery of a Stapled Peptide Conjugated to Various Peptide Transduction Domains (PTD)

A series of stapled peptide conjugates were evaluated to compare the ability of different peptide transduction domains (PTD) to effect cytosolic delivery of the stapled MDM2 inhibitor sPDI (FIG. 20A-20D). Structure 22 shows that the PDI sequence is stapled by an amide group that forms between an aspartic acid and lysine residue. Each of the conjugates (FIG. 20B-20D) further contains a C-terminus linker that is attached to either CPP9 (structure 23), R$_9$ (structure 24), or Tat (structure 25).

Figure 21:
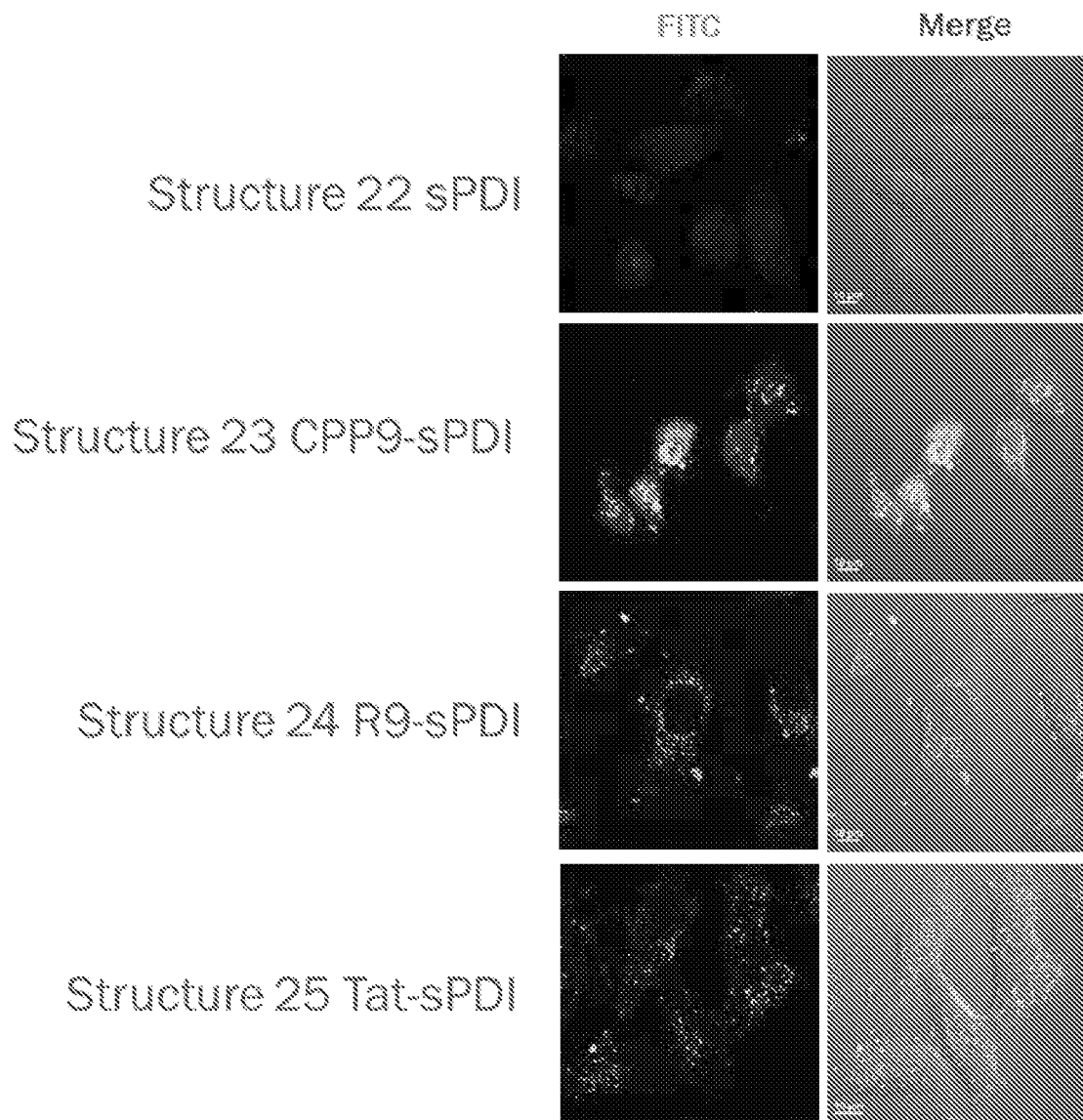
FIG. 21 shows a comparison of the cellular entry efficiency of stapled peptides with and without conjugation. Images are provided from structure 22 (sPDI), structure 23 (CPP9-sPDI), structure 24 (R9-sPDI), and structure 25 (Tat-sPDI). Analogs with Lys (FITC) at the N-terminus were used for confocal imaging.

To assess delivery aptitude of each conjugate, peptides 22-25 were labeled with FITC and their entry into HeLa cells was monitored by live-cell confocal microscopy (FIG. 21). HeLa cells were treated with 5 μM FITC-labeled peptide for 2 h at 37° C. and washed to remove excess peptide. The images obtained after treatment show that the stapled peptide alone (structure 22) had minimal uptake, whereas the conjugates entered the cells to varying degrees. The most effective conjugate for delivering sPDI was the CPP9-conjugated peptide 23. While R$_9$ and Tat were able to deliver the MDM2 inhibitor to the cytosol, efficiency was noticeably decreased. This data again suggests that conjugation to a cCPP (e.g., CPP9) is capable of endowing stapled peptides with high and consistent cell-permeability.

Example 7: Functional Delivery of the Stapled MDM2 Inhibitor sPDI Conjugated to CPP9

A cell-free competition assay measuring fluorescence polarization was used to determine how effectively CPP9 is able to deliver the stapled MDM2 inhibitor to the target. In this study, sPDI effectively inhibited MDM2 as a function of competitor peptide concentration with an IC$_{50}$ of 98.4 nM. CPP9-sPDI also acts as an effective inhibitor, showing improved activity with an IC$_{50}$ of 63.3 nM. Without being bound by any particular theory, for the conjugate to be active, it has to deliver the sPDI peptide to MDM2 without interference from other moieties. The results indicate that CPP9-sPDI is configured in such a way that interactions between sPDI and MDM2 are not disturbed. This is not the case for the F10A mutant where activity is substantially diminished—a finding that confirms the importance of the peptide sequence for MDM2 inhibition.

Example 8: Evaluation of the Anti-Proliferative Effects of CPPS9-sPDI

Figure 22:
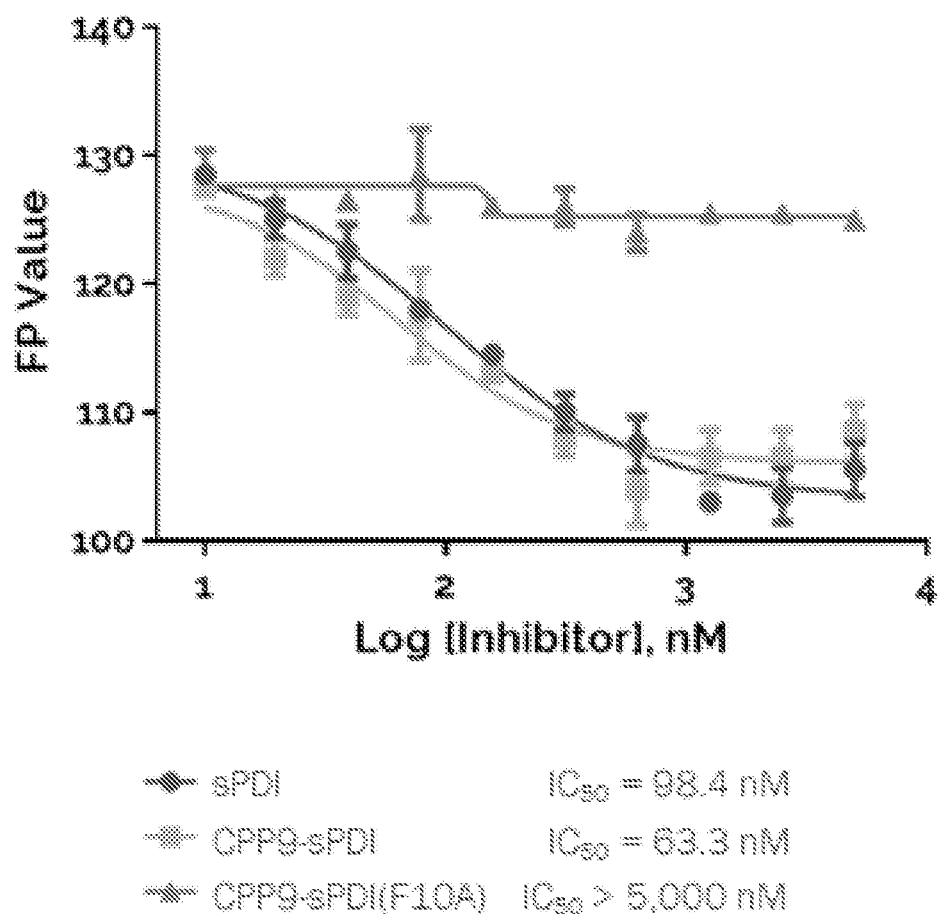
FIG. 22 shows a graph for a cell free competition assay comparing the functional cytosolic delivery of sPDI (structure 22), CPP9-sPDI (structure 23), and CPP9-sPDI F10A mutant. The data for the fluorescence polarization (FP) plot was obtained using FITC-labeled MDM2 ligand (15 nM) in the presence of MDM2 (15 nM) and unlabeled sPDI, CPP9-conjugated stapled PDI (CPP9-sPDI; structure 23), or CPP9-sPDI F, 10A mutant (0-5 µM) as a function of competitor peptide concentration.
Figure 23:
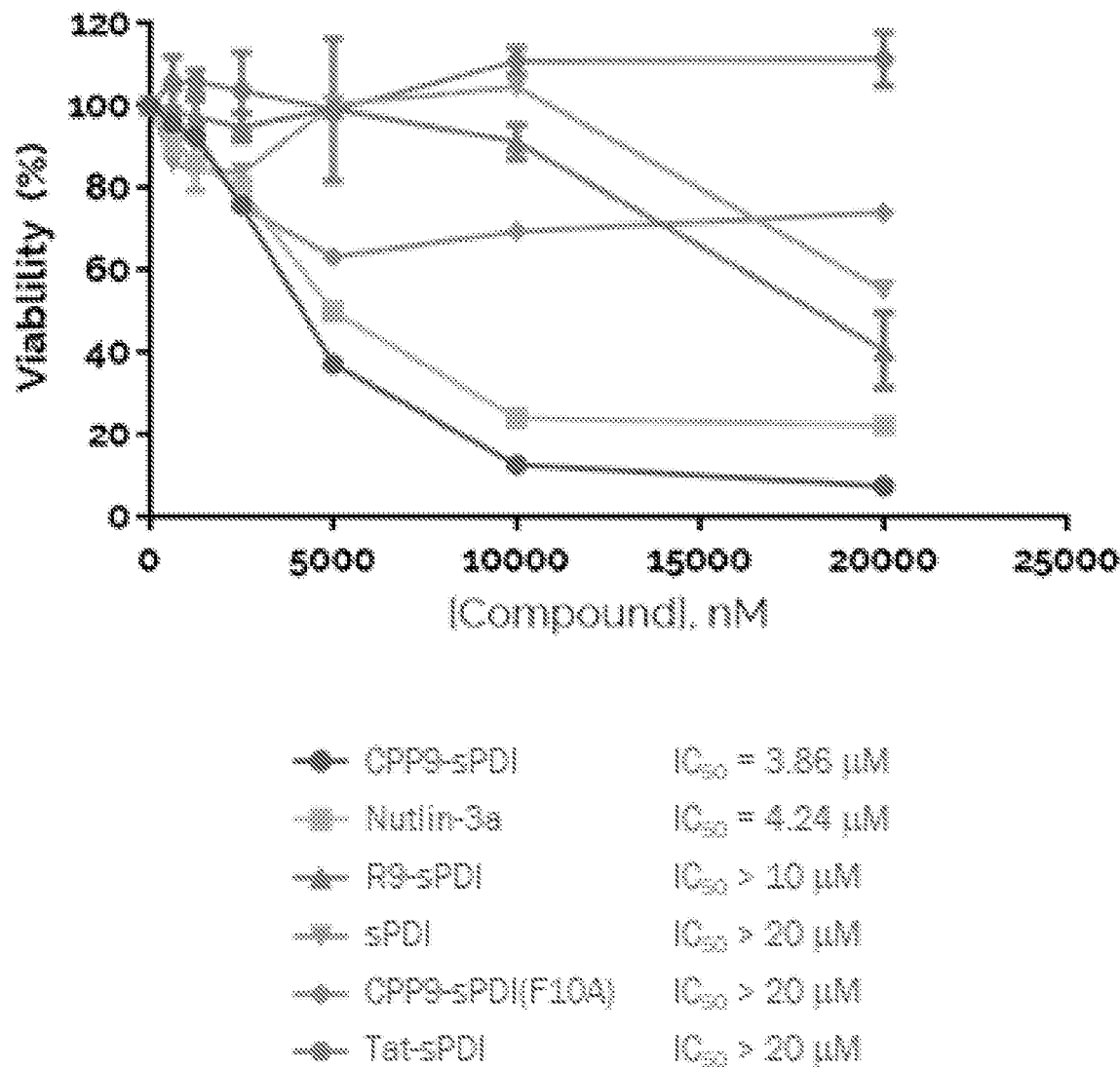
FIG. 23 shows a graph for an anti-proliferation assay comparing the effect of 72-hour treatment with CPP9-sPDI (structure 23), Nutlin-3a, R9-sPDI (structure 24), sPDI (structure 22), CPP9-sPDI(F10A) and Tat-sPDI (structure 25, 0-20 µM) on the viability of SJSA-1 cell line in the presence of 10% FBS as measured by MTT assay. $IC_{50}$ values (µM) are provided for each test compound.

In addition, the anti-proliferative effects of CPP9-sPDI (structure 23) were evaluated. FIG. 23 compares the effects of CPP9-sPDI, Nutlin-3a, R$_9$-sPDI, sPDI, CPP9-sPDI (F10A) and Tat-sPDI (0-20 μM) on the viability of SJSA-1 cell line after 72-hour treatment in the presence of 10% FBS as measured by MTT assay. In comparison to known MDM2 inhibitor Nutlin-3a, CPP9-sPDI showed an enhancement in cytotoxicity with an IC$_{50}$ value of 3.86 M. The other conjugates had substantially less activity (>20 M), which reveals that PTDs such as R$_9$ and Tat less effectively deliver the inhibitor to the target. The F10A peptide mutant resulted in a greater than 5-fold decrease in cytotoxicity compared to CPP9-sPDI; a finding that reinforces that MDM2 is inhibited by sPDI, and not CPP9 or fragment thereof. Notably, sPDI also possessed substantially diminished cytotoxicity, even though this peptide showed comparable effects to CPP9-sPDI in the cell-free binding assay (FIG. 22).

Figure 24:
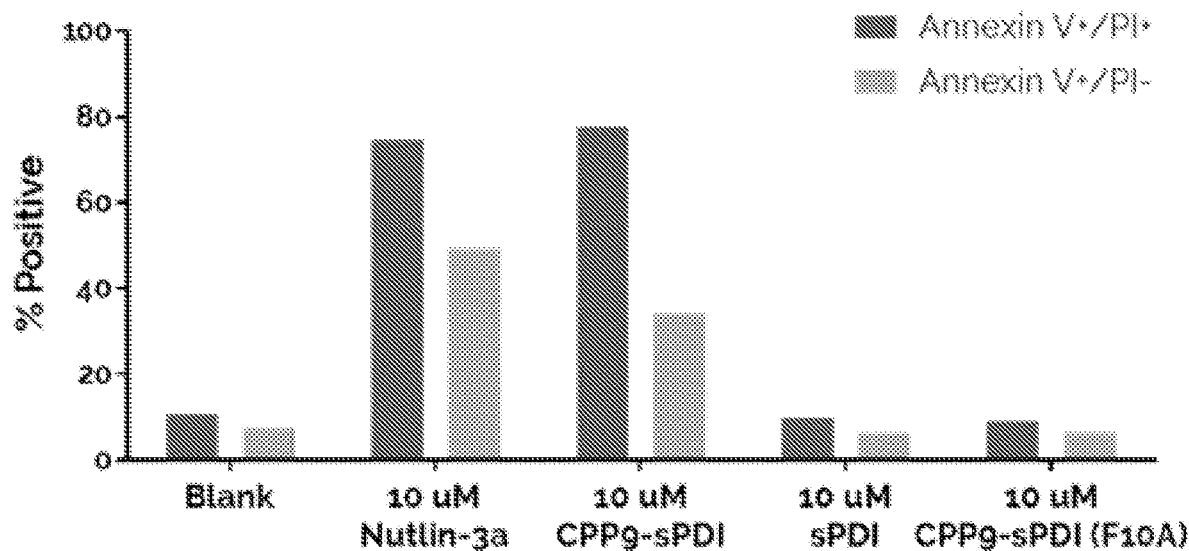
FIG. 24 is a graph showing that the anti-proliferative activity of CPP9-sPDI (structure 23) is mediated by apoptotic pathways. The percentage of Annexin V+/PI+ and Annexin V+/PI− SJSA-1 cells after 48-hour treatment of inhibitors in presence of 10% FBS was measured.

The mode of action (MOA) of CPP9-sPDI upon cytosolic delivery of the MDM2 inhibitor was also considered. Using a flow cytometry assay for detecting annexin V+/propidium iodide$^+$ (PI$^+$) SJSA-1 cells, the graph of FIG. 24 shows that the anti-proliferative activity of CPP9-sPDI is mediated by apoptotic pathways. This behavior is similar to Nutlin-3a, which is known to induce p53-dependent apoptosis in certain cancer cell lines. In this study, the percentage of Annexin V+/PI+ and Annexin V+/PI− SJSA-1 cells is determined after 48-hour treatment of inhibitors in presence of 10% FBS.

Figure 25:
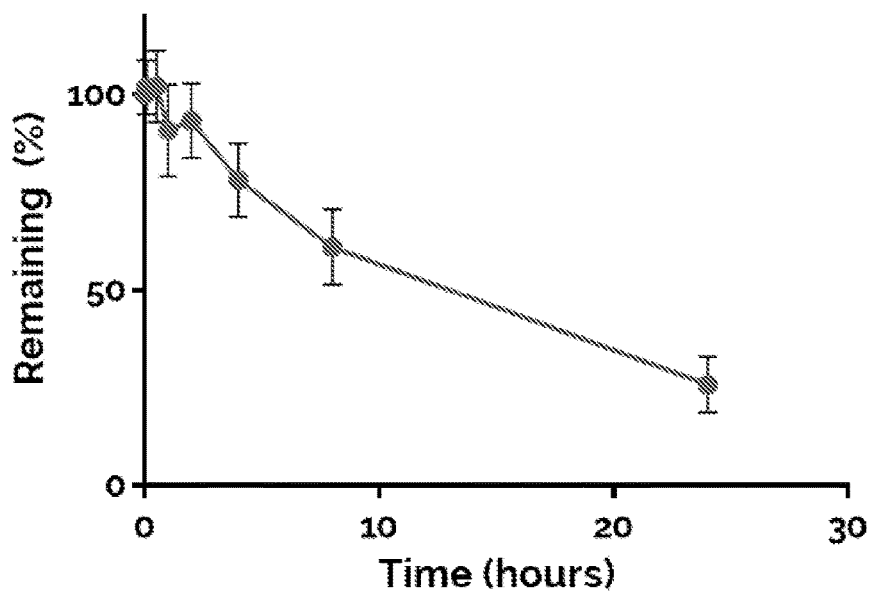
FIG. 25 is a graph showing the stability of CPP9-sPDI (structure 23) in 25% human serum at 37° C.

The serum stability of CPP9-sPDI was evaluated by incubating the conjugate in 25% human serum at 37° C. over 24 hours. FIG. 25 shows a steady decrease in CPP9-sPDI over this period, such that 25% of the compound is detected at the end of the study. The observed level of serum stability (cargo region) may impact the $IC_{50}$ values measured for this compound.

Experimental Details

Peptide Synthesis and Labeling. Peptides were manually synthesized by SPPS on Rink amide resin by using Fmoc chemistry and 2-(7-aza-1H-benzotriazole-1-yl)-1,1,3,3-tetramethyluronium hexafluorophosphate (HATU) as the coupling agent. Coupling reactions typically involved 5 equiv of Fmoc-amino acids, 5 equiv of HATU, and 10 equiv of diisopropylethylamine (DIPEA) and were carried out at R.T. for 45 min. The peptides were cleaved off the resin and deprotected by treatment with 92.5% TFA, 2.5% water, 2.5% triisopropylsilane, and 2.5% 1,3-dimethoxybenzene for 3 h at R.T. The solvents were removed by flowing a stream of $N_2$ over the solution and the residue was triturated with cold diethylether. The crude peptides were purified by reversed-phase HPLC equipped with a C18 column, which was eluted with linear gradients of acetonitrile (containing 0.05% TFA) in $ddH_2O$ (containing 0.05% TFA). Fluorescent labeling of the peptides were conducted in solution-phase. Lyophilized peptides were incubated with 5 equiv. of an activated fluorescent labelling reagent (e.g., fluorescein isothiocyanate or 5(6)-carboxynaphthofluorescein succinimidyl ester) and 5 equivalents of DIPEA in DMF for 2 h. The reaction was quenched by TFA and the labelled peptides were purified again by HPLC and their authenticity was confirmed by MALDI-TOF mass spectrometry.

Peptide Stapling with DCA. Cysteine-containing peptides were dissolved in 1 mL of DMF containing 100 mM $NH_4HCO_3$ (pH=8.1) and 1.1 equiv. of tris(2-carboxyethyl)phosphine (TCEP) to give a peptide concentration of ~0.1 mM. The solution was incubated with mixing on a rotary shaker for 1 h at R.T. After that, 1.5 equiv. of dichloroacetone in DMF was added to the mixture and the solution was incubated at RT for 3 h (with mixing). The reaction product was purified by reversed-phase HPLC and analyzed by MALDI-TOF MS.

Synthesis of Aminoxy-CPP9.

CPP9 was synthesized by standard SPPS with a miniPEG-$N^{\varepsilon}$-4-methoxytrityl-L-lysine moiety added at the C-terminus. While still on resin, the Mtt group on the lysine side chain was selectively removed by treatment of 2% (v/v) TFA in DCM for 1 h. The resin was then incubated with 5 equiv. of (Boc-aminoxy)acetic acid, 5 equiv. of diisopropylcarbodiimide (DIC), and 5 equiv. of HOBT in DCM/DMF (1:1 v/v) for 1 h (twice). The resulting aminoxy-CPP9 peptide was cleaved off the resin, purified by HPLC, and analyzed by MALDI-TOF MS as described previously.

Synthesis of CPP9-Stapled Peptide Conjugates by Oxime Formation.

DCA-stapled peptide (0.5 mM) was dissolved in 10 mL of 100 mM $NH_4OAc$ solution (pH 4.5) containing 100 mM aniline. Aminoxy-CPP9 (2.0 equiv) was added to the above solution and the mixture was incubated at R.T. overnight (with mixing). The reaction product was purified by reversed-phase HPLC equipped with a C18 column, which was eluted with a linear gradient of 10-60% acetonitrile in $ddH_2O$ (containing 0.05% TFA). Authenticity of the reaction products was confirmed by MALDI-TOF MS (see Figure S1 for an example).

Expression and Purification of GST-MDM2.

*E. coli* BL21(DE3) cells were transformed with the prokaryotic vector pGEX-6P-2, which encodes the human MDM2 gene (residues 17-125). Cells were grown at 37° C. in Luria broth supplemented with 100 μg/mL ampicillin to an $OD_{600}$ of 0.6 and protein expression was induced for 5 h at 30° C. by the addition of 1 mM IPTG. Cells were pelleted by centrifugation at 2,000 rpm for 30 min. The cell pellet was resuspended in 50 mL of lysis buffer (50 mM Tris-HCl, pH 7.4, 300 mM NaCl, 2.5 mM EDTA, 0.02% $NaN_3$, and 2 mM DTT) and lysed by sonication on ice. The lysate was centrifuged at 15,000 rpm in a SS-34 fixed angle rotor for 30 min. The supernatant was loaded onto a glutathione-Sepharose column and the bound protein was eluted with lysis buffer containing 10 mM GSH.

MTT Assay.

HCT116 p53 wild type and HCT116 p53$^{-/-}$ cells were seeded in 96-well plate with $3\times10^3$ cells per well, and allowed to grow overnight. Different concentrations of peptides (0-12.5 μM) were added to the cells in McCoy's 5A medium supplemented with 10% FBS and 1% penicillin/streptomycin and incubated at 37° C. for 48 h in the presence of 5% $CO_2$. After that, 10 μL of an MTT stock solution (5 mg/mL) was added into each well and the plate was incubated at 37° C. for 4 h. 100 μL of SDS-HCl solubilizing solution was added and the plate was incubated at 37° C. overnight. The absorbance of the formazan product formed was measured at 570 nm on a Tecan microtiter plate reader.

Flow Cytometry.

HeLa cells were seeded in 12-well plates at $1.5\times10^5$ cells per well for 24 h. The next day, naphthofluorescein-labelled peptide (5 μM) was added to the cells in DMEM medium supplemented with 10% fetal bovine serum (FBS) and 1% penicillin/streptomycin and the cells were incubated at 37° C. for 2 h in the presence of 5% $CO_2$. The medium containing the peptide was removed and the cells were washed with DPBS twice. The cells were detached from the plate with 0.25% trypsin, pelleted by centrifugation at 250 g for 5 min, washed twice with DPBS, resuspended in DPBS, and analyzed on a BD FACS LSR II or Aria III flow cytometer. For NF-labelled peptides, a 633-nm laser was used for excitation and the fluorescence emission was analyzed in the APC channel. Data were analyzed using the Flowjo software (Tree Star).

What is claimed is:

1. A polypeptide conjugate comprising a cyclic cell penetrating peptide (cCPP) and a stapled peptide having a structure according to Formula IA or IB:

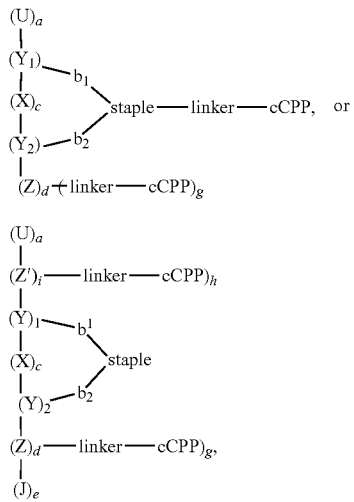

wherein:
the stapled peptide comprises U, $Y_1$, $Y_2$, X, Z, J, Z' or a combination thereof and a staple and contains at least one region having an alpha-helical structure;
each of X and Z, at each instance, are independently an amino acid;
U, at each instance and when present, is independently an amino acid;
J, at each instance and when present, is independently selected from an amino acid;
Z', at each instance and when present, is independently an amino acid;
a is a number in the range of from 0 to 500;
c is 3, 6, or 10; d is a number in the range of from 1 to 500;
e is a number in the range of from 0 to 500; each of g and h are independently and at each instance 0 or 1, provided that in at least one instance g is 1;
i is a number in the range of from 0 to 100;
$Y_1$ is an amino acid which has a side chain which forms a first bonding group ($b_1$) to the staple;
$Y_2$ is an amino acid which has a side chain which forms a second bonding group (b2) to the staple;
cCPP is a cyclic peptide comprising about 4 to about 13 amino acids, wherein the about 4 to about 13 amino acids include at least two arginines and at least two amino acids with hydrophobic side chains;

wherein:
the staple comprises an amide, alkylene substituted with an oxo or N-oxide, or an aryl;
the linker comprises at least one amino acid, alkylene, alkenylene, alkynylene, aryl, cycloalkyl, cycloalkenyl, cycloalkynyl, heterocyclyl, heteroaryl, ether, or a combination thereof, each of which are optionally substituted; and
each of b1 and b2 are independently thioether, disulfide, amide, ester, or ether.

2. The polypeptide conjugate of claim 1, wherein the cCPP has a sequence comprising any of Formula IIIA-D:

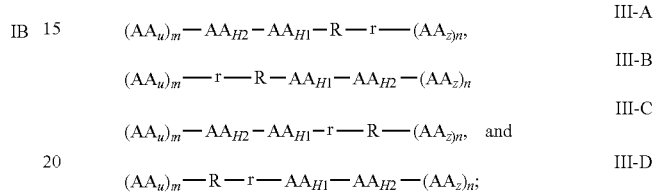

wherein:
each of $AA_{H1}$ and $AA_{H2}$ are independently a D or L hydrophobic amino acid;
at each instance and when present, each of $AA_u$, and $AA_z$ are independently a D or L amino acid; and
wherein the sum of m and n is from 2 to 6.

3. The polypeptide conjugate of claim 1, wherein:
c is 3.

4. The polypeptide conjugate of claim 1, wherein:
(i) U is absent, and Z' is either the N-terminus or the C-terminus of the stapled peptide;
(ii) U is present, a is 1, and U is either the N-terminus or the C-terminus of the stapled peptide; or
(iii) U is present, a is 2 or more, and the terminal U is either the N-terminus or the C-terminus of the stapled peptide.

5. A cell comprising the polypeptide conjugate of claim 1.

6. A method for cellular delivery of a stapled peptide, the method comprising contacting a cell with the polypeptide conjugate of claim 1.

7. A method for making the polypeptide conjugate of claim 1, the method comprising conjugating a stapled peptide and a cCPP.

8. A method for making a polypeptide conjugate of claim 1, the method comprising conjugating a peptide to at least one cCPP, and stapling the peptide.

9. A pharmaceutical composition comprising the polypeptide conjugate of claim 1.

10. The polypeptide conjugate of claim 1, comprising any one of peptide 4, peptide 11, peptide 13, peptide 15, peptide 17, peptide 19, peptide 21, or peptide 23:

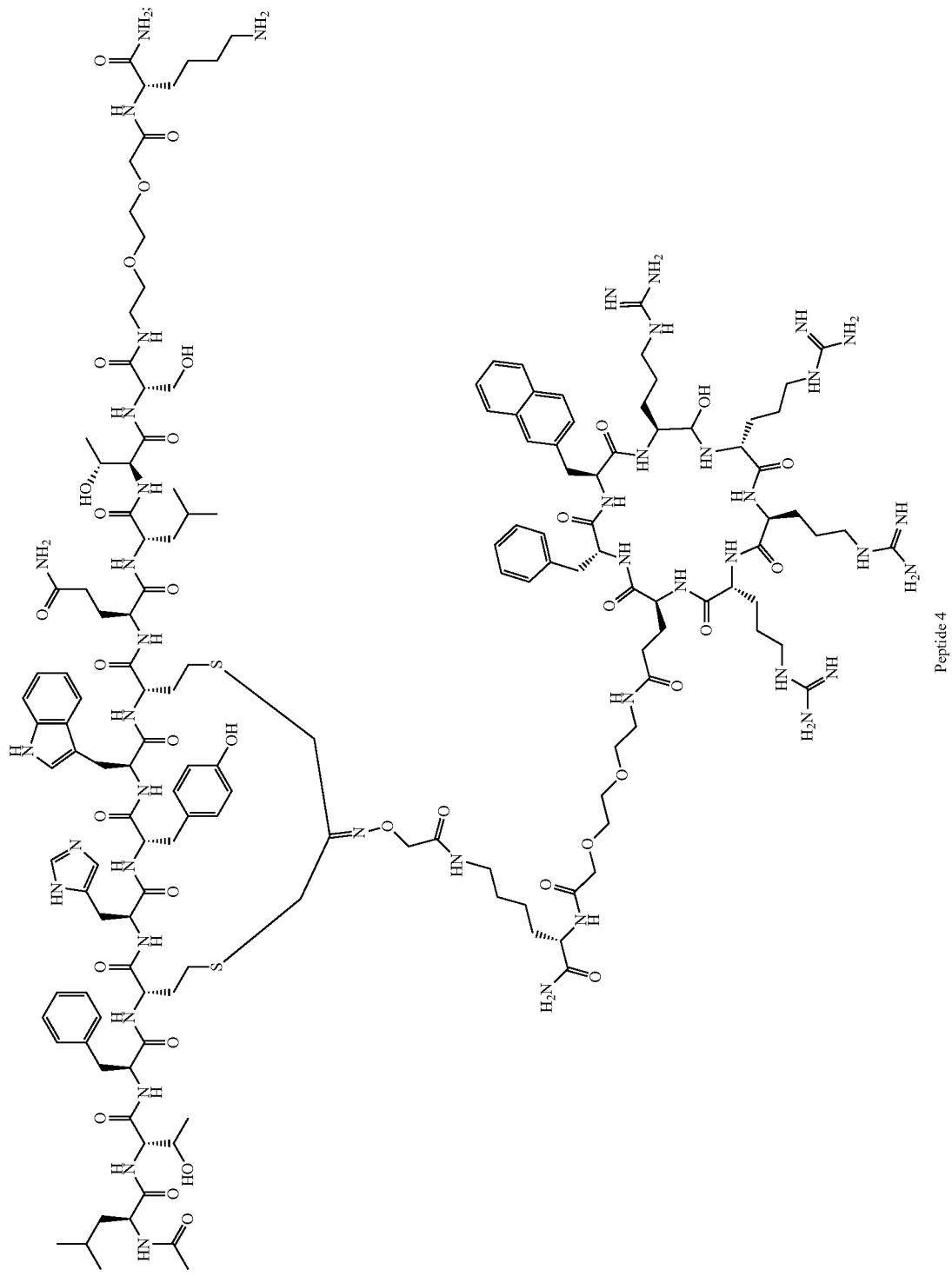
Peptide 4

-continued
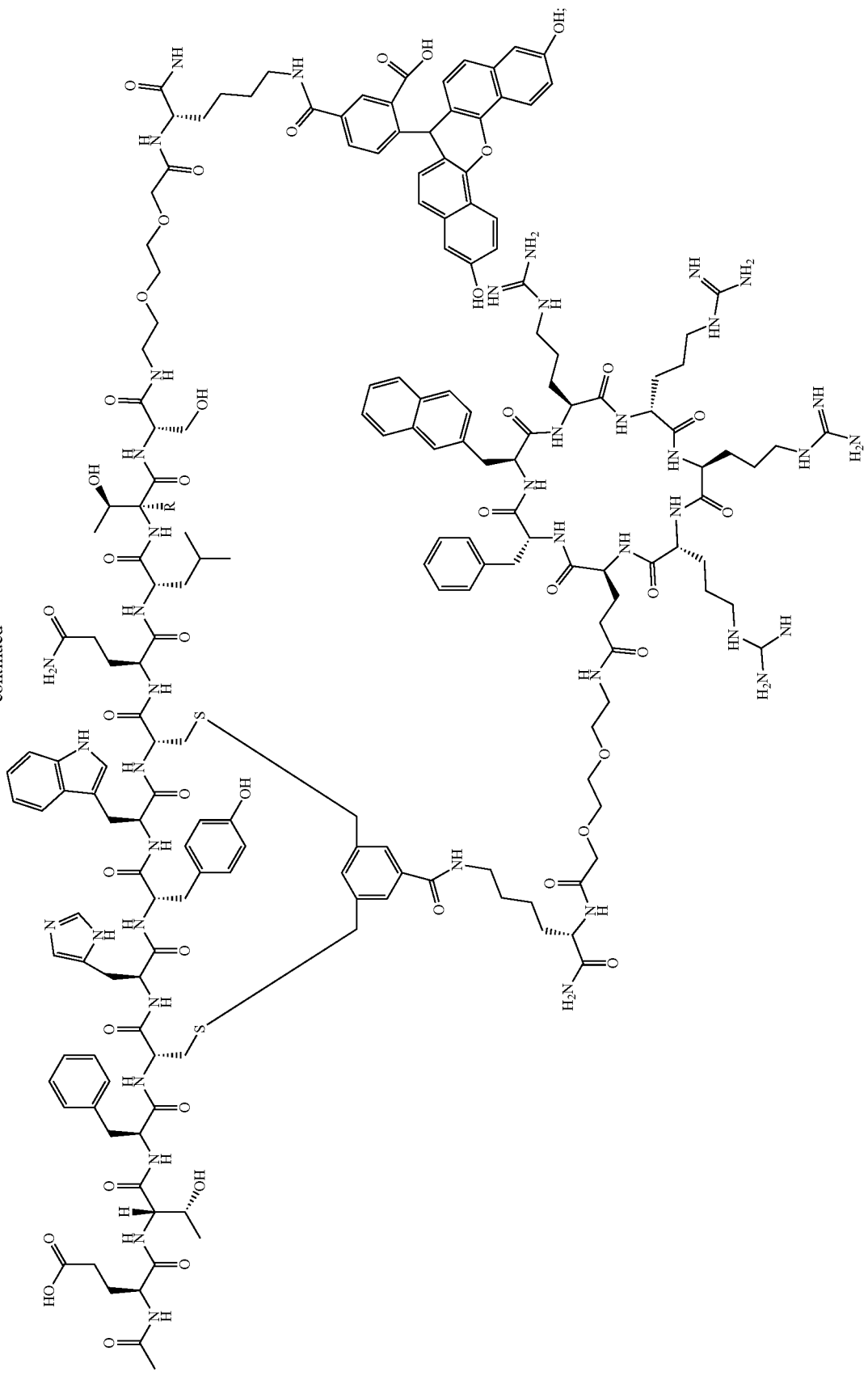
Peptide 11

-continued
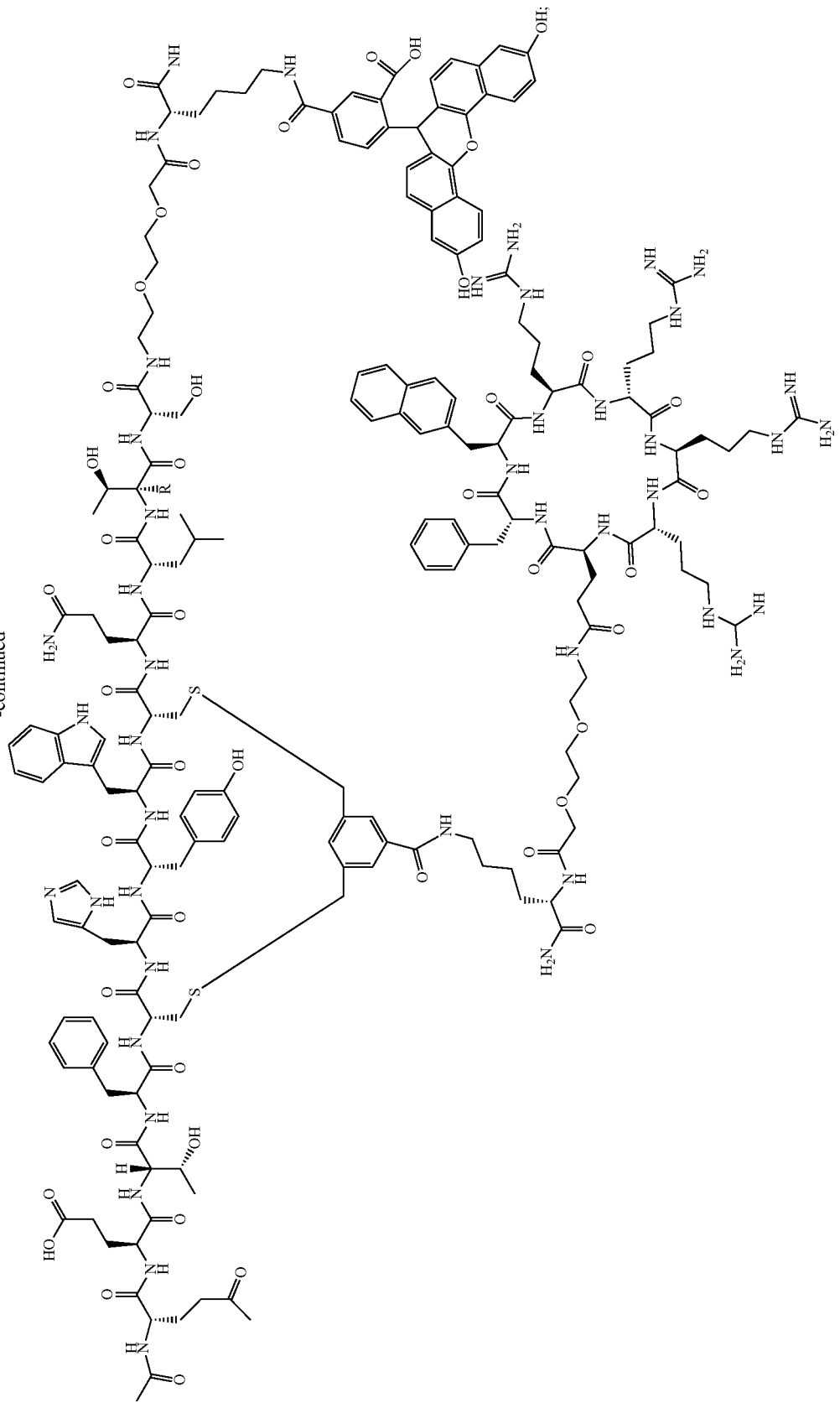
Peptide 13

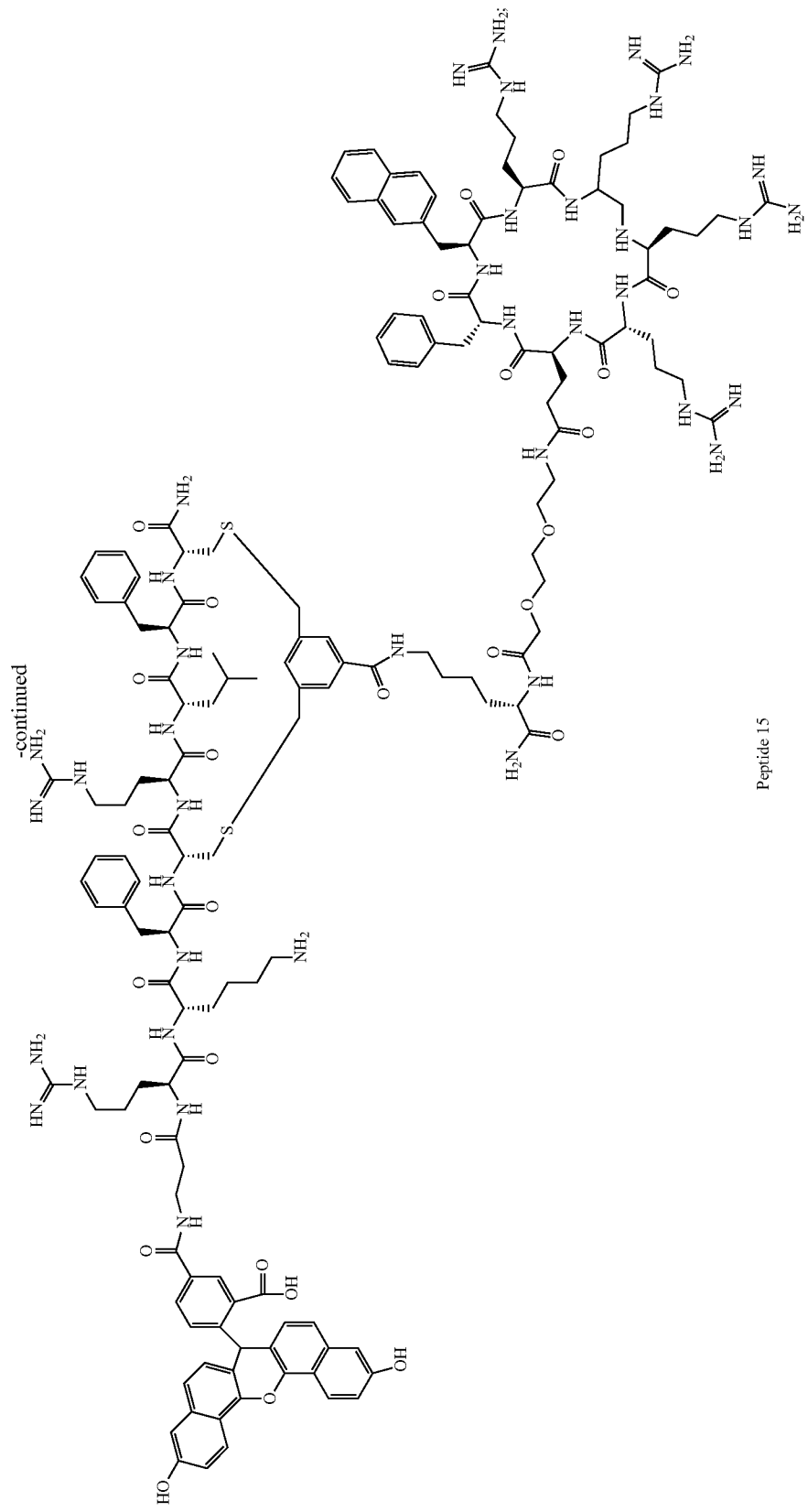
Peptide 15

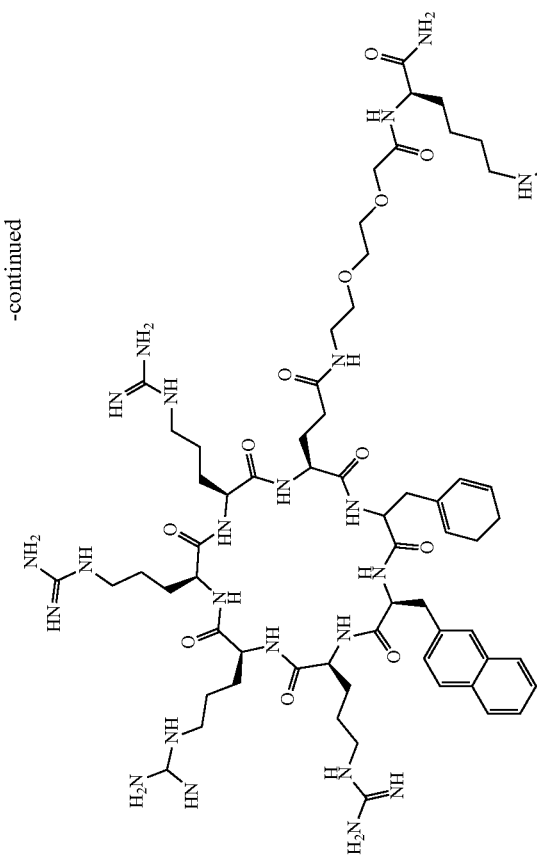
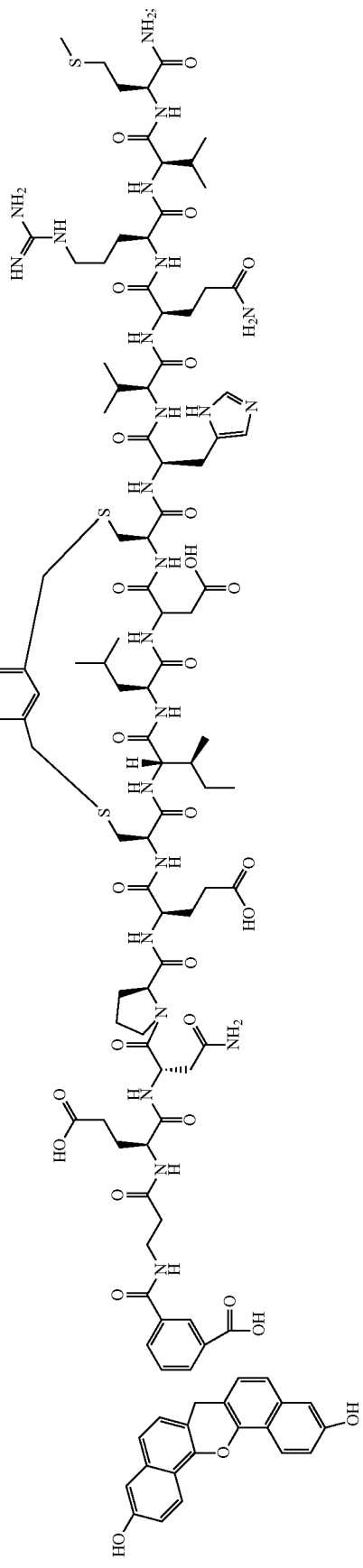
Peptide 17

-continued
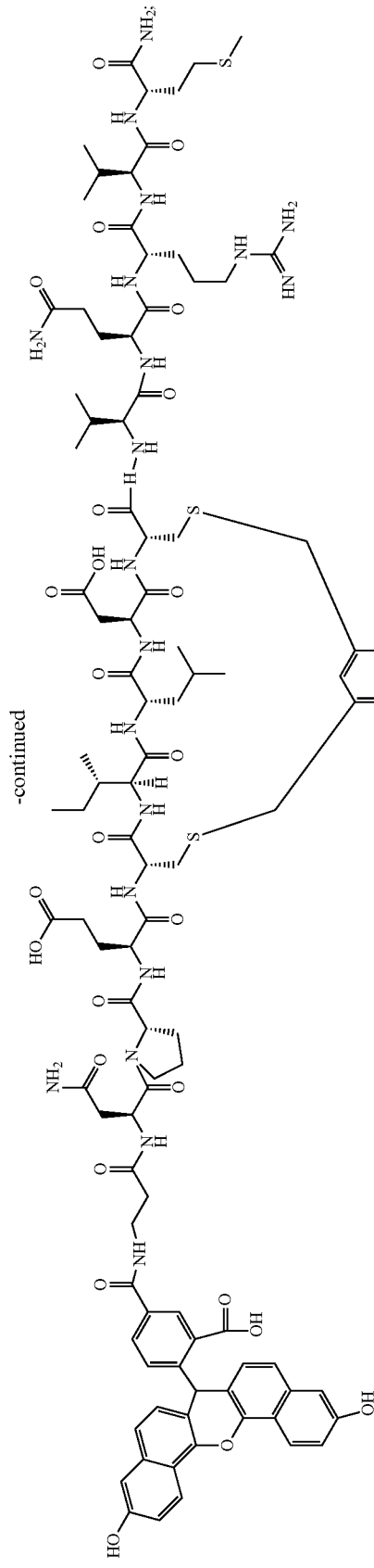
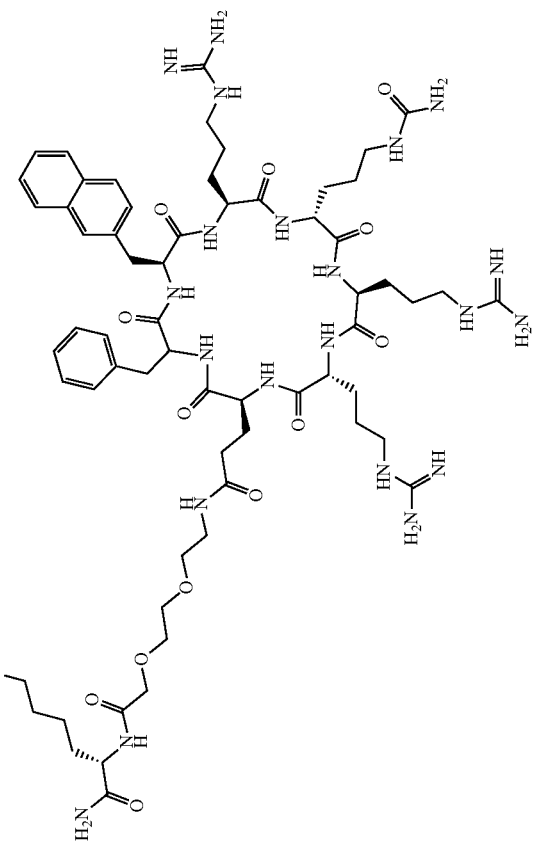
Peptide 19

-continued
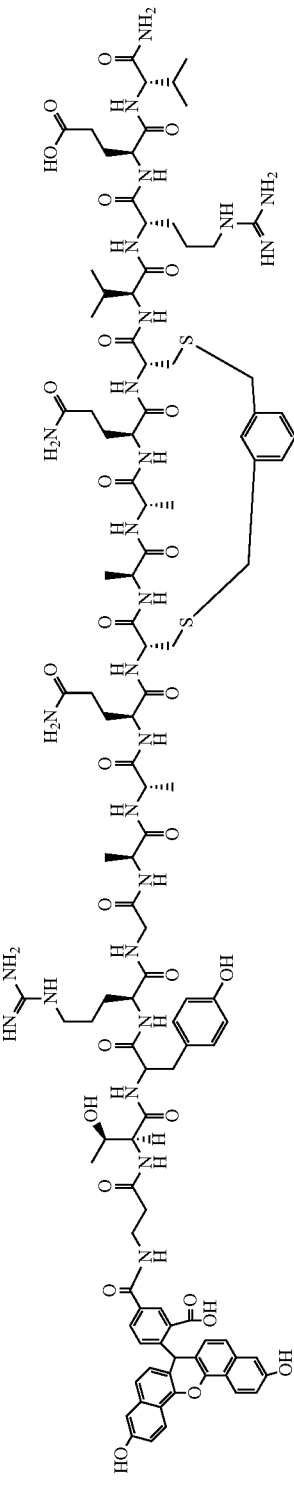
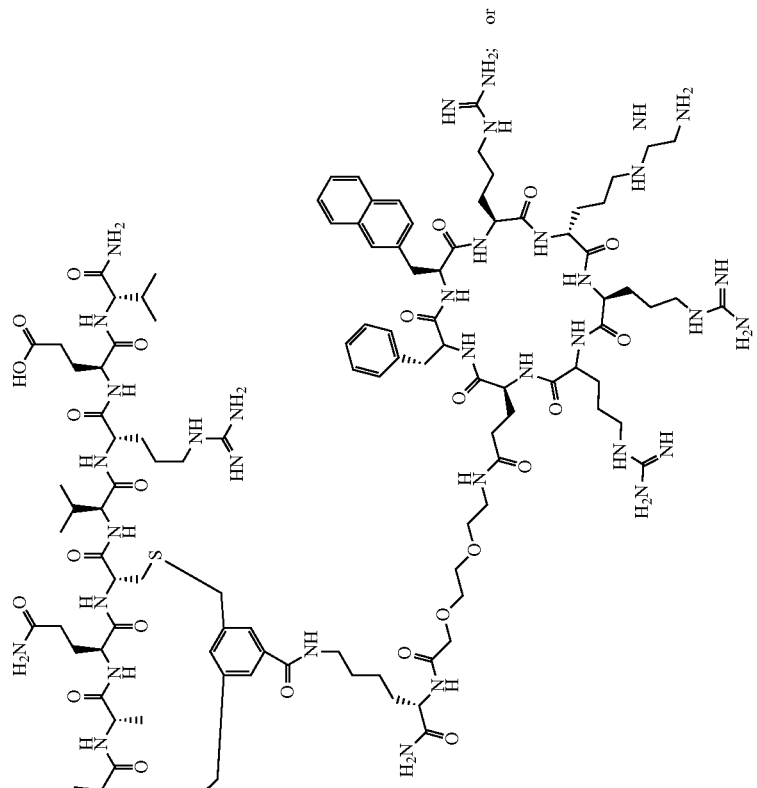
Peptide 21

-continued
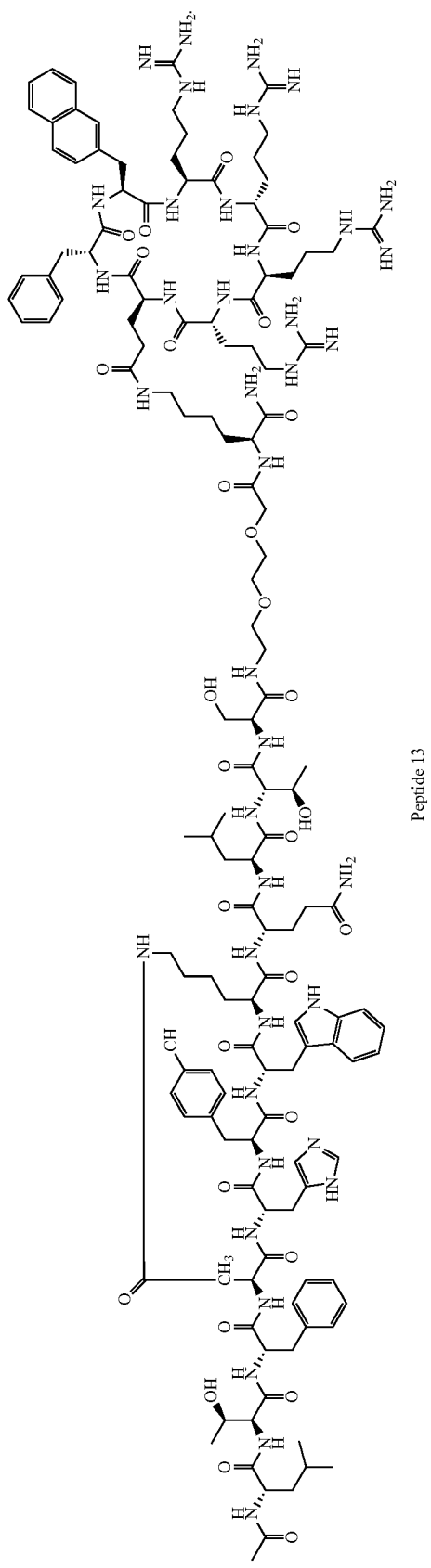
Peptide 13

11. The polypeptide conjugate of claim 1 having the following structure:
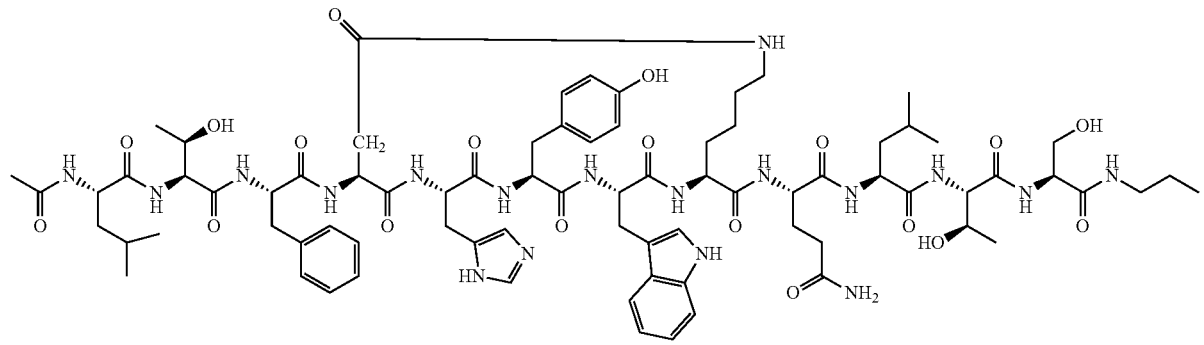
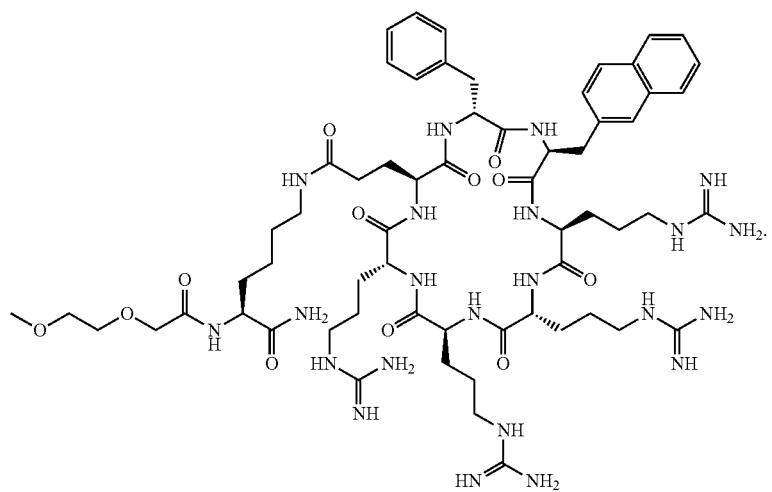

12. The polypeptide conjugate of claim 1, wherein the linker has a structure L-1 or L-2:
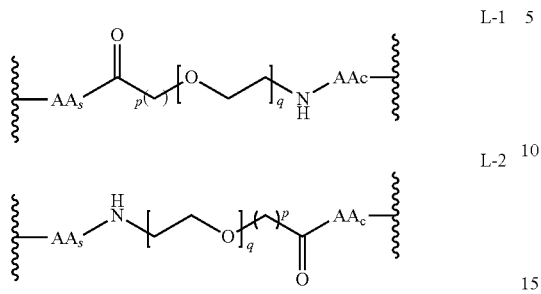
L-1
L-2
wherein:
  $AA_s$ is a side chain or terminus of an amino acid on the peptide or staple;
  $AA_c$ is a side chain or terminus of an amino acid of the cCPP;
  p is an integer from 0 to 10; and
  q is an integer from 1 to 50.
* * * * *